(12) United States Patent
Kelly et al.

(10) Patent No.: US 7,560,488 B2
(45) Date of Patent: Jul. 14, 2009

(54) METHODS FOR TREATING TRANSTHYRETIN AMYLOID DISEASES

(75) Inventors: Jeffery W. Kelly, LaJolla, CA (US); Yoshiki Sekijima, Matsumoto (JP)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/527,020

(22) Filed: Sep. 25, 2006

(65) Prior Publication Data

US 2007/0078186 A1 Apr. 5, 2007

Related U.S. Application Data

(62) Division of application No. 10/741,649, filed on Dec. 19, 2003, now Pat. No. 7,214,695.

(60) Provisional application No. 60/465,435, filed on Apr. 24, 2003, provisional application No. 60/435,079, filed on Dec. 19, 2002.

(51) Int. Cl.
*A61K 31/192* (2006.01)
(52) U.S. Cl. .................................. 514/568
(58) Field of Classification Search ............... 514/568
See application file for complete search history.

(56) References Cited

U.S. PATENT DOCUMENTS

| | | | |
|---|---|---|---|
| 3,551,443 A | 12/1970 | Duennenberger et al. | |
| RE29,608 E | 4/1978 | Evans et al. | |
| 4,416,892 A | 11/1983 | Dawson | |
| 5,200,420 A | 4/1993 | Goldmann et al. | |
| 5,254,692 A | 10/1993 | Goldmann et al. | |
| 5,354,759 A | 10/1994 | Oku et al. | |
| 5,412,099 A | 5/1995 | Goldmann et al. | |
| 5,441,946 A | 8/1995 | Pauls et al. | |
| 5,552,426 A | 9/1996 | Lunn et al. | |
| 5,563,128 A | 10/1996 | Pauls et al. | |
| 5,714,496 A | 2/1998 | Brown et al. | |
| 5,837,390 A | 11/1998 | Kishii et al. | |
| 6,107,491 A | 8/2000 | Eldin | |
| 6,277,853 B1 | 8/2001 | Perez et al. | |
| 6,420,418 B1 | 7/2002 | Hagmann et al. | |
| 6,495,568 B1 | 12/2002 | Dack et al. | |
| 6,544,989 B2 | 4/2003 | Mathews et al. | |
| 6,589,953 B2 | 7/2003 | Perez et al. | |
| 6,602,619 B2 | 8/2003 | Lin et al. | |
| 6,623,930 B2 | 9/2003 | Kerwin et al. | |
| 6,689,887 B2 | 2/2004 | Kerwin et al. | |
| 6,693,098 B2 | 2/2004 | Cournoyer et al. | |
| 6,794,403 B2 | 9/2004 | Malamas et al. | |
| 2001/0056100 A1 | 12/2001 | Cournoyer et al. | |
| 2002/0049142 A1 | 4/2002 | Mathews et al. | |
| 2002/0061891 A1 | 5/2002 | Perez et al. | |
| 2002/0107258 A1 | 8/2002 | Kerwin et al. | |
| 2003/0040525 A1 | 2/2003 | Kerwin et al. | |
| 2003/0129448 A1 | 7/2003 | Lin et al. | |
| 2003/0199562 A1 | 10/2003 | Malamas et al. | |
| 2003/0220367 A1 | 11/2003 | Cournoyer et al. | |
| 2003/0232877 A1 | 12/2003 | Sikorski et al. | |
| 2004/0006056 A1 | 1/2004 | Harris et al. | |
| 2004/0029933 A1 | 2/2004 | Zhao et al. | |
| 2004/0048858 A1 | 3/2004 | Sikorski et al. | |
| 2004/0102435 A1 | 5/2004 | Barlaam et al. | |
| 2004/0209776 A1 | 10/2004 | Farooq et al. | |
| 2004/0229894 A1 | 11/2004 | Kerwin et al. | |

FOREIGN PATENT DOCUMENTS

| | | |
|---|---|---|
| DE | 602336 | 8/1934 |
| DE | 2314238 | 9/1973 |
| DE | 4208535 | 9/1992 |
| DE | 4304650 | 8/1994 |
| EP | 0479161 | 4/1992 |
| EP | 0611660 | 8/1994 |
| JP | 04-183754 | 6/1992 |
| JP | H5-17458 | 1/1993 |
| JP | 06-073050 | 3/1994 |
| JP | 06-073051 | 3/1994 |
| JP | 06-239849 | 8/1994 |
| JP | 6336586 | 12/1994 |
| JP | 07-097379 | 4/1995 |
| JP | 09227576 | 9/1997 |
| JP | 09328678 | 12/1997 |
| JP | 09165391 | 6/1999 |
| JP | 2000100569 | 4/2000 |
| JP | 2001055332 | 2/2001 |
| JP | 2001064166 | 3/2001 |
| JP | 2001064205 | 3/2001 |
| JP | 2001242165 | 9/2001 |
| JP | 2001291593 | 10/2001 |
| JP | 2001301329 | 10/2001 |
| JP | 2002003368 | 1/2002 |
| JP | 2004250411 | 9/2004 |
| JP | 2004302049 | 10/2004 |
| WO | WO98/27972 | 7/1998 |
| WO | WO00/78733 | 12/2000 |
| WO | WO01/14354 | 3/2001 |
| WO | WO01/27088 | 4/2001 |
| WO | WO01/74786 | 10/2001 |
| WO | WO02/016333 | 2/2002 |
| WO | WO02/46168 | 6/2002 |
| WO | WO02/051821 | 7/2002 |

(Continued)

OTHER PUBLICATIONS

Purkey et al., PNAS, May 8, 2001, vol. 98, No. 10, p. 5566-5571.*

(Continued)

*Primary Examiner*—Kamal A Saeed
*Assistant Examiner*—Yong Chu
(74) *Attorney, Agent, or Firm*—Jones Day

(57) ABSTRACT

Kinetic stabilization of the native state of transthyretin is an effective mechanism for preventing protein misfolding. Because transthyretin misfolding plays an important role in transthyretin amyloid diseases, inhibiting such misfolding can be used as an effective treatment or prophylaxis for such diseases. Treatment methods are disclosed.

5 Claims, 10 Drawing Sheets

FOREIGN PATENT DOCUMENTS

| | | |
|---|---|---|
| WO | WO03/020698 | 3/2003 |
| WO | WO03/045930 | 6/2003 |
| WO | WO03/074516 | 9/2003 |
| WO | WO03/089418 | 10/2003 |
| WO | WO2004/046123 | 6/2004 |
| WO | WO2004/064771 | 8/2004 |
| WO | WO2004/083189 | 9/2004 |
| WO | WO2004/083195 | 9/2004 |
| WO | WO2004/084824 | 10/2004 |
| WO | WO2004/092140 | 10/2004 |
| WO | WO2004/094395 | 11/2004 |
| WO | WO2004/098494 | 11/2004 |

OTHER PUBLICATIONS

Google saerch result under Dolobid 250 mg.*
Aydin et al., "Analgesic and Antispasmodic Activities of 2-(2-Nitrophenyl)-1*H*-benzimidazole 5-Carboxylic Acid: Evidence for the Importance of the 2-(o-Substituted Phenyl) Group", *Pharmazie* 58:405-408 (2003).
Baures et al., "Discovering Transthyretion Amyloid Fibril Inhibitors by Limited Screening", *Bioorganic & Medicinal Chemistry* 6:1389-1401 (1998).
Baures et al., "Synthesis and Evaluation of Inhibitors of Transthyretin Amyloid Formation Based on the Non-Steroidal Anti-Inflammatory Drug, Flufenamic Acid", *Bioorganic & Medicinal Chemistry* 7:1339-1347 (1999).
Beaulieu et al., "Non-Nucleoside Inhibitors of the Hepatitis C Virus NS5B Polymerase: Discovery and Preliminary SAR of Benzimidazole Derivatives", *Bioorganic and Medicinal Chemistry Letters* 14:119-124 (2004).
Editorial, "Orphan Amyloid Diseases", *Nature Structural Biology* 7(4):259-260 (2000).
Essassi and Fifani, "Synthese et Heterocyclization des (Pyrazolyl-3(5))-2-Benzimidazoles en Catalyse par Transfert de Phase", *Bull Soc Chim Belg* 96(1):63-67 (1987).
Göker and Tebrizli, "Synthesis of 1,2-Disubstituted Benzimidazole-9(6)-Carboxamides and Evaluation of Their Antimicrobial Activity", *Il Farmaco* 51(1):53-58 (1996).
Göker et al., "Synthesis and Antimicrobial Activity of Some New 2-Phenyl-*N*-Substituted Carboxamido-1*H*-Benzimidazole Derivatives", *Arch Pharm Med Chem* 334::148-152 (2001).
Green et al., "Synthesis and Characterization of Potent Bivalent Amyloidosis Inhibitors That Bind Prior to Transthyretin Tetramerization", *J Am Chem Soc* 125:13404-13414 (2003).
Hammarstrm et al., "*Trans*-Suppression of Misfolding in an Amyloid Disease", *Science* 293:2459-2462 (2001).
Hammarström et al., "Prevention of Transthyretin Amyloid Disease by Changing Protein Misfolding Energetics", *Science* 299:713-716 (2003).
Haskell et al., "Neuraminidase Inhibition and Viral Chemotherapy", *Journal of Medicinal Chemistry* 13(4):697-704.
Hillard et al., Multiple Mechanisms of Action for Inhibitors of Histidine Protein Kinases from Bacterial Two-Component Systems, *Antimicrobial Agents and Chemotherapy* 43(7):1693-1699 (1999).
Hizano and Yabuta, "Synthesis of Organosulfur Compounds. VIII. Cyclization Products from the Modified Willgerodt-Kindler Reaction", *Chem Pharm Bull* 21(3):511-517 (1973).
Jennings et al., "Efficient Synthesis of (≠)-*seco*-Cyclopropaneindoline Analogs of CC-1065", *Heterocyclic Communication* 7(1) (2001).
Kelly, "The Environment Dependency of Protein Folding Best Explains Prion and Amyloid Diseases", *PNAS* 95:930-932 (1998).
Klabunde et al., "Rational Design of Potent Human Transthyretin Amyloid Disease Inhibitors", *Nature Structural Biology* 7(4):31321 (2000).
Kim et al., "Structure-Activity Relationships of Benzimidazoles and Related Heterocycles as Topoisomerase I Poisons", *Bioorganic and Medicinal Chemistry* 4(4):621-630 (1996).
Kreimeyer et al., "Sumarin Analogues with a 2-Phenylbenzimidazole Moiety as Partial Structure", *Pharmazie* 52(4):268-271 (1997).
Lashuel, et al., "New Class of inhibitors of Amyloid-beta Fibril Formation", *J. Biol. Chem.* 277(45):42881-42890 (2002).
Lee et al., "Solid-Phase Combinatorial Synthesis of Benzothiazole and 2,3-Dihydro-[1,5]-Benzothiazepine Derivatives", *Tetrahedron Letters* 42:109-111 (2001).
Lin et al., "Bioisosteric Replacement of Anilide with Benzoxazole: Potent and Orally Bioavailable Antagonists of VLA-4", *Bioorganic & Medicinal Chem Letters* 14:2331-2334 (2004).
Miroy et al., "Inhibiting Transthyretion Amyloid Fibril Inhibitors via Protein Stabilization", *PNAS* USA 93:15051-15056 (1996).
Oza et al., "Synthesis and Evaluation of Anthranilic Acid-Based Trabsthyretin Amyloid Fibril Inhibitors", *Bioorganic & Medicinal Chem Letters* 9:1-6 (1999).
Oza et al., "Synthesis, Structure and Activity of Diclofenac Analogues as Transthyretin Amyloid Fibril Formation Inhibitors", *J Med Chem* 45:321-332 (2002).
Peterson, et al., "Inhibiting Transthyretin Conformational Changes That Leat to Amyuloid Fibril Formation", *PNAS* 95:12956-12960 (1998).
Petrassi et al., "Structure-Based Design of N-Phenyl Phenoxazine Transthyretion Amyloid Fibril Inhibitors", *J Am Chem Soc* 122(10):2178-2192 (2000).
Purkey et al., "Evaluating the Binding Selectivity of Transthyretion Amyloid Fibril Inhibitors in Blood Plasma", *PNAS* USA 98(10):5566-5571 (2001), cited.
Razavi et al., "Benzoxazoles as Transthyretion Amyloid Fibril Inhibitors: Synthesis, Evaluation, and Mechanism of Action", *Angew Chem Int Ed.* 42:2758-2761 (2003).
Razavi et al., "Benzoxazoles as Transthyretion Amyloid Fibril Inhibitors: Synthesis, Evaluation, and Mechanism of Action", *Angew Chem* 115:2864-2867 (2003).
Rtischev et al., "Absorption and Luminescence in the Series of 2-Phenylbenzothiazole and Related Compounds", *Russian Journal of General Chemistry* 63(2):303-309 (1993).
Sacchettini and Kelly, "Therapeutic Strategies for Human Amyloid Diseases", *Nature Reviews* 1:267-275 (2002).
Singh et al., "Synthetic Utility of Catalytic Fe(III)/Fe(II) Redox Cycling Towards Fused Heterocycles: a Facile Acces to Substituted Benzimidazole, Bis-Benzimidazole and Imidazopyridine Derivatives", *Synthesis* 10:1380-1390 (2000).
Stephes and Bower, "The Preparation of Benziminazoles and Benzoxazoles from Schiff's Bases, Part II," *J Chem Soc* (UK) 1722-1726 (1950).
Xue et al., "Design, Synthesis and In Vitro Activities of a Series of Benzimidazole/Benzoxazole Glycoprotein IIb/IIIa Inhibitors", *Bioorganic & Medicinal Chem Letters* 6(3):339-344 (1996).
Tojo et al., "Diflunisal stabilizes familial amyloid polyneuropathy-associated transthretin variant tetramers in serum against dissociation required for amyloidogenesis", *Neuroscience Research* 56:441-449 (2006).
Sekijima et al., "Orally administered diflunisal stabilizes transthyretin against dissociation required for amyloidogenesis" *Amyloid* 13(4): 236-249 (2006).

* cited by examiner

METHODS FOR TREATING TRANSTHYRETIN AMYLOID DISEASES

CROSS REFERENCE TO RELATED APPLICATIONS

This application is a divisional of U.S. application Ser. No. 10/741,649, filed Dec. 19, 2003 now U.S. Pat. No. 7,214,695, entitled "COMPOSITIONS AND METHODS FOR STABILIZING TRANSTHYRETIN AND INHIBITING TRANSTHYRETIN MISFOLDING." U.S. application Ser. No. 10/741,649 claims priority from U.S. Provisional Application No. 60/435,079, filed Dec. 19, 2002, and U.S. Provisional Application No. 60/465,435, filed Apr. 24, 2003. The entire disclosures of the above-referenced applications are incorporated herein by reference in their entirety.

STATEMENT AS TO FEDERALLY SPONSORED RESEARCH

Funds used to support some of the studies disclosed herein were provided by grant number NIH DK 46335 awarded by the National Institutes of Health. The Government may have certain rights in the invention.

FIELD OF THE INVENTION

The invention relates generally to protein misfolding. More particularly, this invention provides compositions and methods for stabilizing transthyretin, inhibiting transthyretin misfolding, and treating amyloid diseases associated thereto.

BACKGROUND OF THE INVENTION

Transthyretin (TTR) is a 55 kDa homotetrameric protein present in serum and cerebral spinal fluid. The function of TTR is to transport L-thyroxine ($T_4$) and holo-retinol binding protein (RBP). TTR is one of greater than 20 nonhomologous amyloidogenic proteins that can be transformed into fibrils and other aggregates leading to disease pathology in humans. These diseases do not appear to be caused by loss of function due to protein aggregation. Instead, aggregation appears to cause neuronal/cellular dysfunction by a mechanism that is not yet clear.

Under denaturing conditions, rate limiting wild type TTR tetramer dissociation and rapid monomer misfolding enables misassembly into amyloid, putatively causing senile systemic amyloidosis (SSA). Dissociation and misfolding of one of more than eighty TTR variants results in familial amyloid polyneuropathy (FAP) and familial amyloid cardiomyopathy (FAC).

The TTR tetramer has two $C_2$ symmetric $T_4$-binding sites. Negatively cooperative binding of $T_4$ is known to stabilize the TTR tetramer and inhibit amyloid fibril formation. Unfortunately, less than 1% of TTR has $T_4$ bound to it in the human serum, because thyroid-binding globulin (TBG) has an order of magnitude higher affinity for $T_4$ in comparison to TTR. Furthermore, the serum concentration of $T_4$ is relatively low (0.1 μM) compared to that of TTR (3.6-7.2 μM).

SUMMARY OF THE INVENTION

The invention is based, at least in part, on the discovery that kinetic stabilization of the native state of transthyretin inhibits protein misfolding. This discovery is important because of the role that protein misfolding plays in a variety of disease processes, including transthyretin amyloid diseases. By inhibiting transthryetin misfolding, one can intervene in such a disease, ameliorate symptoms, and/or in some cases prevent or cure the disease.

The discovery that kinetic stabilization of the native state of transthyretin effectively inhibits misfolding allows for the development of therapeutic compositions with potentially high specificity and low toxicity. Thus, although exemplary biaryl reagents which have the ability to stabilize transthryetin are disclosed herein, one can design other reagents which selectively stabilize the protein. For example, as described herein, it is possible to design and prepare polychlorinated biphenyls, diflunisal analogs, or benzoxazoles that highly selective for binding to transthyretin and that stabilize the native state of transthyretin.

In on aspect, the invention features a method of screening for a compound that prevents or reduces dissociation of a transthyretin tetramer. The method can include the following steps: contacting a transthyretin tetramer with a candidate compound; and determining whether the candidate compound increases the activation energy associated with dissociation of the transthyretin tetramer, thereby preventing or reducing dissociation of the transthyretin tetramer. The method can optionally include an additional step of measuring the ability of the candidate compound to inhibit fibril formation.

In one embodiment, the method includes a step of determining whether the compound prevents dissociation of the transthyretin tetramer by destabilizing the dissociation transition state of the transthyretin tetramer. In another embodiment, the method includes a step of determining whether the compound prevents dissociation of the transthyretin tetramer by stabilization of the transthyretin tetramer more than the dissociative transition state.

The candidate compound used in such a method can optionally be a small molecule. Such a small molecule can stabilize the native state of transthyretin through tetramer binding, thereby slowing dissociation and amyloidosis under denaturing and physiological conditions through a kinetic stabilization mechanism. The compound optionally exhibits binding stoichiometry exceeding 0.1 to TTR in human blood when administered at a concentration of 10.6:M.

A small molecule can optionally have a molecular weight of less than 1500 and bind to transthyretin non- or positively cooperatively and impart a binding energy of >2.3 kcal/mol. The small molecule can exhibit $K_{d1}$ and $K_{d2}$<100 nM (e.g., <10 nM) and/or a high plasma concentration, which both contribute to protein stabilization exceeding 2.0 kcal/mol. The small molecule can also decrease the yield of amyloidosis and decrease the rate of acid-mediated or MeOH mediated amyloidogenesis and/or decrease the rate of urea mediated TTR dissociation.

In some embodiments, the small molecule includes biphenyl amines, biphenyls, oxime ethers, benzazoles or other structures composed of two aromatic rings where one bears hydrophilic groups such as an acid or a phenol and the other bears hydrophobic groups such as halogens or alkyls.

In one embodiment, the candidate compound is a biaryl where one ring bears a hydrophilic substituent(s) and the other has hydrophobic substituents or a biaryl where both rings bear at least one hydrophilic substituent. The hydrophilic group can be a phenol, a COOH, a benzyl alcohol, a boronic acid or ester, a tetrazole, an aldehyde or a hydrated aldehyde or a functional group that serves as either a H-bond donor or acceptor to the protein directly or through a water mediated H-bond. The biaryl can be a symmetrical biaryl having both rings substituted with hydrophilic functionality including phenols, carboxylates and alcohols and in some cases halogens to compliment the halogen binding pockets in TTR, e.g., a biaryl with the following functionality 3-Cl, 4-OH, 5-Cl and 3'-Cl, 4'-OH, 5'-Cl. In one embodiment, at least one ring of the biaryl is substituted with 2,4-difluoro or 3,5-difluoro or 2,6-difluoro or 3,5-dichloro or 3-Cl, 4-OH, 5-Cl or 3-F, 4-OH, 5-F, 3-COOH, 4-OH or 3-OH or 3-COOH or 4-COOH or 3-CH2OH or 4-CH2OH substituents. An exemplary biaryl is a polychlorinated biphenyl, e.g., a hydroxylated polychlorinated biphenyl wherein at least one ring one bears OH and/or Cl substituents including 3-Cl, 4-OH, 5-Cl or 2-Cl, 3-Cl, 4-OH, 5-Cl or 3,4-DiCl, or 2,3,4-trichloro or 2,3,4,5-tetrachloro. Halogens other than chloride can be used in the candidate compound. The candidate compound can be a benzoxazole.

In one embodiment, the candidate compound is a diflunisal analog. The structure of diflunisal as well as a variety of diflunisal analogs are described herein. The diflunisal analog can optionally have reduced or absent NSAID activity as compared to diflunisal. For example, the diflunisal analog can have reduced or absent cyclooxygenase inhibitor activity as compared to diflunisal.

In one embodiment, the method includes an additional step of determining whether the diflunisal analog exhibits NSAID activity. For example, the method can include a step of determining whether the diflunisal analog exhibits cyclooxygenase inhibitor activity.

The transthyretin used in the screening methods can be wild type transthyretin or a mutant transthyretin, such as a naturally occurring mutant transthyretin causally associated with the incidence of a transthyretin amyloid disease such as familial amyloid polyneuropathy or familial amyloid cardiomyopathy. Exemplary naturally occurring mutant transthyretins include, but are not limited to, V122I, V30M, L55P (the mutant nomenclature describes the substitution at a recited amino acid position, relative to the wild type; see, e.g., Saraiva et al. (2001) Hum. Mut. 17:493-503).

The invention also provides for methods for the stabilization of transthyretin in a tissue or in a biological fluid, and thereby inhibiting misfolding. Generally, the method comprises administering to the tissue or biological fluid a composition comprising a stabilizing amount of a compound described herein that binds to transthyretin and prevents dissociation of the transthyretin tetramer by kinetic stabilization of the native state of the transthyretin tetramer.

Thus, methods which stabilize transthyretin in a diseased tissue ameliorate misfolding and lessen symptoms of an associated disease and, depending upon the disease, can contribute to cure of the disease. The invention contemplates inhibition of transthyretin misfolding in a tissue and/or within a cell. The extent of misfolding, and therefore the extent of inhibition achieved by the present methods, can be evaluated by a variety of methods, such as are described in the Examples.

Accordingly, in another aspect the invention includes a method of treating a transthyretin amyloid disease, the method comprising administering to a subject diagnosed as having a transthyretin amyloid disease a therapeutically effective amount of a compound that prevents dissociation of a transthyretin tetramer by kinetic stabilization of the native state of the transthyretin tetramer.

In one embodiment, the invention features a method of treating a transthyretin amyloid disease, the method comprising administering to a subject diagnosed as having a transthyretin amyloid disease a therapeutically effective amount of a diflunisal analog (e.g., a diflunisal analog that prevents dissociation of a transthyretin tetramer) that prevents dissociation of a transthyretin tetramer. The diflunisal analog can optionally have reduced or absent NSAID activity (e.g., cyclooxygenase inhibitor activity) as compared to diflunisal.

In another embodiment, the invention features a method of treating a transthyretin amyloid disease, the method comprising administering to a subject diagnosed as having a transthyretin amyloid disease a therapeutically effective amount of a polychlorinated biphenyl (e.g., a polychlorinated biphenyl that prevents dissociation of a transthyretin tetramer) that prevents dissociation of a transthyretin tetramer. The polychlorinated biphenyl can be a hydroxylated polychlorinated biphenyl.

In another embodiment, the invention features a method of treating a transthyretin amyloid disease, the method comprising administering to a subject diagnosed as having a transthyretin amyloid disease a therapeutically effective amount of a benzoxazole (e.g., a benzoxazole that prevents dissociation of a transthyretin tetramer) that prevents dissociation of a transthyretin tetramer.

The transthyretin amyloid disease can be, for example, familial amyloid polyneuropathy, familial amyloid cardiomyopathy, or senile systemic amyloidosis.

The subject treated in the present methods can be a human subject, although it is to be understood that the principles of the invention indicate that the invention is effective with respect to all mammals. In this context, a "mammal" is understood to include any mammalian species in which treatment of diseases associated with transthyretin misfolding is desirable, particularly agricultural and domestic mammalian species.

The compounds described herein (e.g., biaryl compounds such as diflunisal analogs, polychlorinated biphenyls, or benzoxazoles) can be formulated with a pharmaceutically acceptable to prepare a pharmaceutical composition comprising the compound. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

The invention also encompasses the use of any of the compounds or pharmaceutical compositions described herein for the treatment of a transthyretin amyloid disease (e.g., familial amyloid polyneuropathy, familial amyloid cardiomyopathy, or senile systemic amyloidosis).

The invention also encompasses the use of any of the compounds or pharmaceutical compositions described herein in the manufacture of a medicament for the treatment of a transthyretin amyloid disease (e.g., familial amyloid polyneuropathy, familial amyloid cardiomyopathy, or senile systemic amyloidosis).

The compounds and treatment methods described herein provide significant advantages over the treatments options currently available for TTR amyloidosis. TTR amyloidosis typically leads to death in ten years, and until recently, was considered incurable. Liver transplantation is an effective means of replacing the disease-associated allele by a WT allele in familial cases because the liver is typically the source of amyloidogenic TTR. While liver transplantation is effective as a form of gene therapy it is not without its problems. Transplantation is complicated by the need for invasive surgery for both the recipient and the donor, long-term post-transplantation immunosuppressive therapy, a shortage of donors, its high cost, and the large number of TTR amyloidosis patients that are not good candidates because of their disease progression. Unfortunately, cardiac amyloidosis progresses in some familial patients even after liver transplantation because WT TTR often continues to deposit. Nor is central nervous system. (CNS) deposition of TTR relieved by transplantation owing to its synthesis by the choroid plexus. Transplantation is not a viable option for the most prevalent TTR disease, senile systemic amyloidosis (SSA), affecting approximately 25% of those over 80 due to the deposition of WT TTR.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
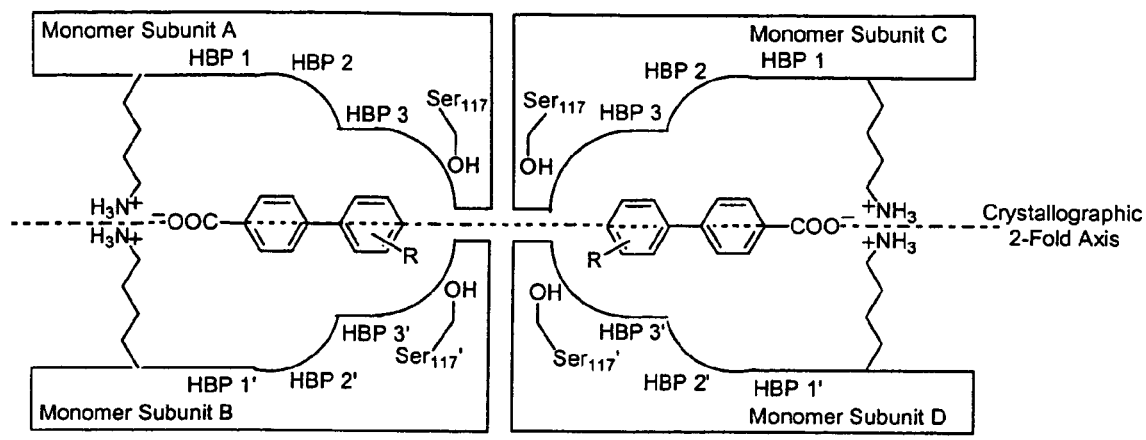
FIG. 1 is a schematic diagram depicting the T4 binding site of transthyretin.

At least some amyloid diseases appear to be caused by the deposition of any one of more than 20 nonhomologous proteins or protein fragments, ultimately affording a fibrillar cross-θ-sheet quaternary structure. Formation of amyloid fibrils from a normally folded protein like transthyretin requires protein misfolding to produce an assembly-competent intermediate. The process of transthyretin (TTR) amyloidogenesis appears to cause three different amyloid diseases—senile systemic amyloidosis (SSA), familial amyloid polyneuropathy (FAP) and familial amyloid cardiomyopathy (FAC). SSA is associated with the deposition of wild-type TTR, while FAP and FAC are caused by the amyloidogenesis of one of over 80 TTR variants. See, for example, Colon, W.; Kelly, J. W. *Biochemistry* 1992, 31, 8654-60; Kelly, J. W. *Curr. Opin. Struct. Biol.* 1996, 6, 11-7; Liu, K.; et al. *Nat. Struct. BioL* 2000, 7, 754-7; Westermark, P.; et al. *Proc. Natl. Acad. Sci. U.S.A.* 1990, 87, 2843-5; Saraiva, M. J.; et al. *J. Clin. Invest.* 1985, 76, 2171-7; Jacobson, D. R.; et al. *N. Engl. J. Med.* 1997, 336, 466-73; Buxbaum, J. N.; Tagoe, C. E. *Ann. Rev. Med.* 2000, 51, 543-569; and Saraiva, M. J. *Hum. Mutat.* 1995, 5, 191-6, each of which is incorporated by reference in its entirety.

TTR is a 55 kDa homotetramer characterized by 2,2,2 symmetry, having two identical funnel-shaped binding sites at the dimer-dimer interface, where thyroid hormone (T4) can bind in blood plasma and CSF. TTR is typically bound to less than 1 equiv of holo retinol binding protein. TTR misfolding including tetramer dissociation into monomers followed by tertiary structural changes within the monomer render the protein capable of misassembly, ultimately affording amyloid. The available treatment for FAP employs gene therapy mediated by liver transplantation to replace variant TTR in the blood with the wild type (WT) protein. This approach will likely not be effective for FAC due to the continued deposition of WT TTR, nor would it be useful for the treatment of SSA, where the process of WT TTR deposition appears to be causative. Liver transplantation therapy would also fail for approximately 10 of the TTR variants that deposit amyloid fibrils in the leptomeninges leading to CNS disease, as this TTR is synthesized by the choroid plexus. Hence, it is desirable to develop a general noninvasive drug-based therapeutic strategy. It can be desirable for the drug to be non-protein, non-peptide, or non-nucleic acid based. See, for example, Blake, C. C.; et al. *J. Mol. Biol.* 1978, 121, 339-56; Wojtczak, A.; et al. *Acta Crystallogr., Sect. D* 1996, 758-810; Monaco, H. L.; Rizzi, M.; Coda, A. *Science* 1995, 268, 1039-41; Lai, Z.; Colon, W.; Kelly, J. W. *Biochemistry* 1996, 35, 6470-82; Holmgren, G.; et al. *Lancet* 1993, 341, 1113-6; Suhr, O. B.; Ericzon, B. G.; Friman, S. *Liver Transpl.* 2002, 8, 787-94; Dubrey, S. W.; et al. *Transplantation* 1997, 64, 74-80; Yazaki, M.; et al. *Biochem. Biophys. Res. Commun.* 2000, 274, 702-6; and Cornwell, C. G. III; et al. *Am. J. of Med.* 1983, 75, 618-623, each of which is incorporated by reference in its entirety.

Synthesis of Diflunisal Analogs that Inhibit Transthyretin Amyloid Fibril Formation TTR misfolding leading to amyloid fibril formation can be prevented by T4-mediated stabilization of the tetramer. Several structurally diverse families of tetramer stabilizers bind to one or both T4 sites within TTR and prevent amyloidosis without the likely side effects of the hormone T4. These tetramer stabilizing compounds include several non-steroidal anti-inflammatory drugs (NSAIDS) such as flufenamic acid, diclofenac, flurbiprofen and diflunisal, that appear to function by increasing the kinetic barrier associated with tetramer dissociation through ground-state binding and stabilization. Because TTR is the secondary carrier of T4 in blood plasma, greater than 95% of TTR's T4 binding capacity remains unutilized, allowing for administration of tetramer stabilizing compound that target these sites. Because diflunisal is a cyclooxygenase-2 inhibitor long-term administration could lead to gastrointestinal side effects. Analogs of diflunisal that have reduced or absent NSAID activity, but possess high affinity for TTR in blood plasma, are therefore desirable. The first step toward this goal is the design and synthesis of diflunisal analogs as inhibitors of amyloid fibril formation. See, for example, Miroy, G. J.; et al. *Proc. Natl. Acad. Sci. U.S.A.* 1996, 93, 15051-6; Klabunde, T.; et al. *Nat. Struct. Biol.* 2000, 7, 312-21; Baures, P. W.; Peterson, S. A.; Kelly, J. W. *Bioorg. Med. Chem.* 1998, 6, 1389-401; Petrassi, H. M.; et al. *J. Am. Chem. Soc.* 2000, 122, 2178-2192; Baures, P. W.; et al. *Bioorg. Med. Chem.* 1999, 7, 1339-47; Sacchettini, J. C.; Kelly, J. W. *Nat. Rev. Drug Disc.* 2002, 1, 267-275; Oza, V. B.; et al. *J. Med. Chem.* 2002, 45, 321-32; Bartalena, L.; Robbins, J. *Clin. Lab. Med* 1993, 13, 583-98; Aldred, A. R.; Brack, C. M.; Schreiber, G. *Comp. Biochem. Physiol. B Biochem. Mol. Biol.* 1995, 111, 1-15; and Mao, H. Y.; et al. *J. Am. Chem. Soc.* 2001, 123, 10429-10435, each of which is incorporated by reference in its entirety.

The subunits of the TTR tetramer are related by three perpendicular $C_2$-axes. FIG. 1 is a schematic representation of the T4 binding site of TTR, demonstrating the forward binding mode where the inhibitor carboxylate participates in electrostatic interactions with the M-ammonium of Lys 15 and 15'. The two equivalent T4 binding sites created by the quaternary structural interface are interchanged by the two $C_2$ axes that are perpendicular to the crystallographic $C_2$ axis of symmetry. Each T4 binding site can be divided into an inner and outer binding cavity. See, for example, Blake, C. C.; Oatley, S. J. *Nature* 1977, 268, 115-20, which is incorporated by reference in its entirety. The inner binding cavity comprises a pair of halogen binding pockets (HBP), designated HBP 3 and 3', made up by the side chains of Leu 17, Ala 108, Val 121, and Thr 119. The convergence of four Ser 117 side chains from each subunit defines the innermost region and interface between the two identical binding sites. The Ser 117 hydroxyl groups can serve as hydrogen bond donors or acceptors to complimentary functionality on the compound (e.g., an inhibitor of amyloid formation) or mediate electrostatic interactions with the compound through water molecules. The outer binding site is composed of HBP 1 and 1', while HBP 2 and 2' are positioned at the interface of the inner and outer binding cavities. The Lys 15 and 15' M-ammonium groups define the very outer reaches of the outer binding cavity, allowing for electrostatic interactions with anionic substituents on a compound. Many of the TTR tetramer stabilizing compounds bind in the forward binding mode, where an anionic substituent on the hydrophilic phenyl ring positioned in the outer binding pocket engages in an electrostatic interaction with the Lys 15 M-ammonium groups. In the forward binding mode, a hydrophobic phenyl ring (often substituted with halogens) can occupy the inner binding pocket. Examples of binding in the opposite orientation (the reverse binding mode), however, have also been observed. In the reverse binding mode, a hydrophilic aromatic ring can be positioned in the inner cavity, allowing a carboxylate to hydrogen bond with Ser 117 and Ser 117'. In the reverse binding mode a halogen-substituted hydrophobic ring can be positioned in the outer cavity.

Diflunisal can reduce TTR acid-mediated amyloidogenesis. The structure of diflunisal (see Example 2) can be used as the basis for designing new compounds that can inhibit TTR amyloidogenesis. See, for example, Verbeeck, R. K.; et al. *Biochem. Pharm.* 1980, 29, 571-576; and Nuernberg, B.; Koehler, G.; Brune, K. *Clin. Pharmacokin.* 1991, 20, 81-89.

The compound can have the formula:

where $Ar^1$ is an aryl or heteroaryl group, $Ar^1$ being optionally substituted with one or more of: halo, —$R^1$, —$OR^1$, —OC(=O)$R^1$, —OC(=O)O$R^1$, —OC(=O)NH$R^1$, —S$R^1$, —S(=O)$R^1$, —S(=O)$_2R^1$, —C(=O)$R^1$, —CO$_2R^1$, —C(=O)NH$R^1$, —N$R^1R^2$, —NHC(=O)$R^1$, —NHC(=O)NH$R^1$, —NHC(=O)O$R^1$, or —NHS(=O)$_2R^1$.

$Ar^2$ is an aryl or heteroaryl group, $Ar^2$ being optionally substituted with one or more of: halo, —$R^1$, —$OR^1$, —OC(=O)$R^1$, —OC(=O)O$R^1$, —OC(=O)NH$R^1$, —S$R^1$, —S(=O)$R^1$, —S(=O)$_2R^1$, —C(=O)$R^1$, —CO$_2R^1$, —C(=O)NH$R^1$, —N$R^1R^2$, —NHC(=O)$R^1$, —NHC(=O)NH$R^1$, —NHC(=O)O$R^1$, or —NHS(=O)$_2R^1$.

Each $R^1$ is, independently, hydrogen, or a substituted or unsubstituted alkyl, cycloalkyl, heterocycloalkyl, alkenyl, cycloalkenyl, heterocycloalkenyl, alkynyl, aryl, or heteroaryl group.

Each $R^2$ is, independently, hydrogen, or a substituted or unsubstituted alkyl, cycloalkyl, heterocycloalkyl, alkenyl, cycloalkenyl, heterocycloalkenyl, alkynyl, aryl, or heteroaryl group.

In certain circumstances, $Ar^1$ can be substituted or unsubstituted phenyl. $Ar^2$ can independently be substituted or unsubstituted phenyl. $Ar^1$ and $Ar^2$ can simultaneously be substituted or unsubstituted phenyl. The substituents can be fluoro, chloro, hydroxy, —CO$_2$H, —CO$_2$Me, —OMe, —CH$_2$OH, or formyl. $R^1$ can be lower alkyl.

The compounds may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds can stabilize TTR tetramers and inhibit formation of TTR amyloid. The compounds can be analogs of diflunisal characterized by subtle structural changes. The compounds can be used to evaluate structure-activity relationships as they pertain to TTR amyloid inhibition. Substitution patterns and the number of substituents including halogens, carboxylates, acyl, alkoxy and hydroxyl can be varied. Structure-activity data from other classes of compounds reveal that a carboxylate substituent or analogous anionic or H-bonding group appears to be important, possibly participating in electrostatic interactions with the M-ammonium groups of Lys 15 and 15' or hydrogen bonding interactions with Ser 117 and 117', while the halogen-substituted hydrophobic ring compliments TTR's halogen binding pockets. Both fluorine and chlorine-substituted aryls can be evaluated, including 2-fluoro-, 4-fluoro-, 3,5-difluoro-, 2,4-difluoro- and 2,6-difluoro-. Iodine-substituted aryl groups may be less desirable due to their lability and potential for acting as thyroxine agonists. The carboxylate (anionic) substituent can be absent in some analogs to evaluate its influence on fibril inhibition and plasma binding selectivity. Compounds containing an aldehyde or alcohol functionality can be synthesized to evaluate the influence of a noncharged hydrogen bond acceptor or donor on binding selectivity and amyloid fibril inhibition. The gem-diol form of the aldehyde can be the principle binding species.

In general, the compounds can be synthesized by methods known in the art. One method of making the compounds is a Suzuki coupling:

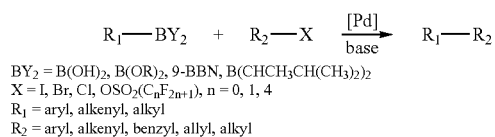

$BY_2 = B(OH)_2, B(OR)_2, 9\text{-}BBN, B(CHCH_3CH(CH_3)_2)_2$
$X = I, Br, Cl, OSO_2(C_nF_{2n+1}), n = 0, 1, 4$
$R_1 = $ aryl, alkenyl, alkyl
$R_2 = $ aryl, alkenyl, benzyl, allyl, alkyl For example, a biphenyl compound can be formed by a Suzuki coupling of a phenyl boronic acid with a bromobenzene or an iodobenzene. Appropriate protecting groups may be needed to avoid forming side products during the preparation of a compound. For example, an amino substituent can be protected by a suitable amino protecting group such as trifluoroacetyl or tert-butoxycarbonyl. Other protecting groups and reaction conditions can be found in T. W. Greene, *Protective Groups in Organic Synthesis*, (3rd, 1999, John Wiley & Sons, New York, N.Y.).

Pharmaceutical Compositions

The compounds described herein (e.g., diflunisal analogs, polychlorinated biphenyls, or benzoxazoles) may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques.

The pharmaceutical compositions can include any of the compounds, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant.

The pharmaceutical compositions may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

An effective amount of a pharmaceutical composition is the amount which is required to confer a therapeutic effect on the treated patient, and will depend on a variety of factors, such as the nature of the inhibitor, the size of the patient, the goal of the treatment, the nature of the pathology to be treated, the specific pharmaceutical composition used, and the judgment of the treating physician. For reference, see Freireich et al., *Cancer Chemother. Rep.* 1966, 50, 219 and Scientific Tables, Geigy Pharmaceuticals, Ardley; New York, 1970, 537. Dosage levels of between about 0.001 and about 100 mg/kg body weight per day, \ between about 0.1 and about 10 mg/kg body weight per day of the active ingredient compound may be useful.

The following are examples of the practice of the invention. They are not to be construed as limiting the scope of the invention in any way.

EXAMPLES

Example 1

Prevention of Transthyretin Amyloid Disease by Changing Protein Misfolding Energetics Hundreds of human diseases, including the amyloidoses, are associated with protein misfolding. The 80 familial mutations that exacerbate [for example, Val30→Met30 (V30M) and Leu55→Pro55 (L55P)] or ameliorate [Thr119→Met119 (T119M)] transthyretin (TTR) amyloid pathology provide valuable mechanistic insights. All disease-associated mutations characterized thus far destabilize the TTR tetramer, and many influence the velocity of rate-limiting tetramer dissociation, with rapid rates accelerating and slow rates retarding amyloidosis. We took advantage of the mechanism by which T119M prevents disease in V30M compound heterozygotes to develop small-molecule TTR amyloid inhibitors that dramatically slowed the initial misfolding event (tetramer dissociation) required for partial monomer denaturation, enabling misassembly into amyloid and other aggregates.

Hybrid tetramers were isolated to better understand the mechanism of trans-suppression. Increasing T119M subunit stoichiometry relative to V30M [or L55P] shifted the maximum for acid-mediated fibril formation to a lower pH, decreased the overall yield of amyloid at physiologically accessible pH's (>4.0), and slowed the rate of acid-induced (pH 4.4) and methanol-mediated amyloidogenesis. Several small-molecule TTR amyloid fibril inhibitors have been discovered, a subset of which were studied herein, including two drugs approved by the U.S. Food and Drug Administration (FDA) (inhibitors 8 and 10) (Sacchettini et al., Nature Rev. Drug Discovery 1, 267 (2002)). The influence of small-molecule inhibitor binding on the yield and rate of wild-type (WT) TTR fibril formation was similar to that of T119M subunit incorporation. However, the shift to a lower pH optimum for fibril formation was not observed with all the inhibitors. These inhibitors function by binding to the two equivalent thyroxine (T4) sites within the TTR tetramer, not the monomer.

Tetramer dissociation rates were measured by linking slow quaternary structural changes to the unfolding transition, with a rate of $5 \times 10^5$ times that of dissociation (Hammarström et al., Proc. Natl. Acad. Sci. U.S.A. 99, 16427 (2002)). Denaturation-detected dissociation is irreversible because the concentration of urea used (>6.0 M) cannot support refolding. Increasing T119M subunit stoichiometry relative to the V30M [or L55P] subunits revealed a dramatic TTR (1.8 μM) tetramer dissociation rate decrease (rate limiting for amyloidogenesis) in three different denaturing environments (acidic pH, aqueous methanol, or urea), explaining the origin of disease prevention.

Measurements of the WT TTR tetramer (1.8 μM) dissociation rate in the presence of inhibitors 6 through 10 (1.8 and 3.6 μM) showed dose-dependent slowing for all TTR-inhibitor complexes. The initial rate of tetramer dissociation was roughly inversely proportional to the mole fraction of the tetramer bound to two inhibitors (T·$I_2$). In the case of inhibitors 6, 7, and 9 (1.8 μM), the amplitude of the single exponential correlated primarily with dissociation of the unliganded tetramer (and, to a lesser extent, T·I), implying that T·$I_2$ prevented tetramer dissociation in 6 M urea. In contrast, formation of T·I and T·$I_2$ for inhibitors 8 and 10 did not protect the tetramer substantially from dissociation in urea, revealing that binding alone was insufficient. The efficient inhibition observed in the case of 6, 7, and 9 (3.6 μM) resulted from the binding energy stabilizing the T·$I_2$ complex by free energies exceeding 2.3 kcal/mol (Delta G1=RT ln([T·I]/[T])=RT ln([I]/Kd1) and Delta G2=RT ln([T·$I_2$]/[T])=RT ln {[I]2/ (Kd1*Kd2)). Stabilizing T·$I_2$ relative to T by 2.7 kcal/mol would translate to a two-order-of-magnitude decrease in the rate of TTR tetramer dissociation. The strong negatively cooperative binding of inhibitors 8 and 10 (3.6 μM) dictates that binding to the second site (T·$I_2$, μM dissociation constants) would not further stabilize TTR relative to binding to the first site (T·I). The nM dissociation constants (Kd1 and Kd2) of inhibitors 6, 7, and 9 would ensure that ground-state stabilization (>2.3 kcal/mol) would be sufficient to substantially increase the activation barrier for TTR tetramer dissociation, provided that the inhibitors did not bind to and similarly stabilize the dissociative transition state. The inhibitor dissociation rates from the T·I$_2$ and T·I complex could also play a role in the efficacy of inhibitors 6, 7, and 9. TTR saturated with inhibitor was immobilized by an antibody resin, over which aqueous buffer was passed at 5.0 ml/min to evaluate effective dissociation rates of 6 through 10. The best inhibitors were those with the lowest apparent dissociation rates.

Although there is generally a very good correlation between the amyloidogenesis rates (acidic conditions) and tetramer dissociation rates (in urea) in the presence of inhibitors, this need not be the case. Amyloidogenesis requires concentration-dependent misassembly after dissociation. Thus, small molecules will generally be more effective at preventing fibril formation than tetramer dissociation, especially when the inhibitor can keep the concentration of the monomeric amyloidogenic intermediate low (<3.6 µM), where fibril formation is very inefficient. Occasionally, tetramer dissociation rates measured in urea will not accurately predict the rank ordering of inhibitor efficacy under acidic conditions. For example, the FDA-approved drug diflunisal (8) was a much better amyloid inhibitor than a tetramer dissociation inhibitor. A likely explanation for this observation is that Kd1 and/or Kd2 are lower in acid than in urea (18). In addition, some inhibitors perform much better under denaturing conditions than their binding constants determined under physiological conditions would suggest. For example, compound 9 was more or equally efficient at preventing tetramer dissociation (urea) and fibril formation (acid) than was inhibitor 7, despite inhibitor 9 having Kd1 and Kd2 values that were 10 and 83 times that of 7, respectively (measured under physiological conditions). Thus, it is important to judge the efficacy of misfolding inhibitors under a variety of denaturing conditions and not just under physiological conditions.

Inclusion of T119M trans-suppressor subunits into tetramers otherwise composed of disease-associated subunits could decrease the rate of tetramer dissociation by stabilizing the tetrameric ground state to a greater extent than the transition state (as is the case with the small-molecule inhibitors) and/or by destabilizing the transition state of dissociation. To distinguish between these possibilities, we compared the reconstitution kinetics of WT and T119M homotetramers. Refolding of T119M monomers was rapid and within error of the folding rate of WT TTR monomers. However, reassembly of T119M folded monomers was two orders of magnitude slower than the tetramerization of WT TTR monomers initiated by urea dilution. The reassembly process is biphasic, which can be explained by the presence of an observable intermediate in the assembly pathway (probably a dimer). In the opposite direction, the T119M tetramer dissociates at ⅓₇ the rate exhibited by the WT TTR tetramer. These kinetic effects cannot be attributed to differences in tertiary structural stability and/or tetramer stability. A direct comparison of the thermodynamic stability of WT and T119M monomers (employing an engineered monomeric TTR construct (M-TTR)) revealed a difference in the free energy Delta Delta G for unfolding of only 0.4 kcal/mol, much less than the 2.1 and 2.7 kcal/mol required to explain the dissociation and assembly rate differences, respectively. A thermodynamic cycle analysis of T119M and WT TTR revealed that T119M prevents dissociation of the tetramer by destabilizing the dissociation transition state by approx 3.1 kcal/mol, not by tetramer stabilization. According to this analysis, the T119M tetramer is actually destabilized by 0.9 kcal/mol relative to WT, further supporting a kinetic stabilization mechanism. The free-energy difference between WT and T119M tetramer dissociation cannot be measured through urea-mediated unfolding because T119M denaturation in urea requires exceedingly long incubation periods (several weeks), during which TTR becomes modified. Comparisons of guanidinium chloride (GdmCl) and guanidinium thiocyanate (GdmSCN) denaturation curves revealed that WT TTR was more resistant to GdmCl denaturation than was T119M, whereas the opposite was true in GdmSCN. These differences in midpoints of denaturation can be attributed to differential anion stabilization, suggesting that the true thermodynamic stabilities of these proteins are very similar, although a quantitative analysis is not possible in these chaotropes.

T119M trans-suppression is principally mediated by destabilization of the dissociative transition state, consistent with positioning of T119M at the dimer-dimer interface. Increasing the dissociative transition-state energy by 3.1 kcal/mol effectively prevents tetramer dissociation because the activation barrier becomes insurmountable (dissociation half-life t½ increases from approx 42 hours to >1500 hours). Small-molecule binding similarly increases the activation barrier associated with tetramer dissociation in a dose-dependent fashion, although this is mediated through tetramer stabilization (relative to transition state stabilization). The extent of stabilization is maximal when the small-molecule dissociation constants Kd1 and Kd2 are as low as possible and the concentration of inhibitor is as high as possible. The concentrations used in our experiments for ground-state stabilization are comparable to those observed in plasma for numerous orally available drugs.

Small-molecule binding and trans-suppression increase the activation energy associated with tetramer dissociation, the rate-limiting step of TTR fibril formation. Establishing this analogy is important because it is known that trans-suppression prevents disease in V30M compound heterozygotes. Kinetic stabilization of the native state is a particularly attractive strategy, considering the emerging evidence that small misfolded oligomers are neurotoxic. Discovering small-molecule binders or developing a trans-suppression approach to tune the energy landscape of other pathologically relevant proteins with a predilection to misfold should now be considered.

Example 2

Diflunisal Analogs Stabilize the Native State of Transthyretin and are Inhibitors of Transthyretin Amyloid Fibril Formation Diflunisal (1) can reduce Transthyretin (TTR) amyloidogenesis. For example, under certain conditions (e.g., 3.6 TM TTR, 3.6 TM diflunisal, pH 4.4, 72 h, 37° C.), diflunisal reduces TTR amyloidogenesis by 63%. Under these conditions, doubling the diflunisal concentration (to 7.2 TM) reduces amyloidogenesis by 97%. Diflunisal is one of the better amyloid fibril inhibitors reported to date and orally administered diflunisal is highly bioavailable, affording a sustained plasma concentration exceeding 100 TM at a dose of 250 mg twice daily. Because diflunisal is a cyclooxygenase-2 inhibitor, long-term administration could lead to gastrointestinal side effects. Analogs of diflunisal that have reduced or absent NSAID activity, but possess high affinity for TTR in blood plasma, are therefore optionally desirable. The structure of diflunisal can thus be used as the basis for designing new compounds that can inhibit TTR amyloidogenesis. See, for example, Verbeeck, R. K.; et al. *Biochem. Pharm.* 1980, 29, 571-576; and Nuernberg, B.; Koehler, G.; Brune, K. *Clin. Pharmacokin.* 1991, 20, 81-89.

Diflunisal analogs were synthesized using a Pd-mediated Suzuki coupling between an aryl halide and an aryl boronic acid. The synthesis of analogs 2-10 was achieved by acetylation of either 3- or 4-iodophenol with acetic anhydride and pyridine, followed by Suzuki coupling with the appropriate fluorophenyl boronic acid under the standard Suzuki coupling reaction conditions, as shown in Scheme 1. Removal of the ester with $Na^0$ and MeOH (Zemplén conditions) provided phenols 2-10. See, for example, Miyaura, N.; Yanagi, T.; Suzuki, A. *Synth. Commun.* 1981, 11, 513-519; Sharp, M. J.; Snieckus, V. *Tetrahedron Lett.* 1985, 26, 5997-6000; Sharp, M. J.; Cheng W.; Snieckus, V. *Tetrahedron Lett.* 1987, 28, 5093-5096; Pozsgay, V.; Nanasi, P.; Neszmelyi, A. *Carbohydr. Res.* 1981, 90, 215-231; Jendralla, H.; Chen, L.-J. *Synthesis* 1990, 827-833; and Kelm, J.; Strauss, K. *Spectrochim. Acta, Part A* 1981, 37, 689-692, each of which is incorporated by reference in its entirety. *Acta, Part A* 1981, 37, 689-692, each of which is incorporated by reference in its entirety.

-continued

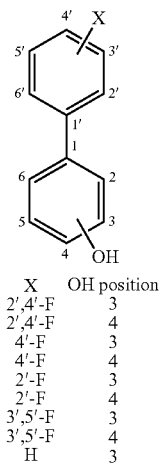

|  | X | OH position |
|---|---|---|
| 2 | 2',4'-F | 3 |
| 3 | 2',4'-F | 4 |
| 4 | 4'-F | 3 |
| 5 | 4'-F | 4 |
| 6 | 2'-F | 3 |
| 7 | 2'-F | 4 |
| 8 | 3',5'-F | 3 |
| 9 | 3',5'-F | 4 |
| 10 | H | 3 |

Diflunisal analog 11 was synthesized using solid-phase methods, as shown in Scheme 2. 3-iodobenzoic acid was coupled to Wang resin via an ester linkage, affording the resin-bound phenyliodide, which was then coupled to 2,4-difluorophenyl boronic acid, and cleaved from the resin with a 1:1 mixture of TFA:$CH_2Cl_2$. See, for example, Guiles, J. W.; Johnson, S. G.; Murray, W. V. *J. Org. Chem* 1996, 61, 5169-5171, which is incorporated by reference in its entirety.

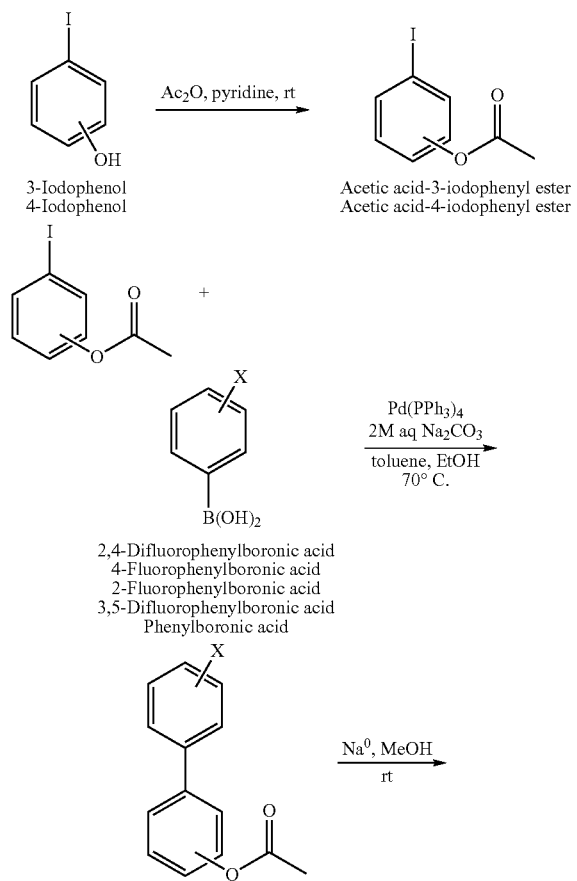

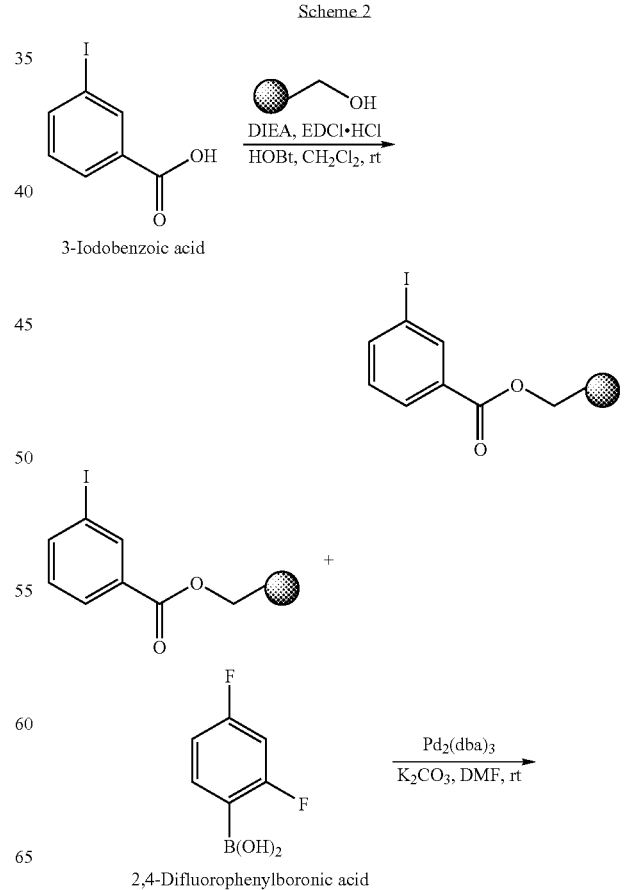

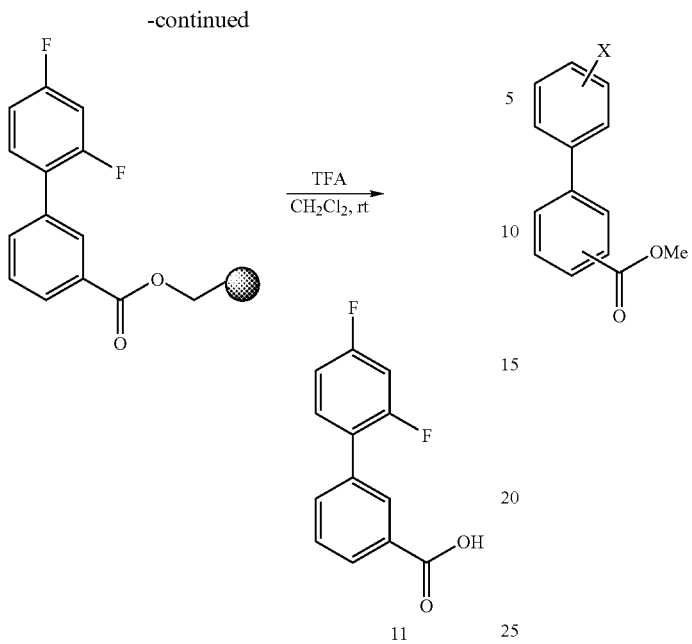

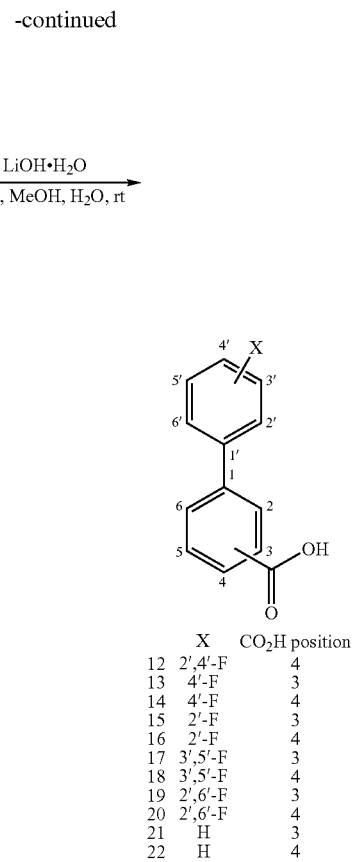

Carboxylate-containing substrates 12-22 were assembled by coupling of either methyl-3-bromobenzoate or methyl-4-bromobenzoate (both commercially available) with the appropriate fluorophenyl boronic acid utilizing standard Suzuki coupling conditions (see above), as shown in Scheme 3. The ester was then saponified with LiOH.H₂O to provide the corresponding carboxylate. See, for example, Bumagin, N. A.; Bykov, V. V. *Tetrahedron* 1997, 53, 14437-14450; Ananthakrishnanadar, P.; Kannan, N. *J. Chem. Soc., Perkin Trans.* 2 1982, 1305-1308; Homsi, F.; Nozaki, K.; Hiyama, T. *Tetrahedron Lett.* 2000, 41, 5869-5872; and Hajduk, P. J.; et al. *J. Med. Chem.* 1997, 40, 3144-3150, each of which is incorporated by reference in its entirety.

5-Iodosalicylic acid was esterfied using TMS-CH₂N₂, and the phenol was converted into a methyl ether employing MeI. The protected salicylic acid was coupled with the various fluorophenyl boronic acids, and subsequently deprotected by LiOH.H₂O saponification and BBr₃ demethylation to provide salicyclic acid derivatives 23-27, as shown in Scheme 4. See, for example, Nicolaou, K. C.; et al. *Chem. Eur. J.* 1999, 5, 2602-2621; and Chu-Moyer, M. Y.; et al. *J. Med. Chem.* 2002, 45, 511-528.

Scheme 3

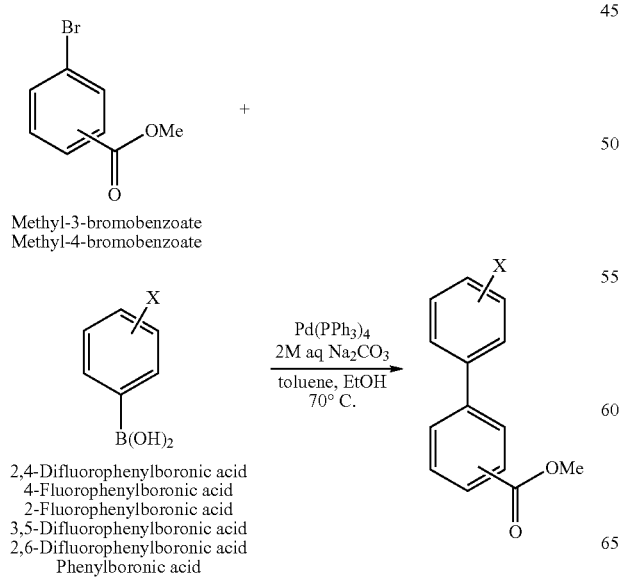

Scheme 4

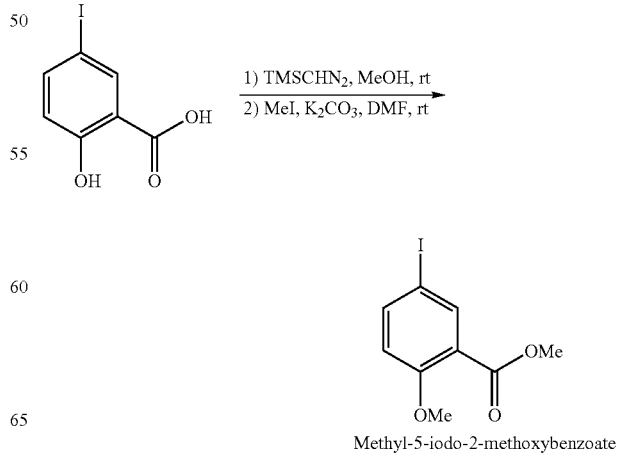

-continued

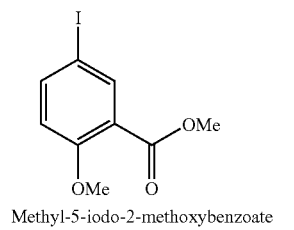
Methyl-5-iodo-2-methoxybenzoate

+

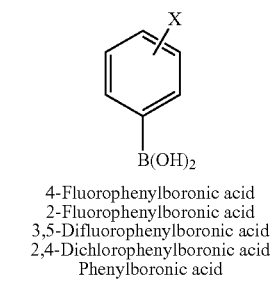
4-Fluorophenylboronic acid
2-Fluorophenylboronic acid
3,5-Difluorophenylboronic acid
2,4-Dichlorophenylboronic acid
Phenylboronic acid Pd(PPh$_3$)$_4$
2M aq Na$_2$CO$_3$
———————
toluene, EtOH
70° C.

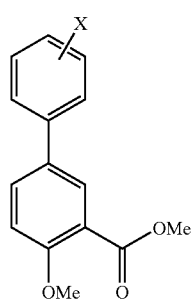

1) BBr$_3$, CH$_2$Cl$_2$
  -78° C.
2) LiOH•H$_2$O
  THF, MeOH,
  H$_2$O, rt

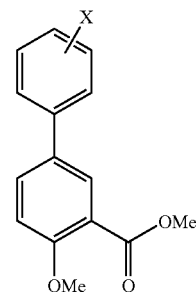

| | X |
|---|---|
| 23 | 4'-F |
| 24 | 2'-F |
| 25 | 3',5'-F |
| 26 | 2',4'-Cl |
| 27 | H |

3',5'-Dihalo-4'-hydroxy-containing analogs 28-31 were synthesized by first protecting the commercially available bromophenol as the methyl ether (MeI and K$_2$CO$_3$). Suzuki coupling with a (methoxycarbonylphenyl) boronic acid resulted in the formation of the fully protected biphenyl substrates. BBr$_3$-mediated methyl ether cleavage and saponification with LiOH.H$_2$O provided the fully functionalized diflunisal analogs 28-31, as shown in Scheme 5.

Scheme 5

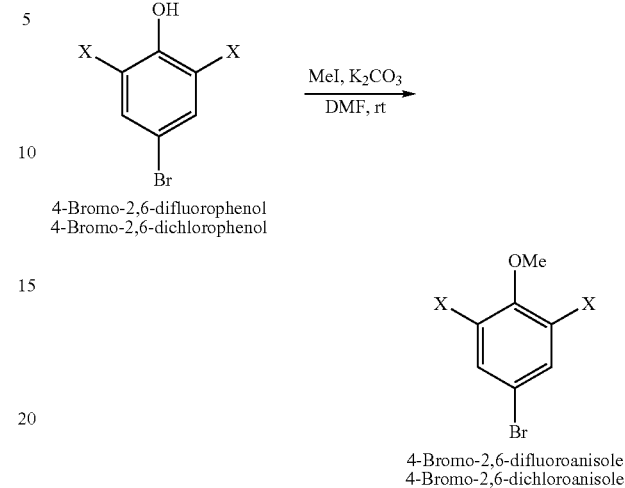
4-Bromo-2,6-difluorophenol
4-Bromo-2,6-dichlorophenol

MeI, K$_2$CO$_3$
———————
DMF, rt

4-Bromo-2,6-difluoroanisole
4-Bromo-2,6-dichloroanisole

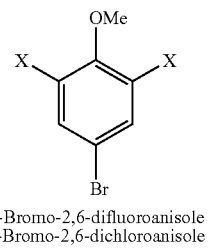
4-Bromo-2,6-difluoroanisole
4-Bromo-2,6-dichloroanisole

+

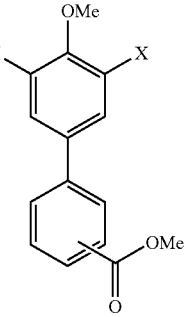
(3-Methoxycarbonylphenyl) boronic acid
(4-Methoxycarbonylphenyl) boronic acid Pd(PPh$_3$)$_4$
2M aq Na$_2$CO$_3$
———————
toluene, EtOH
70° C.

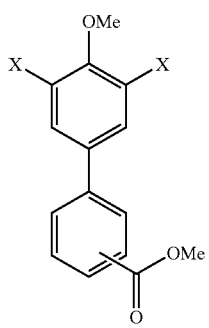

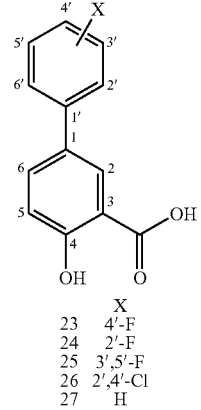

1) BBr$_3$, CH$_2$Cl$_2$
  -78° C.
2) LiOH•H$_2$O
  THF, MeOH,
  H$_2$O, rt

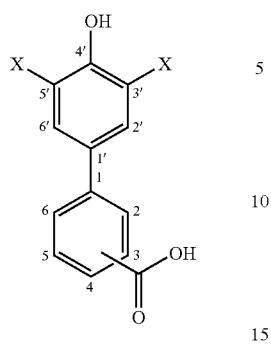

| | X | CO$_2$H position |
|---|---|---|
| 28 | F | 3 |
| 29 | F | 4 |
| 30 | Cl | 3 |
| 31 | Cl | 4 |

Methyl ether and methyl ester analogs of diflunisal were synthesized by esterification of the carboxylic acid with TMS-diazomethane to provide 32, optionally followed by etherification with MeI and K$_2$CO$_3$ and ester hydrolysis with LiOH.H$_2$O to afford 33. See Scheme 6.

Scheme 6

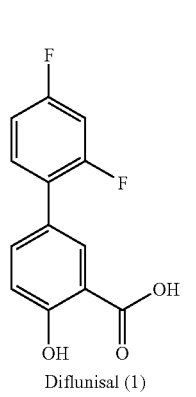
Diflunisal (1)

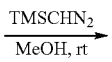
TMSCHN$_2$ / MeOH, rt

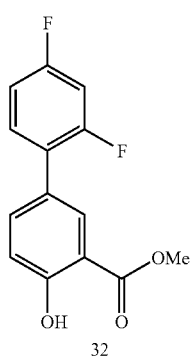
32

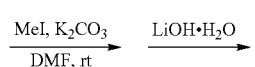
MeI, K$_2$CO$_3$ / DMF, rt     LiOH·H$_2$O

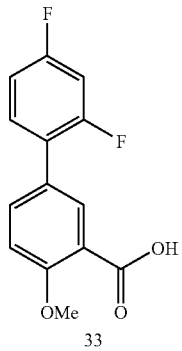
33

A series of halogenated biphenyls 34-38 were assembled by Suzuki coupling of iodobenzene with a series of halogen-containing boronic acids, as shown in Scheme 7. See, for example, Patrick, T. B.; Willaredt, R. P. DeGonia, D. J. *J. Org. Chem.* 1985, 50, 2232-2235; Kuchar, M.; et al. *Collection of Czechoslovak Chemical Communications* 1988, 53, 1862-1872; Allen, K. J.; Bolton, R.; Williams, G. H. *J. Chem. Soc., Perkin Trans.* 2 1983, 691-695; Nakada, M.; et al. *Bull. Chem. Soc. Jpn.* 1989, 62, 3122-3126; and Weingarten, H. *J. Org. Chem.* 1961, 26, 730-733, each of which is incorporated by reference in its entirety.

Scheme 7

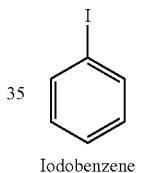
Iodobenzene

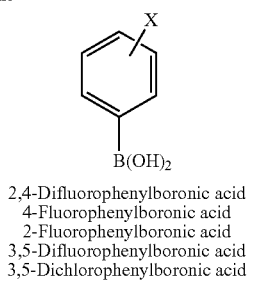
B(OH)$_2$ 2,4-Difluorophenylboronic acid
4-Fluorophenylboronic acid
2-Fluorophenylboronic acid
3,5-Difluorophenylboronic acid
3,5-Dichlorophenylboronic acid Pd(PPh$_3$)$_4$
2M aq Na$_2$CO$_3$
toluene, EtOH
70° C.

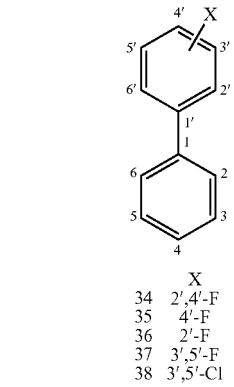

| | X |
|---|---|
| 34 | 2',4'-F |
| 35 | 4'-F |
| 36 | 2'-F |
| 37 | 3',5'-F |
| 38 | 3',5'-Cl |

Chlorinated biaryl aldehydes were assembled using 3,5-dichloroiodobenzene and either 2-, 3- or 4-formylphenyl boronic acid, as shown in Scheme 8. Aldehydes 42-44, lacking the halogen substitution, were prepared analogously. Aldehydes 39-41 were either oxidized with $KMnO_4$ in acetone/water to provide the corresponding carboxylic acids 45-47 or reduced with $NaBH_4$ in MeOH to provide the corresponding benzyl alcohols 48-50, Scheme 8. Reduction of the non-chlorinated aldehydes 42-44 with $NaBH_4$ and MeOH produced the biphenyl benzylic alcohols 51-53. See, for example, Song, X. P.; He, H. T.; Siahaan, T. *J. Org. Lett.* 2002, 4, 549-552; and Nicolaou, K. C.; et al. *J. Am. Chem. Soc.* 2001, 123, 9313-9323; Hashizume, H.; et al. *Chem. Pharm. Bull.* 1994, 42, 512-520; Indolese, A. F. *Tetrahedron Lett.* 1997, 38, 3513-3516; Pridgen, L. N.; Snyder, L.; Prol, J. *J. Org. Chem.* 1989, 54, 1523-1526; Huang, C. G.; Beveridge, K. A.; Wan, P. *J. Am. Chem. Soc.* 1991, 113, 7676-7684; Wendeborn, S.; et al. *Synlett.* 1998, 6, 671-675; Stevens, C. V.; Peristeropoulou, M.; De Kimpe, N. *Tetrahedron* 2001, 57, 7865-7870; Tanaka, K.; Kishigami, S.; Toda, F. *J. Org. Chem.* 1990, 55, 2981-2983; and Clive, D. L. J.; Kang, S. Z. *J. Org. Chem.* 2001, 66, 6083-6091, each of which is incorporated by reference in its entirety.

Scheme 8

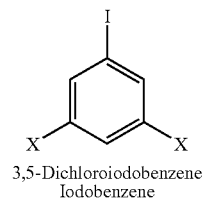

3,5-Dichloroiodobenzene
Iodobenzene

+

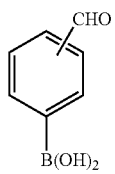

3-Formylphenylboronic acid
4-Formylphenylboronic acid
2-Formylphenylboronic acid
Phenylboronic acid $\xrightarrow{\begin{array}{c}Pd(PPh_3)_4\\2M\ aq\ Na_2CO_3\\\hline\text{toluene, EtOH}\\70°\ C.\end{array}}$

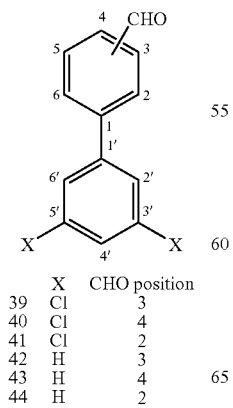

| | X | CHO position |
|---|---|---|
| 39 | Cl | 3 |
| 40 | Cl | 4 |
| 41 | Cl | 2 |
| 42 | H | 3 |
| 43 | H | 4 |
| 44 | H | 2 |

-continued

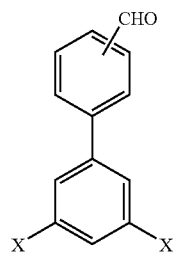 $\xrightarrow{\begin{array}{c}KMnO_4\\\hline\text{acetone, rt}\end{array}}$ 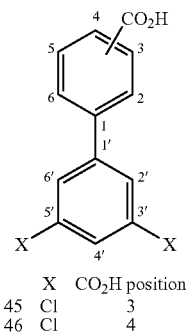

| | X | $CO_2H$ position |
|---|---|---|
| 45 | Cl | 3 |
| 46 | Cl | 4 |
| 47 | Cl | 2 |

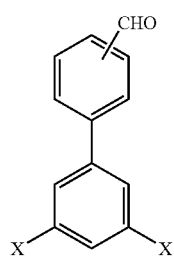 $\xrightarrow{\begin{array}{c}NaBH_4\\\hline\text{MeOH, rt}\end{array}}$ 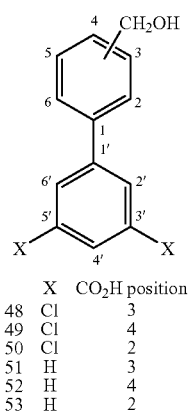

| | X | $CO_2H$ position |
|---|---|---|
| 48 | Cl | 3 |
| 49 | Cl | 4 |
| 50 | Cl | 2 |
| 51 | H | 3 |
| 52 | H | 4 |
| 53 | H | 2 |

3',5'-Difluoroformyl-functionalized biphenyls 54 and 55 were synthesized via Suzuki coupling of 3,5-difluorophenyl boronic acid with either 2- or 3-iodobenzaldehyde, as shown in Scheme 9. All other inhibitors were synthesized by similar methods and reported previously. Compounds 10, 21, 35, 36 and 43 are commercially available.

Scheme 9

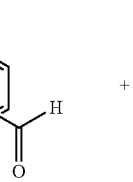

3-Iodobenzaldehyde
4-Iodobenzaldehyde

+

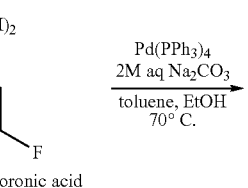

3,5-Difluorophenylboronic acid $\xrightarrow{\begin{array}{c}Pd(PPh_3)_4\\2M\ aq\ Na_2CO_3\\\hline\text{toluene, EtOH}\\70°\ C.\end{array}}$ -continued

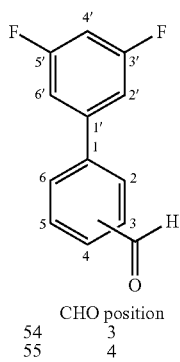

| | CHO position |
|---|---|
| 54 | 3 |
| 55 | 4 |

Reagents and solvents were purchased from Aldrich, Lancaster, Acros, Combi-Blocks, Matrix and Pfaltz-Bauer. THF and CH$_2$Cl$_2$ were dried by passage over Al$_2$O$_3$. Other solvents and reagents were obtained from commercial suppliers and were used without further purification unless otherwise noted. Reactions were monitored by analytical thin layer chromatography (TLC) on silica gel 60 F$_{254}$ pre-coated plates with fluorescent indicator purchased from EM Science. Visualization of the TLC plates was accomplished by UV illumination, phosphomolybdic acid treatment followed by heat or ceric ammonium molybdate treatment followed by heat. Flash chromatography was performed using silica gel 60 (230-400 mesh) from EM Science. The purity of new compounds that were essential to the conclusions drawn in the text were determined by HPLC. Normal phase HPLC was performed with a Waters 600 pump/controller, a Waters 996 photodiode array detector and a Waters NovaPak silica column. The solvent system employed was hexanes and ethyl acetate, and gradients were run from 50:50 hexanes:ethyl acetate to 0:100 hexanes:ethyl acetate over 30 min. Reverse phase HPLC was performed with a Waters 600 pump/controller, a Waters 2487 dual wavelength detector and a Vydac protein and peptide C18 column. Solvent system A was 95:5 water:acetonitrile with 0.5% trifluoroacetic acid and solvent B was 5:95 water:acetonitrile with 0.5% trifluoroacetic acid. Gradients were run from 100:0 A:B to 0:100 A:B over 20 min with a hold at 100% B for an additional 10 min. Circular dichroism spectroscopy was performed on an AVIV Instruments spectrometer, model 202SF. NMR spectra were recorded on a Varian FT NMR spectrometer at a proton frequency of 400 MHz. Proton chemical shifts are reported in parts per million (ppm) with reference to CHCl$_3$ as the internal chemical shift standard (7.26 ppm) unless otherwise noted. Coupling constants are reported in hertz (Hz). Carbon chemical shifts are reported in parts per million (ppm) with reference to CDCl$_3$ as the chemical shift standard (77.23 ppm) unless otherwise noted. All mass spectra were obtained at The Scripps Research Institute Center for Mass Spectrometry or the University of Illinois Mass Spectrometry Laboratory.

Compounds 2-10 were prepared according to Scheme 1. To a solution of the appropriate acetic acid-iodophenyl ester (1.0 equiv) dissolved in enough toluene to give a concentration of 0.05 M, was added a solution of phenyl boronic acid (1.1 equiv) dissolved in EtOH to give a 0.6 M solution with respect to the boronic acid. A 2 M aqueous solution of Na$_2$CO$_3$ was added to give a final reaction concentration of 0.03 M with respect to the acetic acid-iodophenyl ester, followed by addition of Pd(PPh$_3$)$_4$ (4.0 mol %). The reaction was heated to reflux under Ar for 20 h, and upon completion, was cooled to rt and extracted with CH$_2$Cl$_2$ (2×), washed with brine (1×), dried over MgSO$_4$ and concentrated in vacuo. The residue was purified by flash chromatography (10:1 hexane:ethyl acetate) to afford the acetylated biphenyl.

A catalytic amount of Na$^0$ was added to a solution of the acetylated biphenyl in MeOH to provide a final reaction concentration of 0.3 M. The reaction was allowed to stir at rt under Ar for 12 h, after which Dowex 50W-X8 cation exchange resin was added to neutralize the reaction mixture. The resin was filtered and the filtrate was concentrated in vacuo and flash chromatographed (3:1 hexane:ethyl acetate) to afford the hydroxybiphenyl products as white solids in 22-75% yields.

2',4'-Difluorobiphenyl-3-ol (2). $^1$H NMR (DMSO-d$_6$, 400 MHz) δ 9.63 (br s, 1H), 7.54 (td, 1H, J=8.9, 6.7 Hz), 7.34 (ddd, 1H, J=11.1, 9.2, 2.6 Hz), 7.27 (m, 1H), 7.17 (tdd, 1H, J=8.3, 2.6, 1.2 Hz), 6.92 (m, 2H), 6.81 (ddd, 1H, J=8.1, 2.5, 1.0 Hz). $^{13}$C NMR (DMSO-d$_6$, 100 MHz) δ 162.8, 160.3, 157.4, 135.4, 131.8, 129.7, 119.4, 115.6, 114.9, 111.9, 104.4. HRESIMS calculated for C$_{12}$H$_8$F$_2$O (M–H) 205.0466. found 205.0465. Normal phase HPLC retention time: 10.5 min. Reverse phase HPLC retention time: 1.3 min. >99% pure.

2',4'-Difluorobiphenyl-4-ol (3). $^1$H NMR (DMSO-d$_6$, 400 MHz) δ 7.49 (td, 1H, J=9.4, 8.6 Hz), 7.34 (AA'XX', 2H, J$_{AA'}$=J$_{XX'}$=2.5 Hz, J$_{XA}$=8.7 Hz, J$_{X'A'}$=8.5 Hz, J$_{X'A}$=0.3 Hz, J$_{XA'}$=0.3 Hz, ν$_A$=ν$_{A'}$=2934.1 Hz, ν$_X$=ν$_{X'}$=2746.2 Hz), 7.28 (ddd, 2H, J=11.3, 9.4, 2.6 Hz), 7.13 (dddd, 1H, J=8.3, 7.5, 2.8, 1.0 Hz), 6.87 (AA'XX', 2H, as above). $^{13}$C NMR (DMSO-d$_6$, 100 MHz) δ 162.3, 160.0, 157.2, 131.4, 129.9, 124.8, 115.4, 111.8, 104.3. HRESIMS calculated for C$_{12}$H$_8$F$_2$O (M–H) 205.0464. found 205.0465. Normal phase HPLC retention time: 11.2 min. Reverse phase HPLC retention time: 12.6 min. >98% pure.

3',5'-Difluorobiphenyl-3-ol (8). $^1$H NMR (DMSO-d$_6$, 400 MHz) δ 9.65 (br s, 1H), 7.34 (m, 2H), 7.28 (t, 1H, J=7.9 Hz), 7.19 (tt, 1H, J=9.1, 2.2 Hz), 7.13 (ddd, 1H, J=7.8, 1.8, 1.0 Hz), 7.08 (t, 1H, J=2.1 Hz), 6.86 (ddd, 1H, J=8.0, 2.4, 1.0 Hz). $^{13}$C NMR (DMSO-d$_6$, 100 MHz) δ 162.9, 158.0, 144.1, 139.1, 130.1, 117.6, 115.7, 109.7, 102.6. HRESIMS calculated for C$_{12}$H$_8$F$_2$O (M–H) 205.0465. found 205.0468. Normal phase HPLC retention time: 11.4 min. Reverse phase HPLC retention time: 12.9 min. >99% pure.

3',5'-Difluorobiphenyl-4-ol (9). $^1$H NMR (CDCl$_3$, 400 MHz) δ 7.44 (AA'XX', 2H, J$_{AA'}$=J$_{XX'}$=3.0 Hz, J$_{XA}$=8.0 Hz, J$_{X'A'}$=8.5 Hz, J$_{X'A}$=0.7 Hz, J$_{XA'}$=0.5 Hz, ν$_A$=ν$_{A'}$=2973.8 Hz, ν$_X$=ν$_{X'}$=2766.4 Hz), 7.05 (dtd, 2H, J=6.6, 2.4, 0.7 Hz), 6.92 (AA'XX', 2H, as above), 6.74 (tt, 1H, J=8.9, 2.4 Hz), 5.11 (s, 1H). $^{13}$C NMR (CDCl$_3$, 100 MHz) δ 164.7, 156.1, 144.2, 131.8, 128.6, 116.1, 109.6, 102.1. HRESIMS calculated for C$_{13}$H$_8$Cl$_2$O$_2$ (M–H) 205.0465. found 205.0465. Normal phase HPLC retention time: 10.8 min. Reverse phase HPLC retention time: 12.9 min. >99% pure.

2',4'-Difluorobiphenyl-3-carboxylic acid (11). Compound 11 was prepared according to Scheme 2. 3-Iodobenzoic acid (200 mg, 0.81 mmol), DIEA (140 TL, 0.81 mmol), EDCI.HCl and HOBt were added to a solution of Wang resin (265 mg, 0.67 mmol, 2.53 mmol/g) swelled in CH$_2$Cl$_2$ (10 mL). After rigorous shaking on a peptide shaker for 22 h at rt, the solvent was removed and the resin was washed with DMF (3×10 mL) and CH$_2$Cl$_2$ (3×10 mL) and dried thoroughly in vacuo.

2,4-Difluorophenyl boronic acid (112 mg, 0.71 mmol), K$_2$CO$_3$ (98 mg, 0.71 mmol) and Pd$_2$(dba)$_3$ (4 mg, 0.01 mmol) were added to a solution of functionalized Wang resin (140 mg, 0.35 mmol) swelled in DMF (2 mL). After stirring at rt, the reaction was filtered and the resin was washed with DMF (3×), H$_2$O (3×), CH$_2$Cl$_2$ (3×) and MeOH (3×) and dried thoroughly in vacuo.

A solution of TFA:CH$_2$Cl$_2$ (3 mL 1:1) was added to functionalized resin (140 mg, 0.35 mmol) and shaken vigorously on a peptide shaker for 13 h at rt. After completion, the reaction was filtered, the resin was washed with CH$_2$Cl$_2$ (3×), the filtrate was concentrated in vacuo and purified by flash chromatography (2:1 hexane:ethyl acetate, 0.5% acetic acid) to afford 11 (81 mg, 100%) as a white solid. $^1$H NMR (DMSO-d$_6$, 400 MHz) δ 13.19 (br s, 1H), 8.07 (q, 1H, J=1.7 Hz), 7.99 (dt, 1H, J=7.9, 1.6 Hz), 7.78 (dq, 1H, J=7.8, 1.3 Hz), 7.64 (m, 2H), 7.40 (ddd, 1H, J=11.1, 8.8, 2.5 Hz), 7.22 (tdd, 1H, J=8.4, 2.8, 1.0 Hz). $^{13}$C NMR (DMSO-d$_6$, 100 MHz) δ 167.0, 160.7, 160.4, 134.5, 133.0, 132.0, 131.3, 129.4, 129.1, 128.7, 123.9, 112.2, 104.6. HRESIMS calculated for C$_{13}$H$_8$F$_2$O$_2$ (M−H) 233.0414. found 233.0426. Normal phase HPLC retention time: 13.7 min. Reverse phase HPLC retention time: 12.5 min. >99% pure.

Compounds 12-22 were prepared according to Scheme 3. To a solution of the appropriate methyl bromobenzoate (1.0 equiv) dissolved in enough toluene to give a concentration of 0.1 M, was added a solution of phenyl boronic acid (2.0 equiv) dissolved in EtOH to give a 1.0 M solution of boronic acid. A 2 M aqueous solution of Na$_2$CO$_3$ was added to give a final reaction concentration of 0.06 M with respect to the bromobenzoate, followed by addition of Pd(PPh$_3$)$_4$ (10.0 mol %). The reaction was stirred at 70° C. under Ar for 25 h, and upon completion, was cooled to rt and extracted with CH$_2$Cl$_2$ (2×), washed with brine (1×), dried over MgSO$_4$ and concentrated in vacuo. The residue was purified by flash chromatography (10:1 hexane:ethyl acetate) to afford the methyl ester.

To a solution of methyl ester (1.0 equiv) in THF:MeOH:H$_2$O (1:1:1) at a concentration of 0.06 M, was added LiOH.H$_2$O (3.0 equiv). The reaction was stirred at rt for 4 h, and upon completion, was acidified with 30% HCl, extracted with ethyl acetate (3×5 mL), dried over MgSO$_4$ and concentrated in vacuo. The residue was purified by flash chromatography (CH$_2$Cl$_2$, 1% MeOH, 0.2% acetic acid) to afford the biphenyl carboxylic acids as white solids in 6-93% yields.

2',4'-Difluorobiphenyl-4-carboxylic acid (12). $^1$H NMR (DMSO-d$_6$, 400 MHz) δ 13.09 (br s, 1H), 8.04 (AA'XX', 2H, $J_{AA'}$=$J_{XX'}$=2.0 Hz, $J_{XA}$=$J_{X'A'}$=8.0 Hz, $J_{X'A}$=$J_{XA'}$=0.7 Hz, $v_A$=$v_{A'}$=3213.3 Hz, $v_X$=$v_{X'}$=3056.2 Hz), 7.65 (AA'XX', 2H, as above), 7.63 (m, 1H), 7.38 (ddd, 1H, J=11.2, 9.0, 2.8 Hz), 7.21 (td, 1H, J=8.4, 2.2 Hz). $^{13}$C NMR (DMSO-d$_6$, 100 MHz) δ 167.1, 160.8, 158.0, 138.6, 132.1, 130.1, 129.6, 129.2, 123.9, 112.2, 104.7. HRESIMS calculated for C$_{13}$H$_8$F$_2$O$_2$ (M−H) 233.0414. found 233.0407. Normal phase HPLC retention time: 13.3 min. Reverse phase HPLC retention time: 12.6 min. >99% pure.

2'-Fluorobiphenyl-3-carboxylic acid (15). $^1$H NMR (CD$_3$OD, 400 MHz) δ 8.18 (q, 1H, J=1.4 Hz), 8.03 (dt, 1H, J=7.8, 1.3 Hz), 7.76 (dq, 1H, J=7.7, 1.5 Hz), 7.55 (t, 1H, J=7.8 Hz), 7.48 (td, 1H, J=7.8, 1.7 Hz), 7.38 (dddd, 1H, J=8.3, 7.5, 5.1, 1.8 Hz), 7.26 (td, 1H, J=7.6, 1.3 Hz), 7.20 (ddd, 1H, J=11.0, 8.2, 1.2 Hz). $^{13}$C NMR (CD$_3$OD, 100 MHz) δ 169.7, 161.2, 137.5, 134.6, 132.4, 132.0, 131.3, 130.1, 129.9, 129.5, 126.0, 117.2. HRESIMS calculated for C$_{13}$H$_9$FO$_2$ (M−H) 215.0508. found 215.0498. Normal phase HPLC retention time: 10.6 min. Reverse phase HPLC retention time: 12.1 min. >99% pure.

2'-Fluorobiphenyl-4-carboxylic acid (16). $^1$H NMR (DMSO-d$_6$, 400 MHz) δ 13.10 (br s, 1H), 8.05 (AA'XX', 2H, $J_{AA'}$=$J_{XX'}$=1.7 Hz, $J_{XA}$=$J_{X'A'}$=8.5 Hz, $J_{X'A}$=$J_{XA'}$=0.3 Hz, $v_A$=$v_{A'}$=3217.9 Hz, $v_X$=$v_{X'}$=3070.0 Hz), 7.67 (AA'XX', 2H, as above), 7.58 (td, 1H, J=8.0, 1.8 Hz), 7.34 (m, 1H). $^{13}$C NMR (DMSO-d$_6$, 100 MHz) δ 167.1, 159.1, 139.4, 130.8, 130.3, 130.2, 129.6, 129.0, 127.3, 125.1, 116.2. HRESIMS calculated for C$_{13}$H$_9$FO$_2$ (M−H) 215.0508. found 215.0515.

Normal phase HPLC retention time: 12.3 min. Reverse phase HPLC retention time: 12.2 min. >99% pure.

3',5'-Difluorobiphenyl-3-carboxylic acid (17). $^1$H NMR (acetone-d$_6$, 400 MHz) δ 8.30 (td, 1H, J=2, 0.5 Hz), 8.10 (dtd, 1H, J=7.6, 1.1, 0.5 Hz), 7.97 (ddd, 1H, J=7.8, 2.0, 1.1 Hz ), 7.64 (td, 1H, J=7.8, 0.6 Hz), 7.39 (m, 2H), 7.06 (tt, 1H, J=9.3, 2.4 Hz). $^{13}$C NMR (acetone-d$_6$, 100 MHz) δ 167.4, 165.6, 163.2, 144.6, 139.8, 132.5, 132.4, 130.6, 130.3, 128.9, 111.0, 103.7. HRESIMS calculated for C$_{13}$H$_8$F$_2$O$_2$ (M−H) 233.0414. found 233.0425. Normal phase HPLC retention time: 13.5 min. Reverse phase HPLC retention time: 12.7 min. >99% pure.

3',5'-Difluorobiphenyl-4-carboxylic acid (18). $^1$H NMR (DMSO-d$_6$, 400 MHz) δ 13.15 (br s, 1H), 8.02 (d, 2H, J=8.2 Hz), 7.85 (d, 2H, J=8.5 Hz), 7.49 (m, 2H), 7.26 (tt, 1H, J=9.4, 2.4 Hz). $^{13}$C NMR (DMSO-d$_6$, 100 MHz) δ 166.4, 164.1, 161.7, 142.6, 141.6, 130.9, 130.0, 127.1, 110.2, 103.5. HRESIMS calculated for C$_{13}$H$_8$F$_2$O$_2$ (M−H) 233.0414. found 233.0423. Normal phase HPLC retention time: 13.0 min. Reverse phase HPLC retention time: 12.8 min. >99% pure.

2',6'-Difluorobiphenyl-3-carboxylic acid (19). $^1$H NMR (DMSO-d$_6$, 400 MHz) δ 8.03 (dt, 1H, J=7.8, 1.6 Hz), 8.00 (m, 1H), 7.72 (dt, 1H, J=7.8, 1.4 Hz), 7.64 (t, 1H, J=7.7 Hz), 7.53 (m, 1H), 7.26 (t, 2H, J=8.3 Hz). $^{13}$C NMR (DMSO-d$_6$, 100 MHz) δ 167.7, 158.7, 135.0, 132.2, 131.4, 131.1, 129.9, 129.5, 129.5, 112.8, 110.9. HRESIMS calculated for C$_{13}$H$_8$F$_2$O$_2$ (M−H) 233.0414. found 233.0410. Normal phase HPLC retention time: 12.1 min. Reverse phase HPLC retention time: 12.1 min. >97% pure.

2',6'-Difluorobiphenyl-4-carboxylic acid (20). $^1$H NMR (DMSO-d$_6$, 400 MHz) δ 8.06 (AA'XX', 2H, $J_{AA'}$=$J_{XX'}$=2.0 Hz, $J_{XA}$=$J_{X'A'}$=8.0 Hz, $J_{X'A}$=$J_{XA'}$=0.7 Hz, $v_A$=$v_{A'}$=3243.6 Hz, $v_X$=$v_{X'}$=3018.6 Hz), 7.60 (AA'XX', 2H, as above), 7.54 (m, 1H), 7.27 (t, 2H), J=8.3 Hz). $^{13}$C NMR (DMSO-d$_6$, 100 MHz) δ 171.0, 164.0, 134.1, 125.7, 122.0, 121.9, 121.1, 103.4. HRESIMS calculated for C$_{13}$H$_8$F$_2$O$_2$ (M−H) 233.0414. found 233.0425. Normal phase HPLC retention time: 14.5 min. Reverse phase HPLC retention time: 12.1 min. >99% pure.

Biphenyl-4-carboxylic acid (22). $^1$H NMR (DMSO-d$_6$, 400 MHz) δ 13.07 (br s, 1H), 8.03 (AA'XX', 2H, $J_{AA'}$=$J_{XX'}$=1.8 Hz, $J_{XA}$=$J_{X'A'}$=8.3 Hz, $J_{X'A}$=$J_{XA'}$=0.3 Hz, $v_A$=$v_{A'}$=3210.7 Hz, $v_X$=$v_{X'}$=3122.0 Hz), 7.81 (AA'XX', 2H, as above), 7.75 (m, 2H), 7.51 (tt, 2H, J=7.2, 1.1 Hz), 7.43 (tt, 1H, J=7.4, 1.2 Hz). $^{13}$C NMR (DMSO-d$_6$, 100 MHz) δ 167.2, 144.2, 139.0, 130.0, 129.8, 129.1, 128.3, 127.0, 126.8. HREIMS calculated for C$_{13}$H$_{10}$O$_2$ (M+) 198.0683. found 198.0683. Normal phase HPLC retention time: 13.8 min. Reverse phase HPLC retention time: 12.2 min. >99% pure.

Methyl-5-iodo-2-methoxybenzoate. TMS-diazomethane (19.25 mL, 38.50 mmol, 2 M solution in hexane) was added to a solution of 5-iodosalicylic acid (5.08 g, 19.24 mmol) in MeOH (20 mL) and stirred at rt for 11 h. Upon completion, the reaction was concentrated in vacuo and the residue was carried onto the next step without further purification.

Methyl iodide (2.40 mL, 38.48 mmol) and K$_2$CO$_3$ (10.60 g, 76.96 mmol) were added to a solution of 5-iodo-2-methoxybenzoate (5.37 g, 19.24 mmol) in DMF (20 mL) and stirred at rt under Ar for 24 h. Upon completion, ethyl acetate was added and the reaction was washed with 1% HCl (2×20 mL), brine (1×), dried over MgSO$_4$ and concentrated in vacuo. The residue was purified by flash chromatography (3:1 hexane:ethyl acetate) to afford methyl-5-iodo-2-methoxybenzoate (4.93 g, 88%) as a white solid. See, for example, Corey, E. J.; Myers, A. G. *J. Am. Chem. Soc.* 1985, 107, 5574-5576, which is incorporated by reference in its entirety.

¹H NMR (DMSO-d₆, 400 MHz) δ 7.90 (d, 1H, J=2.4 Hz), 7.80 (dd, 1H, J=8.8, 2.4 Hz), 6.96 (d, 1H, J=9.0 Hz), 3.81 (s, 3H), 3.79 (s, 3H). ¹³C NMR (DMSO-d₆, 100 MHz) δ 164.7, 158.0, 141.6, 138.5, 122.2, 115.2, 82.1, 55.9, 52.0. HREIMS calculated for $C_9H_9IO_3$ (M+) 291.9608. found 291.9596.

Compounds 23-27 were prepared according to Scheme 4. To a solution of methyl-5-iodo-2-methoxybenzoate (1.0 equiv) dissolved in enough toluene to give a concentration of 0.08 M, was added a solution of phenyl boronic acid (2.0 equiv) dissolved in EtOH to give a 0.8 M solution of boronic acid. A 2 M aqueous solution of $Na_2CO_3$ was added to give a final reaction concentration of 0.06 M with respect to the methoxybenzoate, followed by addition of $Pd(PPh_3)_4$ (10.0 mol %). The reaction was stirred at 60° C. under Ar for 15 h, and upon completion, was cooled to rt and extracted with $CH_2Cl_2$ (2×), washed with brine (1×), dried over $MgSO_4$ and concentrated in vacuo. The residue was purified by flash chromatography (3:1 hexane:ethyl acetate) to afford the methylated salicylates.

To a solution of the methylated salicylate (1.0 equiv) in enough $CH_2Cl_2$ to give a concentration of 0.06 M, was added $BBr_3$ (2.0 equiv, 1 M solution in $CH_2Cl_2$). The reaction was stirred at rt under Ar for 4 h, and upon completion, was quenched with $H_2O$ (10 mL), extracted with $CH_2Cl_2$ (2×), washed with brine (1×), dried over $MgSO_4$ and concentrated in vacuo. The residue was carried onto the next step without further purification.

To a solution of methyl ester (1.0 equiv) in THF:MeOH:$H_2O$ (1:1:1) at a concentration of 0.06 M, was added $LiOH·H_2O$ (3.0 equiv). The reaction was stirred at rt for 4 h, and upon completion, was acidified with 30% HCl, extracted with ethyl acetate (3×5 mL), dried over $MgSO_4$ and concentrated in vacuo. The residue was purified by flash chromatography ($CH_2Cl_2$, 1% MeOH, 0.2% acetic acid) to afford the biphenyl salicylates as white solids in 12-42% yields.

4'-Fluoro-4-hydroxybiphenyl-3-carboxylic acid (23). ¹H NMR ($CD_3OD$, 400 MHz) δ 8.01 (d, 1H, J=2.5 Hz), 7.65 (dd, 1H, J=8.7, 2.5 Hz), 7.51 (m, 2H), 7.11 (tt, 2H, J=10.0, 3.0 Hz), 6.97 (d, 1H, J=8.7 Hz). ¹³C NMR ($CD_3OD$, 100 MHz) δ 173.5, 165.0, 162.7, 137.7, 135.1, 132.6, 129.6, 129.3, 118.9, 116.7, 116.6, 114.2. HRESIMS calculated for $C_{13}H_9FO_3$ (M−H) 231.0459. found 231.0457. Normal phase HPLC retention time: 14.2 min. Reverse phase HPLC retention time: 12.8 min. >99% pure.

2'-Fluoro-4-hydroxybiphenyl-3-carboxylic acid (24). ¹H NMR ($CD_3OD$, 400 MHz) δ 7.98 (dd, 1H, J=2.2, 1.4 Hz), 7.59 (ddd, 1H, J=8.7, 2.4, 1.7 Hz), 7.36 (td, 1H, J=7.8, 1.7 Hz), 7.26 (dddd, 1H, J=9.9, 7.4, 4.9, 1.7 Hz), 7.16 (td, 1H, J=7.5, 1.2 Hz), 7.10 (ddd, 1H, J=11.1, 8.2, 1.3 Hz), 6.95 (d, 1H, J=8.5 Hz). ¹³C NMR ($CD_3OD$, 100 MHz) δ 173.5, 162.9, 162.4, 137.2, 131.8, 130.2, 130.1, 129.1, 128.1, 125.8, 118.5, 117.1, 114.0. HRESIMS calculated for $C_{13}H_9FO_3$ (M−H) 231.0457. found 231.0446. Normal phase HPLC retention time: 13.8 min. Reverse phase HPLC retention time: 12.7 min. >99% pure.

3',5'-Difluoro-4-hydroxybiphenyl-3-carboxylic acid (25). ¹H NMR ($CD_3OD$, 400 MHz) δ 8.07 (d, 1H, J=2.5 Hz), 7.73 (dd, 1H, J=8.5, 2.7 Hz), 7.15 (m, 2H), 7.01 (d, 1H, J=8.9 Hz), 6.86 (tt, 1H, J=9.0, 2.5 Hz). ¹³C NMR ($CD_3OD$, 100 MHz) δ 173.3, 166.3, 163.8, 145.1, 135.2, 131.0, 129.8, 119.2, 114.4, 110.4, 103.0. HRESIMS calculated for $C_{13}H_8F_2O_3$ (M−H) 249.0363. found 249.0356. Normal phase HPLC retention time: 14.5 min. Reverse phase HPLC retention time: 13.3 min. >99% pure.

2',4'-Dichloro-4-hydroxybiphenyl-3-carboxylic acid (26). ¹H NMR ($CD_3OD$, 400 MHz) δ 7.83 (d, 1H, J=2.2 Hz), 7.70 (d, 1H, J=2.0 Hz), 7.58 (dd, 1H, J=8.6, 2.4 Hz), 7.48 (ABX, 1H, $J_{AB}$=8.4 Hz, $J_{AX}$=2.2 Hz, $J_{BX}$=0.0 Hz, $v_A$=2989.4 Hz, $v_B$=2973.0 Hz), 7.44 (ABX, 1H, as above), 7.06 (d, 1H, J=8.7 Hz). ¹³C NMR ($CD_3OD$, 100 MHz) δ 171.6, 160.8, 137.5, 136.4, 132.8, 132.6, 132.4, 130.8, 129.2, 128.5, 127.7, 117.2, 112.9. HRESIMS calculated for $C_{13}H_8Cl_2O_3$ (M−H) 280.9772. found 280.9782. Normal phase HPLC retention time: 13.1 min. Reverse phase HPLC retention time: 14.4 min. >99% pure.

4-Hydroxybiphenyl-3-carboxylic acid (27). ¹H NMR ($CD_3OD$, 400 MHz) δ 8.08 (d, 1H, J=2.4 Hz), 7.73 (dd, 1H, J=8.7, 2.3 Hz), 7.54 (m, 2H), 7.41 (tt, 2H, J=7.3, 1.8 Hz), 7.29 (tt, 1H, J=7.8, 1.7 Hz), 7.38 (dddd, 1H, J=8.8, 6.4 Hz), 7.05 (d, 1H, J=8.7 Hz), 6.93 (m, 1H), 6.90 (ddd, 1H, J=7.3, 1.9 Hz), 7.00 (d, 1H, J=8.5 Hz). ¹³C NMR ($CD_3OD$, 100 MHz) δ 161.5, 140.1, 134.0, 132.4, 128.7, 128.3, 126.9, 126.3, 117.5, 112.9. HRESIMS calculated for $C_{13}H_{10}O_3$ (M−H) 213.0552. found 213.0545. Normal phase HPLC retention time: 12.9 min. Reverse phase HPLC retention time: 12.6 min. >99% pure.

4-Bromo-2,6-difluoroanisole. Methyl iodide (580 TL, 10.06 mmol) and $K_2CO_3$ (2.80 g, 20.12 mmol) were added to a solution of 4-bromo-2,6-difluorophenol (1.05 g, 5.03 mmol) in DMF (10 mL) and stirred at rt under Ar for 24 h. Upon completion, ethyl acetate was added and the reaction was washed with 1% HCl (2×20 mL), brine (1×), dried over $MgSO_4$ and concentrated in vacuo. The residue was purified by flash chromatography (hexane) to afford 4-bromo-2,6-difluoroanisole (747 mg, 67%) as a white solid. See, for example, Chambers, R. D.; et al. *J. Fluorine Chem.* 2000, 102, 169-174, which is incorporated by reference in its entirety. ¹H NMR ($CDCl_3$, 400 MHz) δ 7.06 (m, 2H), 3.97 (q, 3H, J=1.1 Hz). ¹³C NMR ($CDCl_3$, 100 MHz) δ 155.8, 136.3, 116.2, 113.8, 61.9. LREIMS found for $C_7H_5F_2OBr$ (M+) 223.0.

4-Bromo-2,6-dichloroanisole. Methyl iodide (467 TL, 8.12 mmol) and $K_2CO_3$ (2.24 g, 16.24 mmol) were added to a solution of 4-bromo-2,6-dichlorophenol (982 mg, 4.06 mmol) in DMF (10 mL) and stirred at rt under Ar for 40 min. Upon completion, ethyl acetate was added and the reaction was washed with 1% HCl (2×20 mL), brine (1×), dried over $MgSO_4$ and concentrated in vacuo. The residue was purified by flash chromatography (hexane) to afford 4-bromo-2,6-dichloroanisole (768 mg, 74%) as a white solid. See, for example, Li, J.; et al. *J. Med. Chem.* 1996, 39, 1846-1856, which is incorporated by reference in its entirety. ¹H NMR (DMSO-d₆, 400 MHz) δ 7.75 (s, 2H), 3.81 (s, 3H). ¹³C NMR (DMSO-d₆, 100 MHz) δ 151.3, 131.5, 129.6, 116.5, 60.6. HREIMS calculated for $C_7H_5BrCl_2O$ (M+) 253.8905. found 253.8901.

Compounds 28-31 were prepared according to Scheme 5. To a solution of the appropriate halo-anisole (1.0 equiv) dissolved in enough toluene to give a concentration of 0.25 M, was added a solution of phenyl boronic acid (2.0 equiv) dissolved in EtOH to give a 1.5 M solution of boronic acid. A 2 M aqueous solution of $Na_2CO_3$ was added to give a final reaction concentration of 0.08 M with respect to the halo-anisole, followed by addition of $Pd(PPh_3)_4$ (10.0 mol %). The reaction was stirred at 65° C. for 17 h, and upon completion, was cooled to rt and extracted with $CH_2Cl_2$ (2×), washed with brine (1×), dried over $MgSO_4$ and concentrated in vacuo. The residue was purified by flash chromatography (20:1 hexane:ethyl acetate) to afford the methylated biphenyl as a white solid.

To a solution of the methylated biphenyl (1.0 equiv) in enough $CH_2Cl_2$ to give a concentration of 0.20 M, was added $BBr_3$ (2.0 equiv, 1M solution in $CH_2Cl_2$). The reaction was stirred at rt under Ar for 3 h, and upon completion, was quenched with H₂O (10 mL), extracted with CH₂Cl₂ (2×), washed with brine (1×), dried over MgSO₄ and concentrated in vacuo. The residue was carried onto the next step without further purification.

To a solution of methyl ester (1.0 equiv) in THF:MeOH:H₂O (1:1:1) at a concentration of 0.04 M, was added LiOH.H₂O (3.0 equiv). The reaction was stirred at rt for 5 h, and upon completion, was acidified with 30% HCl, extracted with ethyl acetate (3×5 mL), dried over MgSO₄ and concentrated in vacuo. The residue was purified by flash chromatography (CH₂Cl₂, 1% MeOH, 0.2% acetic acid) to afford the biphenyl products as white solids in 14-39% yields.

3',5'-Difluoro-4'-hydroxybiphenyl-3-carboxylic acid (28). $^1$H NMR (DMSO-$d_6$, 400 MHz) δ 10.60 (br s, 1H), 8.14 (t, 1H, J=1.7 Hz), 7.91 (dt, 1H, J=7.7, 1.1 Hz), 7.88 (ddd, 1H, J=8.0, 2.0, 1.1 Hz), 7.55 (t, 1H, J=7.9 Hz), 7.41 (m, 2H). $^{13}$C NMR (DMSO-$d_6$, 100 MHz) δ 167.3, 154.0, 151.5, 138.4, 133.6, 131.6, 130.8, 129.9, 129.4, 128.4, 127.1, 110.3. HRESIMS calculated for $C_{13}H_8F_2O_3$ (M−H) 249.0363. found 249.0358. Normal phase HPLC retention time: 18.3 min. Reverse phase HPLC retention time: 10.5 min. >98% pure.

3',5'-Difluoro-4'-hydroxybiphenyl-4-carboxylic acid (29). $^1$H NMR (DMSO-$d_6$, 400 MHz) δ 7.98 (AA'XX', 2H, $J_{AA'}=J_{XX'}$=1.7 Hz, $J_{XA}=J_{X'A'}$=8.2 Hz, $J_{X'A}=J_{XA'}$=0.5 Hz, $v_A=v_{A'}$=3189.9 Hz, $v_X=v_{X'}$=3122.0 Hz), 7.81 (AA'XX', 2H, as above), 7.51 (m, 2H). $^{13}$C NMR (DMSO-$d_6$, 100 MHz) δ 167.7, 154.5, 142.5, 136.0, 130.5, 130.5, 130.4, 126.9, 111.0. HRESIMS calculated for $C_{13}H_8F_2O_3$ (M−H) 249.0363. found 249.0375. Normal phase HPLC retention time: 18.9 min. Reverse phase HPLC retention time: 10.2 min. >99% pure.

3',5'-Dichloro-4'-hydroxybiphenyl-3-carboxylic acid (30). $^1$H NMR (DMSO-$d_6$, 400 MHz) δ 8.13 (t, 1H, J=1.6 Hz ), 7.91 (m, 2H), 7.70 (s, 2H), 7.56 (t, 1H, J=7.8 Hz). $^{13}$C NMR (DMSO-$d_6$, 100 MHz) δ 167.2, 149.0, 137.9, 132.2, 131.6, 130.8, 129.3, 128.4, 127.1, 126.8, 122.9, 123.0. HRESIMS calculated for $C_{13}H_8Cl_2O_3$ (M−H) 280.9772. found 280.9767. Normal phase HPLC retention time: 16.2 min. Reverse phase HPLC retention time: 11.6 min. >99% pure.

3',5'-Dichloro-4'-hydroxybiphenyl-4-carboxylic acid (31). $^1$H NMR (DMSO-$d_6$, 400 MHz) δ 7.98 (AA'XX', 2H, $J_{AA'}=J_{XX'}$=1.7 Hz, $J_{XA}=J_{X'A'}$=8.1 Hz, $J_{X'A}=J_{XA'}$=0.5 Hz, $v_A=v_{A'}$=3189.9 Hz, $v_X=v_{X'}$=3110.0 Hz), 7.81 (AA'XX', 2H, as above), 7.78 (s, 2H). $^{13}$C NMR (DMSO-$d_6$, 100 MHz) δ 167.2, 141.8, 141.7, 134.7, 129.9, 129.7, 126.9, 126.4, 123.0. HRESIMS calculated for $C_{13}H_8Cl_2O_3$ (M−H) 280.9772. found 280.9785. Normal phase HPLC retention time: 15.9 min. Reverse phase HPLC retention time: 11.4 min. >97% pure.

Methyl-2',4'-difluoro-4-hydroxybiphenyl-3-carboxylate (32). Compounds 32 and 33 were prepared according to Scheme 6. TMS-diazomethane (5.87 mL, 11.75 mmol, 2 M solution in hexane) was added to a solution of diflunisal (1.03 g, 4.11 mmol) in MeOH (10 mL) and stirred at rt for 5 h. Upon completion, the reaction was concentrated in vacuo and the residue was purified by flash chromatography (10:1 hexane:ethyl acetate) to afford 32 (774 mg, 71%) as a white solid. $^1$H NMR (CDCl₃, 400 MHz) δ 7.97 (dd, 1H, J=2.2, 1.3 Hz), 7.59 (dt, 1H, J=8.8, 2.1 Hz), 7.36 (dq, 1H, J=7.7, 1.5 Hz), 7.48 (td, 1H, J=7.8, 1.7 Hz), 7.38 (dddd, 1H, J=8.8, 6.4 Hz), 7.05 (d, 1H, J=8.7 Hz), 6.93 (m, 1H), 6.90 (ddd, 1H, J=10.6, 8.9, 2.5 Hz), 3.96 (s, 3H). $^{13}$C NMR (CDCl₃, 100 MHz) δ 170.6, 163.6, 161.3, 158.5, 136.4, 131.2, 130.3, 126.2, 124.2, 118.0, 112.6, 111.8, 104.6, 52.6, 124.2. HRFABMS calculated for $C_{14}H_{10}F_2O_3$ (M+) 264.0596. found 264.0598. Normal phase HPLC retention time: 6.9 min. Reverse phase HPLC retention time: 14.7 min. >99% pure.

2',4'-Difluoro-4-methoxybiphenyl-3-carboxylic acid (33). Methyl iodide (350 TL, 1.16 mmol) and K₂CO₃ (320 mg, 2.32 mmol) were added to a solution of 32 (152 mg, 0.58 mmol) in DMF (4 mL) and stirred at rt under Ar for 14 h. Upon completion, ethyl acetate was added and the reaction was washed with 1% HCl (2×20 mL), brine (1×), dried over MgSO₄ and concentrated in vacuo and carried onto the next step without further purification.

LiOH.H₂O (60 mg, 1.43 mmol) was added to a solution of fully methylated diflunisal (140 mg, 0.50 mmol) in MeOH:THF:H₂O (4.5 mL 1:1:1), and stirred at rt for 4 h. Upon completion, the reaction was acidified with 30% HCl, extracted with ethyl acetate (3×5 mL), dried over MgSO₄ and concentrated in vacuo. The residue was purified by flash chromatography (2:1 ethyl acetate:hexane, 1% acetic acid) to afford 33 (122 mg, 93%) as a white solid. $^1$H NMR (CDCl₃, 400 MHz) δ 10.77 (br s, 1H), 8.31 (dd, 1H, J=2.5, 0.9 Hz), 7.75 (dt, 1H, J=8.6, 2.1 Hz), 7.41 (dt, 1H, J=8.9, 6.6 Hz), 7.15 (d, 1H, J=8.8 Hz), 6.94 (m, 1H), 4.13 (s, 3H). $^{13}$C NMR (CDCl₃, 100 MHz) δ 177.7, 161.4, 158.2, 135.7, 133.9, 131.4, 129.0, 123.5, 118.1, 112.2, 112.0, 104.6, 56.9. HRESIMS calculated for $C_{14}H_{10}F_2O_3$ (M−H) 263.0520. found 263.0514. Normal phase HPLC retention time: 21.6 min. Reverse phase HPLC retention time: 11.9 min. >99% pure.

Compounds 34-38 were prepared according to Scheme 7. Compounds 39-44 were prepared according to Scheme 8. To a solution of aryl iodide (1.0 equiv) in enough toluene to give a concentration of 0.07 M, was added an appropriate formyl phenylboronic acid dissolved in enough EtOH to provide a concentration of 0.4 M boronic acid. A 2 M aqueous solution of Na₂CO₃ was added to give a final reaction concentration of 0.04 M with respect to aryl iodide, followed by addition of Pd(PPh₃)₄ (3.0 mol %). The reaction was heated to reflux under Ar for 18 h, and upon completion, was cooled to rt and extracted with CH₂Cl₂ (2×), washed with brine (1×), dried over MgSO₄ and concentrated in vacuo. The residue was purified by flash chromatography (40:1 hexane:ethyl acetate) to afford the biphenyl aldehydes as white solids in 40-91% yields.

3',5'-Dichloro-3-formylbiphenyl (39). $^1$H NMR (CDCl₃, 400 MHz) δ 10.09 (s, 1H), 8.04 (t, 1H, J=1.8 Hz), 7.91 (dt, 1H, J=7.6, 1.3 Hz), 7.80 (ddd, 1H, J=7.8, 2.0, 1.3 Hz), 7.64 (t, 1H, J=7.8 Hz), 7.49 (d, 2H, J=1.8 Hz), 7.38 (t, 1H, J=1.9 Hz). $^{13}$C NMR (CDCl₃, 100 MHz) δ 192.0, 142.8, 139.7, 137.2, 135.8, 133.0, 130.1, 130.0, 128.1, 128.0, 125.9. HRFABMS calculated for $C_{13}H_8Cl_2O$ (M+H) 251.0027. found 251.0027. Normal phase HPLC retention time: 8.0 min. Reverse phase HPLC retention time: 15.2 min. >99% pure.

3',5'-Dichloro-4-formylbiphenyl (40). $^1$H NMR (CDCl₃, 400 MHz) δ 7.99 (AA'XX', 2H, $J_{AA'}=J_{XX'}$=2.1 Hz, $J_{XA}=J_{X'A'}$=8.5 Hz, $J_{X'A}=J_{XA'}$=0.7 Hz, $v_A=v_{A'}$=3193.7 Hz, $v_X=v_{X'}$=3077.8 Hz), 7.70 (AA'XX', 2H, as above), 7.47 (t, 1H, J=1.9 Hz), 7.39 (d, 2H, J=1.9 Hz). $^{13}$C NMR (CDCl₃, 100 MHz) δ 191.8, 144.4, 142.9, 136.2, 135.8, 130.6, 128.5, 127.9, 126.1. HREIMS calculated for $C_{13}H_8Cl_2O$ (M−H) 248.9873. found 248.9874. Normal phase HPLC retention time: 7.9 min. Reverse phase HPLC retention time: 15.2 min. >99% pure.

3',5'-Dichloro-2-formylbiphenyl (41). $^1$H NMR (CDCl₃, 400 MHz) δ 9.98 (s, 1H), 8.03 (dd, 1H, J=7.8, 1.3 Hz), 7.66 (td, 1H, J=7.6, 1.5 Hz), 7.55 (tt, 1H, J=7.6, 1.0 Hz), 7.44 (t, 1H, J=1.9 Hz), 7.39 (dd, 1H, J=7.7, 1.0 Hz), 7.27 (d, 2H, J=1.9 Hz). $^{13}$C NMR (CDCl₃, 100 MHz) δ 191.4, 142.9, 141.0, 135.3, 134.0, 133.7, 130.7, 129.0, 128.5, 128.4, 128.4.

HRFABMS calculated for $C_{13}H_8Cl_2O$ (M+H) 251.0030. found 251.0029. Normal phase HPLC retention time: 7.0 min. Reverse phase HPLC retention time: 14.9 min. >99% pure.

Compounds 45-47 were prepared according to Scheme 8. To a solution of biphenyl aldehyde (1.0 equiv) in enough acetone to give a concentration of 0.07 M, was added $KMnO_4$ (2.0 equiv) in enough $H_2O$ to give a concentration of 0.2 M permanganate. The reaction was stirred for 16 h at rt, and upon completion, was concentrated in vacuo and the resulting residue was redissolved in 10:1 $CH_2Cl_2$:MeOH and filtered through a plug of glass wool. The crude product was purified by flash chromatography (10:1 $CH_2Cl_2$:MeOH) to afford the carboxylic acids (58 mg, 100%) as white solids in 82-100% yields. 2',4'-Dichlorobiphenyl-3-carboxylic acid (45). $^1$H NMR (DMSO-$d_6$, 400 MHz) δ 8.22 (br s, 1H), 8.00 (br s, 1H), 7.94 (d, 1H, J=7.5 Hz), 7.76 (s, 2H), 7.63 (s, 1H), 7.60 (br s, 1H). $^{13}$C NMR (DMSO-$d_6$, 100 MHz) δ 168.0, 143.7, 138.1, 135.4, 131.6, 129.9, 127.9, 126.2. HRESIMS calculated for $C_{13}H_8Cl_2O_2$ (M−H) 264.9823. found 264.9810. Normal phase HPLC retention time: 12.3 min. Reverse phase HPLC retention time: 14.2 min. >99% pure.

2',4'-Dichlorobiphenyl-4-carboxylic acid (46). $^1$H NMR ($CD_3OD$, 400 MHz) δ 8.11 (br s, 2H) 7.72 (m, 2H), 7.64 (d, 2H, J=1.9 Hz), 7.46 (t, 1H, J=1.7 Hz). $^{13}$C NMR (DMSO-$d_6$, 100 MHz) δ 170.3, 140.6, 135.2, 127.2, 126.4, 119.3, 118.6, 117.4. HRESIMS calculated for $C_{13}H_8Cl_2O_2$ (M−H) 264.9830. found 264.9823. Normal phase HPLC retention time: 12.5 min. Reverse phase HPLC retention time: 14.4 min. >99% pure.

2',4'-Dichlorobiphenyl-2-carboxylic acid (47). $^1$H NMR (DMSO-$d_6$, 400 MHz) δ 7.75 (br s, 1H), 7.56 (s, 2H), 7.48 (m, 2H), 7.36 (m, 2H). $^{13}$C NMR (DMSO-$d_6$, 100 MHz) δ 170.1, 152.5, 145.2, 133.3, 130.0, 129.6, 128.0, 127.2, 126.3. HRESIMS calculated for $C_{13}H_8Cl_2O_2$ (M−H) 264.9823. found 264.9834. Normal phase HPLC retention time: 11.4 min. Reverse phase HPLC retention time: 13.6 min. >99% pure.

Compounds 48-53 were prepared according to Scheme 8. To a solution of biphenyl aldehyde (1.0 equiv) in enough MeOH to give a concentration of 0.1 M, was added $NaBH_4$ (2.0 equiv) in enough MeOH to give a concentration of 0.3 M borohydride. The reaction was stirred at 0° C., and slowly warmed to rt, and after stirring for 16 h, was concentrated in vacuo and purified by flash chromatography (3:1 hexane: ethyl acetate) to afford the biphenyl alcohols as a white solids in 94-100% yields.

3',5'-Dichlorobiphenyl-3-yl-methanol (48). $^1$H NMR ($CDCl_3$, 400 MHz) δ 7.54 (m, 1H), 7.46 (d, 2H, J=1.8 Hz), 7.45 (m, 2H), 7.39 (m, 1H), 7.34 (t, 1H, J=1.9 Hz), 4.77 (s, 2H), 1.90 (br s, 1H). $^{13}$C NMR ($CDCl_3$, 100 MHz) δ 144.1, 141.9, 139.0, 135.5, 129.5, 127.4, 127.1, 126.5, 125.8, 125.7, 65.3. HREIMS calculated for $C_{13}H_{10}Cl_2O$ (M+) 252.0103. found 252.0109. Normal phase HPLC retention time: 13.9 min. Reverse phase HPLC retention time: 14.0 min. >99% pure.

3',5'-Dichlorobiphenyl-4-yl-methanol (49). $^1$H NMR ($CDCl_3$, 400 MHz) δ 7.53 (AA'XX', 2H, $J_{AA'}$=1.9 Hz, $J_{XX'}$=3.1 Hz, $J_{XA}$=8.7 Hz, $J_{X'A'}$=6.4 Hz, $J_{X'A}$=$J_{XA'}$=0.5 Hz, $v_A$=$v_{A'}$=3009.8 Hz, $v_X$=$v_{X'}$=2977.8 Hz), 7.45 (AA'XX', 2H, as above), 7.45 (d, 2H, J=1.9 Hz), 7.33 (t, 1H, J=1.9 Hz), 4.75 (br d, 2H, J=4.8 Hz), 1.81 (br t, 1H, J=5.2 Hz). $^{13}$C NMR ($CDCl_3$, 100 MHz) δ 144.0, 141.4, 138.0, 135.5, 127.8, 127.4, 125.8, 65.1. HREIMS calculated for $C_{13}H_{10}Cl_2O$ (M+) 251.0110. found 252.0109. Normal phase HPLC retention time: 15.4 min. Reverse phase HPLC retention time: 14.0 min. >97% pure.

3',5'-Dichlorobiphenyl-2-yl-methanol (50). $^1$H NMR ($CDCl_3$, 400 MHz) δ 7.55 (dd, 1H, J=7.5, 1.3 Hz), 7.43 (td, 2H, J=7.5, 1.4 Hz), 7.38 (m, 2H), 7.29 (d, 2H, J=1.9 Hz), 7.24 (dd, 1H, J=7.4, 1.4 Hz), 4.58 (s, 2H), 1.79 (s, 1H). $^{13}$C NMR ($CDCl_3$, 100 MHz) δ 143.7, 138.9, 137.9, 134.9, 130.0, 129.0, 128.9, 128.2, 127.9, 127.6, 63.0. HREIMS calculated for $C_{13}H_{10}Cl_2O$ (M+) 252.0110. found 252.0109. Normal phase HPLC retention time: 11.5 min. Reverse phase HPLC retention time: 14.0 min. >99% pure.

Compounds 54 and 55 were prepared according to Scheme 9. To a solution of the appropriate iodobenzaldehyde (1.0 equiv) in enough toluene to give a concentration of 0.07 M, was added 3,5-difluorophenyl boronic acid (2.0 equiv) dissolved in enough EtOH to provide a concentration of 1.0 M boronic acid. A 2 M aqueous solution of $Na_2CO_3$ was added to give a final reaction concentration of 0.04 M with respect to iodobenzaldehyde, followed by addition of $Pd(PPh_3)_4$ (4.0 mol %). The reaction was stirred at 60° C. for 17 h, and upon completion, was cooled to rt and extracted with $CH_2Cl_2$ (2×), washed with brine (1×), dried over $MgSO_4$ and concentrated in vacuo. The residue was purified by flash chromatography (10:1 hexane:ethyl acetate) to afford the biphenyl aldehydes as white solids in 78-80% yields.

3',5'-Difluoro-3-formylbiphenyl (54). $^1$H NMR ($CDCl_3$, 400 MHz) δ 10.06 (s, 1H), 8.02 (t, 1H, J=1.4 Hz), 7.88 (dt, 1H, J=7.8, 1.4 Hz), 7.78 (ddd, 2H, J=7.8, 2.0, 1.2 Hz), 7.61 (t, 2H, J=7.7), 7.10 (m, 2H), 6.80 (tt, 1H, J=8.8, 2.3 Hz. $^{13}$C NMR ($CDCl_3$, 100 MHz) δ 192.0, 164.8, 162.3, 143.0, 139.8, 137.1, 132.9, 129.9, 127.9, 110.4, 103.5. HRFABMS calculated for $C_{13}H_8F_2O$ (M+H) 219.0620. found 219.0621. Normal phase HPLC retention time: 8.9 min. Reverse phase HPLC retention time: 13.7 min. >99% pure.

3',5'-Difluoro-4-formylbiphenyl (55). $^1$H NMR ($CDCl_3$, 400 MHz) δ 9.98 (s, 1H), 8.02 (dd, 1H, J=7.8, 1.5 Hz), 7.65 (td, 1H, J=7.3, 1.4 Hz), 7.54 (t, 1H, J=7.8 Hz), 7.40 (dd, 1H, J=7.6, 1.2 Hz), 6.90 (m, 3H). $^{13}$C NMR ($CDCl_3$, 100 MHz) δ 191.5, 164.1, 161.6, 143.4, 141.3, 134.0, 133.7, 130.6, 129.0, 128.3, 113.3, 103.8. HRFABMS calculated for $C_{13}H_8F_2O$ (M+H) 219.0620. found 219.0621. Normal phase HPLC retention time: 7.0 min. Reverse phase HPLC retention time: 13.4 min. >99.% pure.

A number of in vitro tests can be used to evaluate the compounds for their ability to stabilize transthyretin tetramers or prevent formation of fibrils. The tests can include a fibril formation assay, a plasma selectivity assay, determination of the three-dimensional structure of a transthyretin:compound complex (e.g. by X-ray crystallography), kinetics of transthyretin tetramer dissociation or fibril formations, and determining the stoichiometry and energetics of transthyretin: compound interactions, by, for example, centrifugation or calorimetry. Details of exemplary in vitro assays are presented below.

Each compound was subjected to a stagnant fibril formation assay. Compounds were dried over $P_2O_5$ overnight and dissolved in DMSO to a final concentration of 7.2 mM to provide a primary stock solution (10× stock). A secondary stock solution was prepared by five-fold dilution of the primary stock solution with DMSO to a final concentration of 1.44 mM (2× stock). The acid-mediated amyloidogenicity of TTR (3.6 TM) in the presence of inhibitors (1.44 mM) was measured as follows: To a disposable UV cuvette were added 495 TL of a 0.4 mg/mL WT TTR protein solution in 10 mM sodium phosphate, 100 mM KCl and 1 mM EDTA (pH 7.6) and 5 TL of the 1.44 mM secondary stock inhibitor solution in DMSO (2× stock). The mixture was vortexed and incubated for 30 min (25° C.), at which time the pH was lowered to 4.4 with 500 TL of 200 mM acetate, 100 mM KCl and 1 mM EDTA (pH 4.2). The final 1 mL solution was vortexed and incubated for 72 h at 37° C. without agitation. After 72 h, the cuvettes were vortexed to suspend any fibrils present, and the turbidity of the suspension was measured at 350 and 400 nm using a UV-vis spectrometer. The percent fibril formation was obtained by the ratio of the observed turbidities for each TTR plus inhibitor sample relative to that of a sample prepared the same way, but lacking inhibitor, multiplied by 100. The fibril formation assay employing equimolar inhibitor and TTR concentrations (3.6 TM) was performed as above using a 1× secondary stock solution. The 1× stock solution was prepared by ten-fold dilution of the 7.2 mM 10× primary stock solution with DMSO to a final concentration of 0.72 mM and used in the fibril formation assay as described above. All assays were performed in triplicate and all compounds were assayed using wild-type TTR. All compounds were found to be soluble throughout the course of the experiment by testing the turbidities of the solutions in the absence of WT TTR, ensuring that turbidity was the result of TTR amyloid formation.

The binding stoichiometries of potential inhibitors to TTR in blood plasma were evaluated by an antibody capture/HPLC method. A 1.5-mL eppendorf tube was filled with 1.0 mL of human blood plasma and 7.5 TL of a 1.44 mM DMSO solution of the inhibitor under evaluation. The solution was incubated and gently rocked at 37° C. for 24 h. A 1:1 gel:TSA (Tris saline) slurry (125 TL) of quenched sepharose was added to the solution and gently rocked at 4° C. for 1 h. The solution was centrifuged (16,000×g) and the supernatant was divided into two 400 TL aliquots, which were then added to different 200 TL samples of a 1:1 gel:TSA slurry of the anti-TTR antibody-conjugated sepharose. The solutions were gently rocked at 4° C. for 20 min, centrifuged (16,000×g), and the supernatant was removed. The gel was washed with 1 mL of TSA/0.05% saponin (3×, 10 min each) at 4° C., followed by 1 mL of TSA (2×, 10 min each) at 4° C. The samples were centrifuged (16,000×g), the final wash was removed, and 155 TL of 100 mM triethylamine, pH 11.5, was added to elute the TTR and bound inhibitors from the antibodies. After gentle rocking at 4° C. for 30 min, the elution sample was centrifuged (16,000×g) and 145 TL of the supernatant, containing TTR and inhibitor, were removed. The supernatant was then analyzed by reverse-phase HPLC as described previously. See, for example, Purkey, H. E.; Dorrell, M. I.; Kelly, J. W. *Proc. Natl. Acad. Sci. U.S.A.* 2001, 98, 5566-71, which is incorporated by reference in its entirety.

Crystals of WT TTR were obtained from protein solutions at 7 mg/mL (in 100 mM KCl, 1 mM EDTA, 10 mM sodium phosphate, pH 7.0, 0.35-0.50 M ammonium sulfate) equilibrated against 2 M ammonium sulfate in hanging drops. The TTR-ligand complexes were prepared from crystals soaked for more than three weeks with a 10-fold molar excess of the ligand. A CCD-PXL-L600 detector (Bruker instruments) coupled to an RU200 rotating anode X-ray generator was used for data collection of crystals soaked with 20 or 26. The Quantum-4 detector at the monochromatic high-energy source of 14-BM-C, BIOCARS, Advance Photon Source was used for the data collection of crystals soaked with 1 or 18. The crystals were placed in paratone oil as a cryo-protectant and cooled for diffraction experiments (120 K for 20 and 26, and 100 K for 1 and 18). Crystals of TTR•ligand complex structures are isomorphous with the apo crystal form with unit cell dimensions close to a=43 Å, b=85 Å, and c=66 Å; space group $P2_12_12$ with two monomers in the asymmetric unit. Data sets of 1 and 18 were reduced with DENZO and SCALEPACK. See Otwinowski, Z.; Minor, W. Macromolecular Crystallography, Part A, in *Methods in Enzymology*; Carter, C. W., Sweet, R. M., Eds.; Academic Press: 1997; Vol. 276, p 307-326, which is incorporated by reference in its entirety. Data sets of 20 and 26 were reduced with SAINT and PROSCALE (Bruker AXS, Inc.).

The protein atomic coordinates for TTR from the Protein Data Bank (accession number 1 BMZ) were used as a starting model during the molecular replacement search by EPMR. The best solutions from EPMR were refined by molecular dynamics and energy minimization protocols of CNS. The resulting difference Fourier maps revealed binding of the ligands (in two conformations for 18, 20 and 26, and four conformations for 1) in each binding pocket of the TTR tetramer. Using these maps, the ligand could be unambiguously placed into the density and was included in the crystallographic refinement. After several cycles of simulated annealing and subsequent positional and temperature factor refinement, water molecules were placed into difference Fourier maps. The final cycle of map-fitting was done using the unbiased weighted electron density map calculated by the shake/warp bias removal protocol. All binding conformations of the ligand were in good agreement with unbiased annealed omit maps as well as the shake/warp unbiased weighted maps phased in the absence of the inhibitor. Final cycles of the refinement were carried out by the restrained refinement protocol of Refmac. Because of the lack of interpretable electron densities in the final map, the nine N-terminal and three C-terminal residues were not included in the final model. A summary of the crystallographic analysis is presented in Table 2. See, for example, Kissinger, C. R.; Gehlhaar, D. K.; Fogel, D. B. *Acta Crystallogr., Sect. D* 1999, 55, 484-491; Brunger, A. T.; et al. *Acta Crystallogr., Sect. D* 1998, 54, 905-921; Kantardjieff, K.; et al. *Acta Crystallogr., Sect. D* 2002, 58, 735-743; Bailey, S. *Acta Crystallogr., Sect. D* 1994, 50, 760-763; and Murshudov, G. N.; Vagin, A. A.; Dodson, E. J. *Acta Crystallogr., Sect. D* 1997, 53, 240-255, each of which is incorporated by reference in its entirety.

The kinetics of TTR tetramer dissociation was evaluated by linked monomer unfolding in urea. Slow tetramer dissociation is not detectable by far-UV CD spectroscopy, but is linked to the rapid (500,000-fold faster) unfolding step easily detectable by far-UV CD as described previously. TTR tetramer (3.6 TM) dissociation kinetics as a function of inhibitor (3.6 TM) were evaluated by adding 3.6 TL of a 1 mM solution (in ethanol) of the inhibitor of interest to 69 TL of WT TTR (2.90 mg/mL, 10 mM sodium phosphate, 100 mM KCl, 1 mM EDTA, pH 7.0) to which was added 127.4 TL of phosphate buffer. For an inhibitor concentration (7.2 TM) twice that of the TTR concentration (3.6 TM), 7.2 TL of a 1 mM solution (in ethanol) of the inhibitor of interest was added to 69 TL of WT TTR (2.90 mg/mL, 10 mM sodium phosphate, 100 mM KCl, 1 mM EDTA, pH 7.0) to which was added 123.8 TL of phosphate buffer. 100 TL of the protein-inhibitor solution of interest was added to a solution of 600 TL of 10.3 M urea and 300 TL of phosphate buffer, to yield a final urea concentration of 6.5 M. The solutions were vortexed and the circular dichroism spectra were collected at the following intervals: 0, 5, 8, 23, 46, 71, 95, 118, 144 and 168 h. A control sample containing 7.2 TL of ethanol rather than inhibitor was prepared for comparison and the spectra were collected at the time points identified above. CD spectra were collected between 220 and 213 nm, with scanning every 0.5 nm and an averaging time of 10 sec. Each wavelength was scanned once. The values for the amplitude were averaged between 220 and 213 nm to determine the extent of θ-sheet loss throughout the experiment.

The rate of acid-mediated fibril formation was followed at pH 4.4 by turbidity. Compounds were dried over $P_2O_5$ overnight and dissolved in DMSO to a final concentration of 7.2 mM to provide a primary stock solution (10× stock). A secondary stock solution was prepared by five-fold DMSO dilution of the primary stock solution to yield a final concentration of 1.44 mM (2× stock). The fibril formation assay employing an inhibitor concentration of 7.2 TM relative to 3.6 µM TTR (tetramer) was performed as follows: To a disposable UV cuvette were added 495 TL of a 0.4 mg/mL WT TTR protein solution in 10 mM sodium phosphate, 100 mM KCl and 1 mM EDTA (pH 7.6) and 5 TL of the 1.44 mM secondary inhibitor stock solution (2× stock). The mixture was vortexed and incubated for 30 min (25° C.). After 30 min, the pH was lowered to 4.4 with 500 TL of 200 mM acetate, 100 mM KCl, 1 mM EDTA (pH 4.2). The final 1 mL solution was vortexed and incubated at 37° C. without agitation. The solutions were vortexed and turbidity at 350 and 400 nm was measured. UV spectra were collected at the following intervals: 0, 4, 8, 24, 48, 72, 96, 120, 144, 168 and 192 h after acidification. A control sample containing 5 TL of DMSO was prepared for comparison, and the spectra were collected at the time points above. Each inhibitor solution was prepared in groups of 10 to prevent disturbance of the cuvettes before a reading was taken. After a UV absorbance was obtained, the cuvettes corresponding to that time-point were discarded. The fibril formation assay employing equimolar (3.6 TM) TTR and inhibitor concentration was performed as above using a 1× secondary inhibitor stock solution prepared as follows: A stock solution was prepared by ten-fold dilution of the 7.2 mM 10× primary stock solution with DMSO to a final concentration of 0.72 mM and used in the fibril formation assay as described above. All compounds were found to be soluble throughout the course of the experiment, ensuring that turbidity was the result of TTR amyloid formation.

The TTR quaternary structure in the presence of inhibitors at pH 4.4 was analyzed. The mechanism by which 18 and 20 stabilize TTR was evaluated by incubating the protein (3.6 µM) for 72 h under the conditions of the stagnant fibril formation assay in the presence of either 3.6 µM or 7.2 µM inhibitor. After 72 h, the samples were centrifuged (14,000× g) and the supernatant was removed from any solid that was formed in the assay. Equilibrium and velocity ultracentrifugation analysis was achieved with a Beckman XL-I analytical ultracentrifuge. The acquisition and analysis of data was performed as described previously. See, for example, Lashuel, H. A.; Lai, Z.; Kelly, J. W. *Biochemistry* 1998, 37, 17851-64; and Lashuel, H. A.; et al. *Biochemistry* 1999, 38, 13560-73, each of which is incorporated by reference in its entirety.

The dissociation constants characterizing the binding of 18 and 20 to WT TTR were determined by isothermal titration calorimetry using a Microcal instrument (Microcal Inc., Northhampton, Md.). A solution of inhibitor (300 µM or 500 µM in 25 mM tris buffer, 100 mM KCl, 1 mM EDTA, 12% EtOH, pH 8.0) was prepared and titrated into an ITC cell containing WT TTR (15 µM or 25 µM in 25 mM tris buffer, 100 mM KCl, 1 mM EDTA, 12% EtOH, pH 8.0). The initial injection of 2.5 µL was followed by 50 injections of 5.0 µL each (25° C.). Integration of the thermogram after subtraction of blanks yielded a binding isotherm that fit best to a model of two sequential binding sites with negative cooperativity. The data were fit by a nonlinear least squares approach with four adjustable parameters, namely, $K_1$, $\Delta H_1$, $K_2$, $\Delta H_2$ using the ITC data analysis module in ORIGIN version 2.9 provided by Microcal.

The compounds described were evaluated as TTR amyloid fibril inhibitors using a turbidity assay. WT TTR amyloidosis was initiated by acidification of TTR preincubated with inhibitor (25° C., 30 min), employing buffer addition to jump the pH to a final value of 4.4. After incubation of each mixture for 72 h (37° C.), the turbidity was measured at 350 and 400 nm using a UV-vis spectrometer. All amyloid fibril formation data was normalized to WT TTR amyloidogenesis in the absence of inhibitor, assigned to be 100% fibril formation. Therefore, 5% fibril formation corresponds to a compound inhibiting 95% of WT TTR fibril formation after 72 h. Each potential inhibitor was first evaluated at a concentration of 7.2 µM relative to a TTR tetramer concentration of 3.6 TM. Compounds allowing less than 15% fibril formation were reevaluated at a concentration equal to the TTR concentration (3.6 TM) to select for the inhibitors with the highest efficacy. Fibril formation of less than 40% under these conditions is characteristic of a very good inhibitor, whereas 40-70% inhibition is indicative of a modest compound. Fibril formation data is presented in Table 1.

TABLE 1

Effects of Compounds on Fibril Formation

| Compound Number | Structure | % fibril formation (3.6 µM inhibitor) | % fibril formation (7.2 µM inhibitor) | Plasma Selectivity (equiv bound) |
|---|---|---|---|---|
| diflunisal (1) | 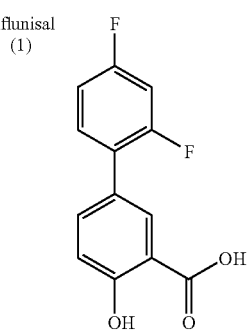 | 37.0 | 3.4 | 0.13 ± 0.02 |

TABLE 1-continued
Effects of Compounds on Fibril Formation
| Compound Number | Structure | % fibril formation (3.6 μM inhibitor) | % fibril formation (7.2 μM inhibitor) | Plasma Selectivity (equiv bound) |
|---|---|---|---|---|
| 2 | 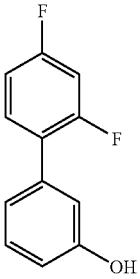 | | 31.5 | |
| 3 | 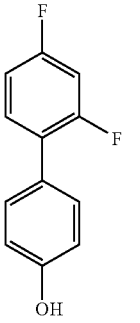 | | 32.4 | |
| 4 | 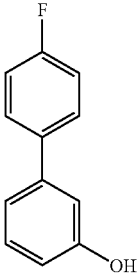 | | 46.3 | |
| 5 | 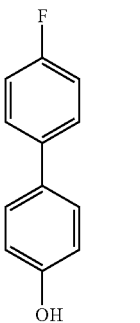 | | 53.1 | |
| 6 | 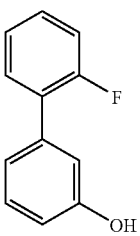 | | 19.5 | |

TABLE 1-continued
Effects of Compounds on Fibril Formation
| Compound Number | Structure | % fibril formation (3.6 μM inhibitor) | % fibril formation (7.2 μM inhibitor) | Plasma Selectivity (equiv bound) |
|---|---|---|---|---|
| 7 | 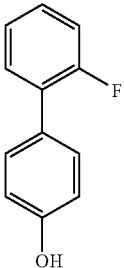 |  | 19.6 |  |
| 8 | 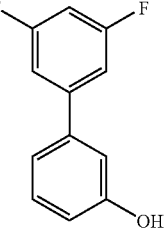 | 40.9 | 10.2 | 0.18 ± 0.05 |
| 9 | 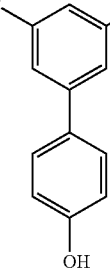 |  | 16.4 |  |
| 10 | 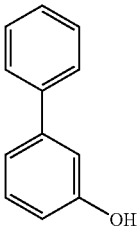 |  | 61.2 |  |
| 11 | 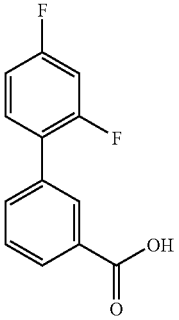 | 39.4 | 9.1 | none observed |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
| --- | --- | --- | --- | --- |
| 12 | 2,4-difluoro biphenyl-4-carboxylic acid | 32.6 | 2.6 | 0.20 ± 0.05 |
| 13 | 4'-fluoro biphenyl-3-carboxylic acid | | 15.7 | |
| 14 | 4'-fluoro biphenyl-4-carboxylic acid | | 13.3 | |
| 15 | 2'-fluoro biphenyl-3-carboxylic acid | 39.4 | 9.8 | none observed |

TABLE 1-continued
Effects of Compounds on Fibril Formation
| Compound Number | Structure | % fibril formation (3.6 μM inhibitor) | % fibril formation (7.2 μM inhibitor) | Plasma Selectivity (equiv bound) |
|---|---|---|---|---|
| 16 | 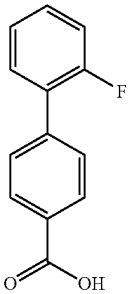 | 32.4 | 4.8 | 0.08 ± 0.00 |
| 17 | 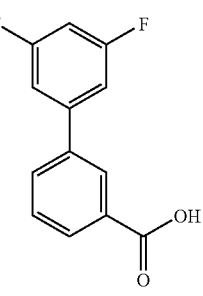 | 35.7 | 5.6 | 0.23 ± 0.00 |
| 18 | 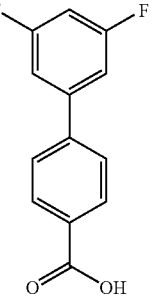 | 35.7 | 3.7 | 1.27 ± 0.12 |
| 19 | 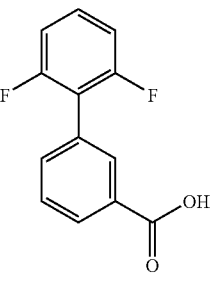 | 35.1 | 6.7 | 0.29 ± 0.12 |
| 20 | 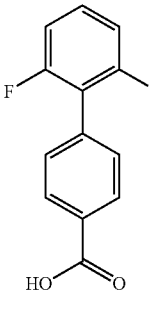 | 28.5 | 4.5 | 0.50 ± 0.05 |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
|---|---|---|---|---|
| 21 | 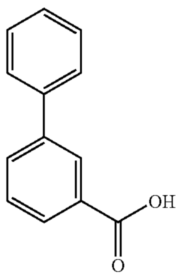 | | 30.8 | |
| 22 | 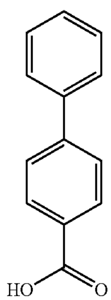 | 51.5 | 14.3 | 0.08 ± 0.01 |
| 23 | 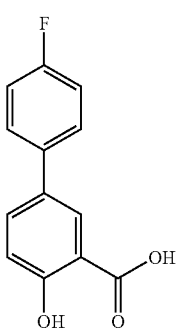 | 38.7 | 2.6 | 0.09 ± 0.00 |
| 24 | 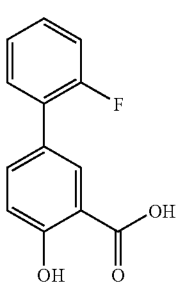 | 38.7 | 2.5 | 0.07 ± 0.02 |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
|---|---|---|---|---|
| 25 | (3,5-difluorophenyl)-4-hydroxy-3-carboxyphenyl | 35.5 | 1.0 | none observed |
| 26 | (2,4-dichlorophenyl)-4-hydroxy-3-carboxyphenyl | 29.9 | 3.6 | 0.27 ± 0.02 |
| 27 | phenyl-4-hydroxy-3-carboxyphenyl | 47.4 | 15.4 | none observed |
| 28 | (4-hydroxy-3,5-difluorophenyl)-3-carboxyphenyl | 38.5 | 3.5 | none observed |

TABLE 1-continued

Effects of Compounds on Fibril Formation

| Compound Number | Structure | % fibril formation (3.6 µM inhibitor) | % fibril formation (7.2 µM inhibitor) | Plasma Selectivity (equiv bound) |
|---|---|---|---|---|
| 29 | 3,5-difluoro-4-hydroxyphenyl-phenyl-4-carboxylic acid | 31.7 | 3.4 | 0.07 ± 0.02 |
| 30 | 3,5-dichloro-4-hydroxyphenyl-phenyl-3-carboxylic acid | 25.5 | 4.4 | 0.12 ± 0.02 |
| 31 | 3,5-dichloro-4-hydroxyphenyl-phenyl-4-carboxylic acid | 25.8 | 3.8 | 0.26 ± 0.04 |
| 32 | 2',4'-difluoro-4-hydroxy-3-(methoxycarbonyl)biphenyl | | 69.9 | |

TABLE 1-continued
Effects of Compounds on Fibril Formation
| Compound Number | Structure | % fibril formation (3.6 μM inhibitor) | % fibril formation (7.2 μM inhibitor) | Plasma Selectivity (equiv bound) |
|---|---|---|---|---|
| 33 | 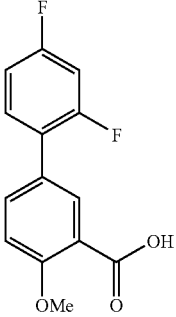 | | 38.5 | |
| 34 | 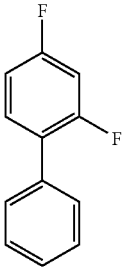 | | 100.0 | |
| 35 | 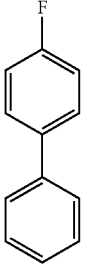 | | 100.0 | |
| 36 | 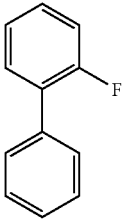 | | 99.4 | |
| 37 | 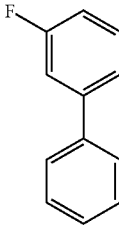 | | 100.0 | |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
|---|---|---|---|---|
| 38 | 3,5-dichloro-biphenyl | | 52.2 | |
| 39 | 3',5'-dichloro-biphenyl-3-carbaldehyde | 30.6 | 4.4 | 1.30 ± 0.15 |
| 40 | 3',5'-dichloro-biphenyl-4-carbaldehyde | | 25.4 | |
| 41 | 3',5'-dichloro-biphenyl-2-carbaldehyde | 34.5 | 7.1 | 1.96 ± 0.11 |
| 42 | biphenyl-3-carbaldehyde | | 35.4 | |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
|---|---|---|---|---|
| 43 | biphenyl-4-carbaldehyde | | 93.5 | |
| 44 | biphenyl-2-carbaldehyde | | 72.5 | |
| 45 | 3',5'-dichloro-biphenyl-3-carboxylic acid | 32.7 | 3.0 | 0.80 ± 0.08 |
| 46 | 3',5'-dichloro-biphenyl-4-carboxylic acid | 41.2 | 4.9 | 1.56 ± 0.01 |
| 47 | 3',5'-dichloro-biphenyl-2-carboxylic acid | | 45.4 | |

TABLE 1-continued

Effects of Compounds on Fibril Formation

| Compound Number | Structure | % fibril formation (3.6 μM inhibitor) | % fibril formation (7.2 μM inhibitor) | Plasma Selectivity (equiv bound) |
|---|---|---|---|---|
| 48 | 3,5-dichloro-biphenyl-3-methanol | 30.0 | 3.3 | 0.89 ± 0.09 |
| 49 | 3,5-dichloro-biphenyl-4-methanol | 38.9 | 5.9 | 0.54 ± 0.10 |
| 50 | 3,5-dichloro-biphenyl-2-methanol | 33.6 | 7.7 | none observed |
| 51 | biphenyl-3-methanol | | 85.5 | |
| 52 | biphenyl-4-methanol | | 100.0 | |

TABLE 1-continued

Effects of Compounds on Fibril Formation

| Compound Number | Structure | % fibril formation (3.6 µM inhibitor) | % fibril formation (7.2 µM inhibitor) | Plasma Selectivity (equiv bound) |
|---|---|---|---|---|
| 53 | 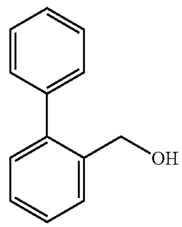 | | 81.0 | |
| 54 | 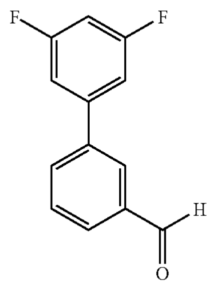 | | 64.3 | |
| 55 | 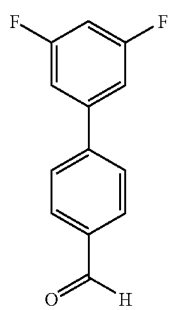 | | 69.6 | |

Based on the inhibitor efficacy data for compounds 2-55, it appears that a carboxylate-substituted hydrophilic ring directly connected to a di-halogen functionalized hydrophobic ring is sufficient for excellent activity (Table 1). A phenolic substituent in lieu of a carboxylate (2-10) yields considerably less active inhibitors, far inferior to the parent compound 1. Inhibitors having a halogen in the ortho or meta position of the hydrophobic ring are superior to compounds lacking halogens or those having a single para halogen. This suggests that para halogens do not compliment the HBPs in the same manner as meta and ortho halogenated biaryls. Complete removal of all halogens can result in a poor inhibitor, presumably due to the lack of steric complimentarity to fill the halogen binding pockets (for example, compounds 10, 21-22, 27, 42-44, and 51-53). Under the conditions tested, the best phenolic compound (8) is inferior to 1, which bears both a phenolic and carboxylate functionality on the hydrophilic ring. Biaryl compounds stabilized with a single carboxylate (such as 11-22) can be excellent amyloid fibril inhibitors, for example, compounds 11, 12, 15-20. These rival diflunisal for inhibition, the exception being those containing only a para halogen (e.g., compounds 13 and 14). A meta or para substituted aryl carboxylate can be sufficient for endowing excellent inhibition properties, suggesting that the hydroxyl substituent in 1 is not required for good inhibitor activity. In addition, para carboxylate positioning appears to afford superior inhibitors, suggesting that a para carboxylate is better able to take advantage of electrostatic interactions with the ε-ammonium groups of Lys 15 and 15' (forward binding mode), as in the case of 20, or hydrogen bonding interactions with the Ser 117 and 117' hydroxyl groups (reverse binding mode) as in the case of 18. Biaryls wherein the hydrophobic ring is substituted with halogens in positions other than the para position and the hydrophilic ring with meta and particularly para carboxylates yield highly efficacious TTR amyloid fibril formation inhibitors.

Addition of a hydroxyl substituent to the ring containing a carboxylate substituent (the salicylic acid substitution, for example, 23-27) can also result in inhibitors with high activity similar to diflunisal. In biaryls with the salicylic acid core, the exact positioning of the halogens does not appear to be as vital as in the previous cases, suggesting that this ring contributes disproportionately to the binding energy. The para hydroxyl may participate in hydrogen bonding with the ε-ammonium groups of Lys 15 and 15' (forward binding mode) or with the Ser 117 and 117' hydroxyls (reverse binding mode). Substitution of fluorine in 1 with chlorine (26) can result in an inhibitor with equal or superior activity, whereas complete removal of the halogens (27) can result in a modest inhibitor. It should be noted that 27 is only slightly superior to a para carboxylate 22 in vitro, and both are superior to the halogen-free inhibitors with the carboxylate in the meta position, 21, and the hydroxyl-containing analog 10.

Inclusion of a 3',5'-dihalo-4'-hydroxyl substituent on the halogen-containing ring, with carboxylates in either the para or meta positions (28-31) can result in high inhibitory activity, similar to diflunisal. The 4-hydroxyl substitution was included to more closely mimic thyroxine, the natural ligand of TTR. These inhibitors may also more closely mimic the hormone activity of thyroxine and therefore may act as thyroid agonists or antagonists, an effect that can be undesirable.

Protection of the carboxylate as a methyl ester or the hydroxyl as a methyl ether (32 and 33) can result in inferior inhibitors compared to 1. A combination of the loss of charge and the increase in steric bulk probably explains these observations. Removal of all hydrophilic substituents (e.g., 34-38) can result in poor inhibitors. A biaryl compound containing only meta chlorine substitution (e.g., 38) can be a modest inhibitor, suggesting that the chlorines make enhanced contacts in the halogen binding pockets as compared to fluorine-containing biaryls (37).

Several chlorine-containing inhibitors were synthesized and their TTR fibril inhibition activity evaluated. When members of this class of inhibitors contain carboxylates in the meta or para positions (e.g., 45 and 46) they can possess high activity, whereas those having an ortho carboxylate (such as 47) can be an inferior inhibitor. This observation suggests that the ortho carboxylate may be too far from the Lys 15 and 15' ε-ammonium groups to make favorable electrostatic interactions (forward binding mode) or from the Ser 117 and 117' hydroxyl groups to undergo hydrogen bonding interactions (reverse binding mode). Benzylic alcohols 48-50 surprisingly proved to be excellent inhibitors of fibril formation. The meta dichloro substitution on one ring appears to be complemented by benzyl alcohol functionality in either the ortho, meta or para position, potentially due to the hydrogen bonding or water-mediated hydrogen bonding. A series of aldehyde analogs (39-41) where the —$CH_2OH$ groups were replaced by an aldehyde functionality, showed good inhibition except in the case of the para aldehyde 41, possibly owing to hydration of the aldehyde to a gem diol. It is possible that the aldehydes, the benzylic alcohols and the carboxylates bind in the pocket via a different mechanism. In the absence of structural information, however, a similar binding mode cannot be ruled out. It is also possible that the aldehydes bind covalently either to Ser 117 (117') via a hemiacetal or to Lys 15 (15') via an imine bond. Substitution of the chlorines with fluorines (54 and 55) in the case of the aldehydes can result in rather poor inhibitors (39 and 41). As before, complete removal of the halogens can result in inhibitors with poor activity (42 and 44), except in the case of the meta aldehyde 43 where the activity is modest. This modest activity may result from a high degree of hydration. It is surprising that the 3',5'-difluoro-meta aldehyde (54), is inferior to the aldehyde lacking halogens (42).

Inhibitors that keep TTR fibril formation below 50% at a concentration equal to that of TTR (3.6 μM) were further evaluated for their ability to bind TTR selectively over all other proteins in blood plasma. The diflunisal concentration in blood can exceed 30 μM 20 h after a single 500 mg dose, or 300 μM 4 h after the same dose. While this high level of sustained plasma concentration suggests excellent bioavailability, more selective inhibitors will allow for lower dosing and potentially fewer side-effects; therefore, human plasma was incubated with this subset of inhibitors at a final concentration of 10.8 μM (average TTR concentration in human plasma is approximately 5 μM). TTR was then captured using a resin-bound antibody, and the immobilized TTR was washed three times with a solution of TSA (tris saline)/0.05% saponin, followed by two washes with TSA. The TTR-inhibitor complex was liberated from the resin with 100 mM triethylamine (pH 11.5), and the stoichiometry of inhibitor present relative to TTR was determined by reverse-phase HPLC analysis. A maximum of 2 equiv of inhibitor may be bound per TTR tetramer. The post-wash plasma binding stoichiometries, representing lower limits owing to wash-associated losses, are summarized in Table 1.

Chlorine-containing biphenyls can be selective for binding TTR in human blood plasma (average stoichiometry of 0.8, with a theoretical maximum stoichiometry of 2.0, see Table 1). The average stoichiometry observed was 0.4 for all inhibitors tested. Of the fluorine-containing inhibitors, 18 and 20 exhibited very good and acceptable binding selectivity for TTR, respectively, superior to the 0.13 stoichiometry displayed by 1 under similar conditions. The stoichiometry values reported in Table 1 can represent a lower limit due to wash-associated losses of the inhibitor from the TTR sequestered on a polyclonal antibody resin. The TTR binding selectivity results for 39 and 41 should be considered with caution, because these compounds may be covalently attached to TTR, as discussed above.

Those inhibitors that exhibit excellent TTR amyloid fibril inhibition data in vitro, yet display poor plasma selectivity, may bind preferentially to the drug-binding sites in albumin and/or similar sites in other proteins found in plasma. It can be unlikely that such inhibitors will prevent TTR misfolding and amyloidosis in a complex environment like that of blood plasma or CSF.

High-resolution X-ray co-crystal structures of 1 and three of its analogs 26, 18, and 20 bound to TTR were obtained by soaking TTR crystals with a 10-fold molar excess of inhibitor for more than three weeks. The crystallographic statistics are summarized in Table 2.

TABLE 2

Crystallographic Statistics

|  | TTR•1 | TTR•18 | TTR•20 | TTR•26 |
|---|---|---|---|---|
| Data collection |  |  |  |  |
| Resolution (Å) | 35.58-1.85 | 42.18-1.54 | 64.5-1.7 | 51.30-1.7 |
| No of unique reflections | 20,478 | 33,741 | 25,634 | 25,486 |
| Completeness (%) (Overall/outer shell) | 98.4/99.0 | 95.0/98.0 | 98.0/99.0 | 99.0/98.0 |
| $R_{sym}$ (Overall/outer shell) | 0.09/0.31 | 0.03/0.32 | 0.08/0.39 | 0.07/0.40 |
| Refinement |  |  |  |  |
| Resolution (Å) | 35.58-1.85 | 42.18-1.50 | 64.5-1.7 | 51.30-1.7 |
| R-factor/R-free (%) | 21.2/23.6 | 22.2/24.5 | 22.5/24.0 | 21.5/24.2 |
| Rmsd bond length (Å) | 0.03 | 0.06 | 0.02 | 0.02 |
| Rmsd bond angles (°) | 2.3 | 2.7 | 1.9 | 1.9 |

Diflunisal (1) binds to TTR in both forward and reverse modes. In each hormone-binding site of TTR, four different binding conformations of diflunisal were found with approximately equal occupancy—a forward and reverse binding mode each with two symmetrically equivalent binding modes. The biaryl system of diflunisal was shifted away from the center of the hormone binding pocket and occupies two distinct positions to form a 'V' shaped cone of electron density in the hormone-binding pocket of TTR. This mode of binding enhances both hydrophobic and van der Waals interactions between the inhibitor and the hydrophobic pocket of TTR formed by Leu17, Ala 108, Leu 110, Thr 119 and Val 121. The reverse binding mode of diflunisal was augmented by the hydrogen bond interaction between the carboxyl group and the side chain oxygen of Thr 119 and the main chain oxygen of Ala 108 in the inner binding pocket. Surprisingly Ser 117 neither takes up multiple conformations nor forms any electrostatic interaction with the inhibitor. In the reverse mode of binding, one of the fluorine substituents of diflunisal was within hydrogen bonding distance from the Thr 119 side chain oxygen (3.3 Å). In the outer binding pocket, the electron density for the side chain atoms of Lys 15' was visible only at low sigma level indicating it may be in more than one conformation. The best possible conformation for the Lys 15 residue was modeled at a hydrogen bonding distance from the carboxyl group of diflunisal in the forward binding mode.

Compound 20 binds to TTR in the forward binding mode, with the carboxylate-substituted hydrophilic ring oriented in the outer binding pocket to interact electrostatically with Lys 15 and 15'. The fluorinated aryl ring is positioned in the inner binding pocket wherein the halogens are placed in HBP 2 and 2'. Interestingly, close inspection of both binding sites reveals a significant difference in the orientation of the biphenyl rings. The angles between the planes of the phenyl rings vary from 32.6 degrees in one binding site to 63.8 degrees in the other. This observation may be a result of the negatively cooperative binding of 20 with TTR.

Compound 18 binds to TTR in the reverse mode with the carboxylate-substituted hydrophilic aryl ring oriented into the inner pocket, within hydrogen bonding distance of Ser 117 and Ser 117'. The aryl rings are rotated 34 degrees with respect to one another to take advantage of hydrophobic interactions with Leu 17, Ala 108, Val 121 and Thr 119. The fluorines are positioned in halogen binding pockets 1 and 1'. The reverse binding mode was not expected, instead, the carboxylate was envisioned to be positioned in the outer pocket to take advantage of electrostatic interactions with Lys 15 and 15', with the fluorines sequestered into halogen binding pockets 2 and 2'. However, the reverse binding mode was not a total surprise, as it was observed previously for diclofenac (a biaryl amine) and several diclofenac analogs.

Substitution of chlorines in place of fluorines in diflunisal induces significant differences in the binding of 26 to TTR. Compound 26 binds to TTR in the reverse binding mode with the carboxyl-substituted aryl ring oriented in the inner binding pocket and chlorines sequestered into halogen binding pockets 2 and 2'. Like 18 and 20, compound 26 also occupies the center of the hormone-binding pocket. The residues Ala 108, Lys15, Leu 17, Leu 110, Lys 17 and Thr 119 of TTR protomers forms van der Waals and hydrophobic interactions with the inhibitor. In the inner binding pocket, the side chain of Ser 117 exists in two conformations to interact with the carboxyl substitution of 26 and Ser 117 of the other monomers. The same carboxyl oxygen of 26 also forms a hydrogen bond interaction with the main chain oxygen of Ser 117. The other carboxyl oxygen of 26 forms a hydrogen bond with the main chain oxygen of Ala 108. In contrast to diflunisal, the Thr 119 residue orients away from the inhibitor, contributing to the hydrophobicity of the binding pocket rather than hydrogen bonding with the inhibitor.

Figure 2A:
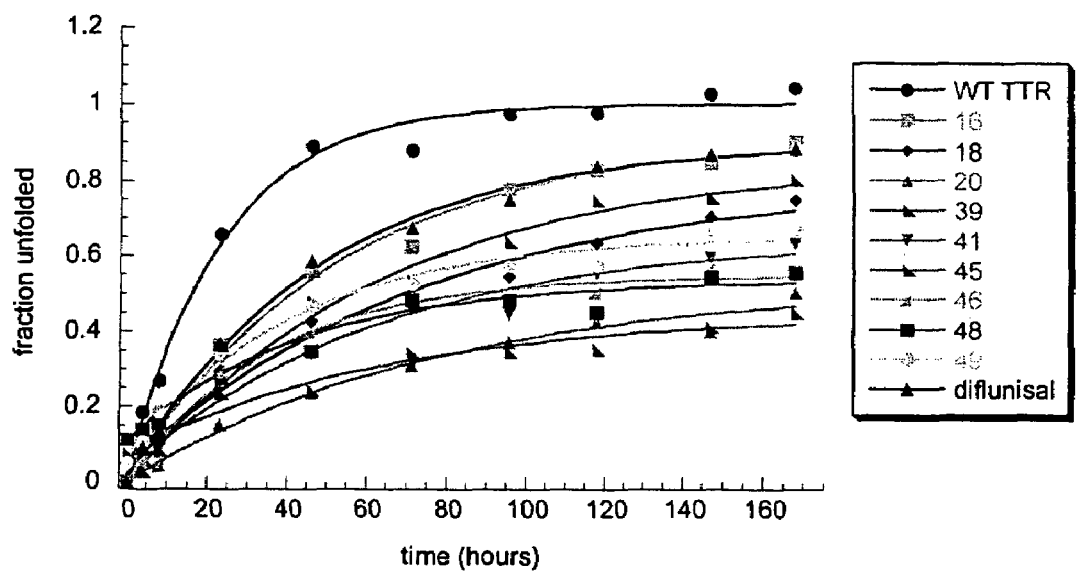
FIGS. 2A and 2B are graphs depicting the time course of transthyretin unfolding in the presence of different inhibitors.
Figure 2B:
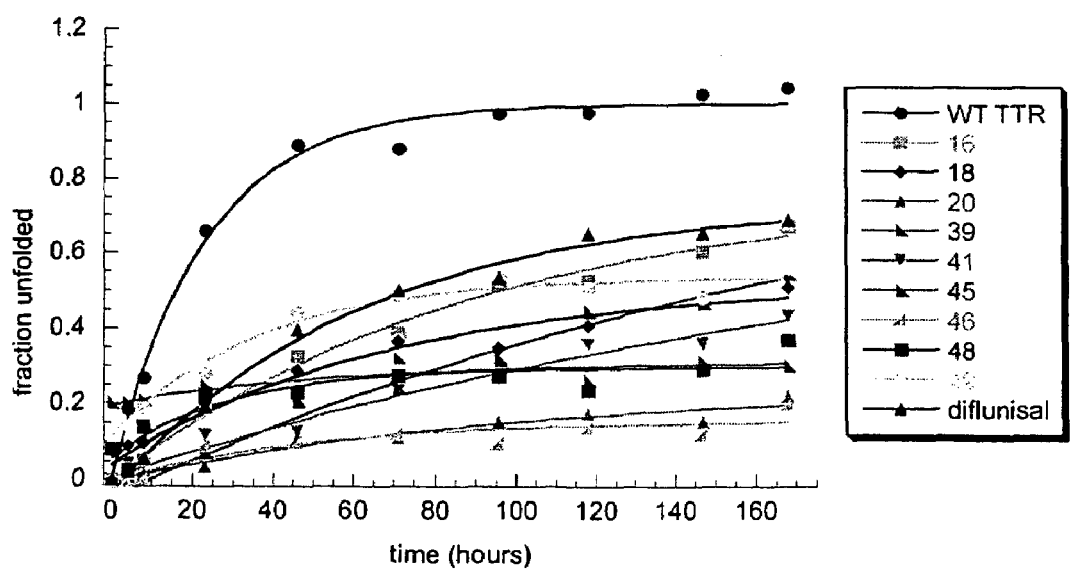
Figure 3A:
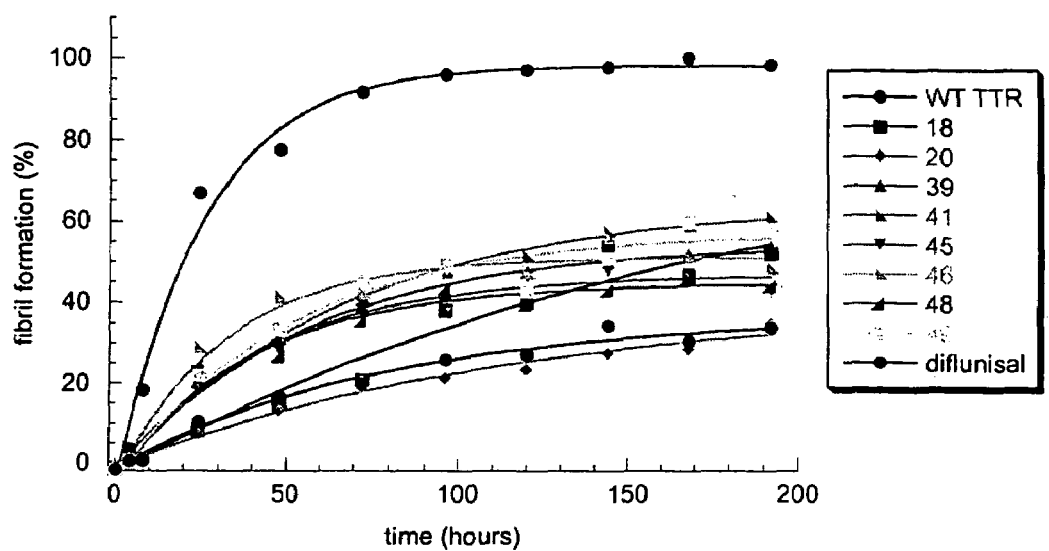
FIGS. 3A and 3B are graphs depicting the time course of fibril formation in the presence of different inhibitors.
Figure 3B:
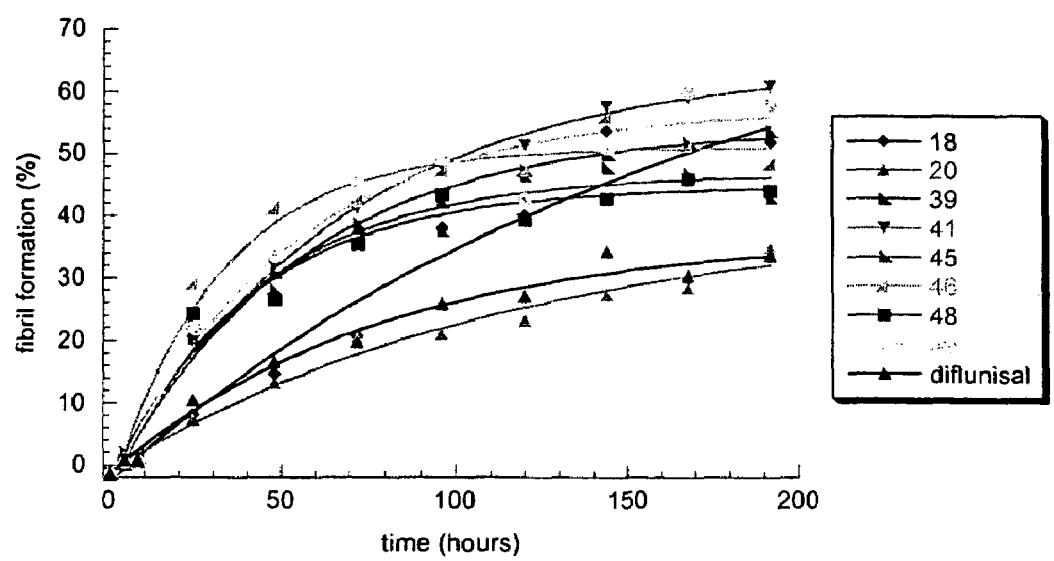

To further probe the mechanism of action of these inhibitors, their ability to stabilize TTR against urea-induced dissociation as a function of time was evaluated. The rate of tetramer dissociation was linked irreversibly to fast, easily monitored, monomer unfolding employing urea concentrations exceeding those that enable monomer refolding. Unfolding-monitored dissociation was probed by far UV-CD in 6.5 M urea revealing that all the good inhibitors of acid-mediated amyloidogenesis slowed the rate of tetramer dissociation in a dose-dependent fashion (FIGS. 2A and 2B). Several inhibitors, including 20, 46 and 48, show a dramatic effect on dissociation of the TTR tetramer, the rate-limiting step of amyloidogenesis. See, for example, Hammarstrom, P.; et al. *Proc. Natl. Acad. Sci. U.S.A.* 2002, 25, 16427-32, which is incorporated by reference in its entirety.

Since the mode of inhibition of TTR fibril formation by these compounds is suspected to be dose-dependent tuning of the tetramer dissociation barrier through ground-state stabilization, the best inhibitors should slow tetramer dissociation the most. The rate of fibril formation was monitored by turbidity at a final pH of 4.4 over 192 h. See FIGS. 3A, 3B, 4A and 4B. Inhibitors possessing the ability to stabilize tetrameric TTR at low pH will prevent tetramer dissociation, misfolding and misassembly into amyloid. The best inhibitors of amyloid fibril formation are those that slow tetramer dissociation the most (FIGS. 2A and 2B). however, the correlation is not perfect, as some inhibitors bind better in urea than in acidic conditions and vice versa.

To ensure that the inhibitors are stabilizing the tetrameric form of TTR (3.6 μM), the quaternary structure of TTR was probed with equilibrium and velocity analytical ultracentrifugation studies. The quaternary structure of the protein after 72 h incubation with 18 and 20 (3.6 μM or 7.2 μM) at pH 4.4 was determined. The tetramer was the dominant species, both at 3.6 μM and 7.2 μM inhibitor concentration in equilibrium AUC as well as in velocity studies.

Isothermal titration calorimetry (ITC) was employed to determine the binding constants of 18 and 20 to TTR at pH 8.0 (25° C.). Diflunisal and the two analogs bind to TTR with negative cooperativity, a characteristic displayed by many other ligands. Binding at the first site is 15 times stronger than binding at the second site in the case of diflunisal and 20. Biaryl 18 possesses a $K_{d1}$ approximately 120 times lower than $K_{d2}$ (Table 3). Table 3 summarizes the first and second dissociation constants for the binding of 1, 18 and 20 to wild type TTR determined by ITC. The binding constants for 1 were reported previously, and are provided here for comparison purposes. See Example 1.

TABLE 3

Dissociation Constants for Compounds Binding to Wild Type TTR

| Inhibitor | $K_{d1}$ | $K_{d2}$ |
|---|---|---|
| 1 | 75 nM | 1100 nM |
| 18 | 9 nM | 1100 nM |
| 20 | 80 nM | 1300 nM |

Tetrameric WT TTR dissociates with a $t_{1/2}$ of 42 h, and unfolds 500,000 times faster. Hence, its rate of dissociation can be probed by linking it to unfolding, which is irreversible in 6.5 M urea. Since tetramer dissociation is rate-limiting for amyloidogenesis, all inhibitors displaying excellent in vitro activity and binding stoichiometry exceeding 0.50 in plasma should slow tetramer dissociation if the presumed mechanism of action, kinetic stabilization by selective binding to the native state, is correct (see FIGS. 2A and 2B).

TTR tetramer dissociation rates were measured as a function of inhibitor concentration over a 168 h time-course in 6.5 M urea. Select inhibitors, specifically 18, 20, 39, 41, 45, 46, 48 and 49 demonstrate an overall reduction in the extent of tetramer dissociation over 160 h as reflected in the amplitude changes relative to TTR without inhibitor. The rate of tetramer dissociation is also dramatically slowed in the presence of inhibitor, as reflected in the decrease in the slope of the time course. Inhibitors 20, 45, 46 and 48 are superior, presumably because the inhibitor dissociates very slowly from TTR·I and TTR·$I_2$ due to their high binding affinity in urea. The formation of TTR·I and TTR·$I_2$ can significantly stabilize the native state due to the low $K_d$s of such complexes, and raise the kinetic barrier for tetramer dissociation, substantially in the case of 20, 45, 46 and 48. Even though 16 and 18 bind to TTR, it appears that their affinity is insufficient to affect kinetic stabilization. It is likely significant that the rank ordering of inhibitor efficacy in urea at an inhibitor concentration of 3.6 μM (3.6 μM protein) is 20≈45>46≈48, which is different than an inhibitor concentration of 7.2 μM (20≈46>46≈48). This likely reflects a difference in the $K_{d2}$ values in urea.

Kinetic stabilization of the native state is an attractive therapeutic strategy due to the emerging evidence that misfolded oligomers, whether on the amyloid pathway or off it, are neurotoxic. Achieving kinetic stabilization with inhibitors can provide a non-invasive treatment for SSA, FAP and FAC.

Figure 4A:
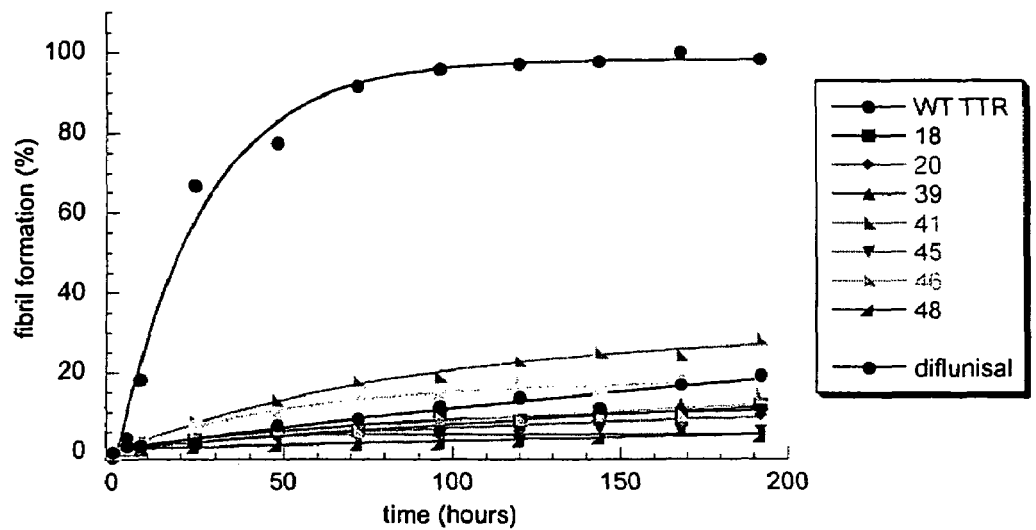
FIGS. 4A and 4B are graphs depicting the time course of fibril formation in the presence of different inhibitors.
Figure 4B:
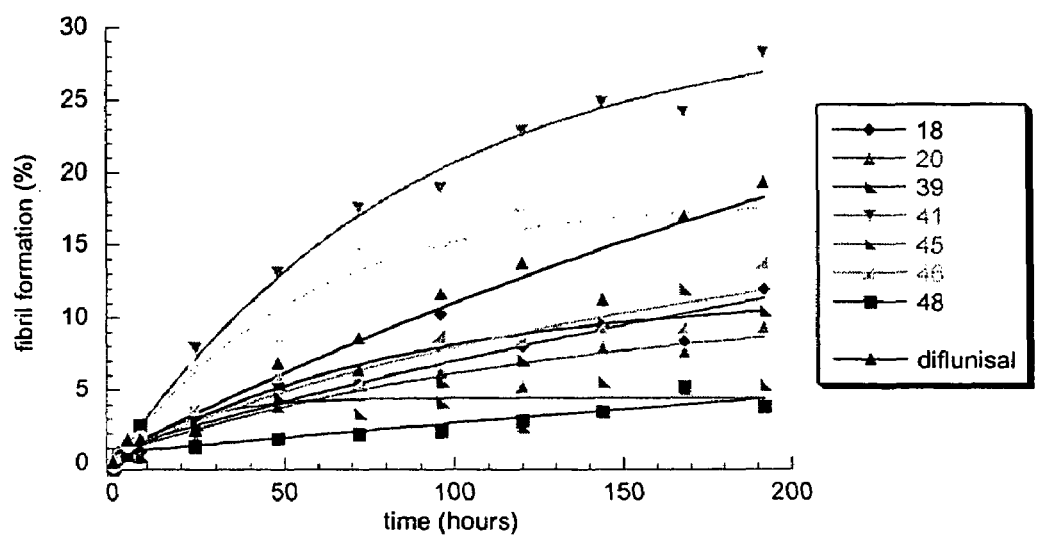

Tetramer dissociation rates in urea in the presence of a given inhibitor do not always predict the ability of the inhibitor to prevent amyloidosis at low pH. Since it is not yet clear how and where amyloid forms in a human, TTR tetramer stabilizers that function well in a variety of denaturing environments are desirable. The rate of TTR fibril formation as a function of inhibitor concentration was explored under acidic conditions (FIGS. 3A, 3B, 4A and 4B). Inhibitors 20, 45 and 48 perform exceptionally well in this environment as well. Inhibitor 46 is a better tetramer stabilizer in urea than in acid, whereas 1 is much better in acid than in urea. The free energy of stabilization associated with the formation of the TTR·I and TTR·$I_2$ complexes in a given environment determines the extent of ground-state stabilization and associated increase in activation free energy for tetramer dissociation. These data suggest that the inhibitors slow TTR amyloidosis at low pH much more efficiently than they slow TTR tetramer dissociation in 6.5 M urea. This may be because amyloidogenesis requires concentration-dependent reassembly after dissociation. The more effective inhibitors are those that can keep the concentration of the monomeric amyloidogenic intermediate of TTR at low enough levels to make fibril formation very inefficient. As observed in the urea denaturation of TTR in the presence of inhibitors, the rank ordering of inhibitor efficacy at low pH differs significantly from 3.6 μM inhibitor (FIGS. 3A and 3B) to 7.2 μM inhibitor concentration (FIGS. 4A and 4B). This observation likely reflects the differences in $K_{d2}$ values of each of the inhibitors at low pH. The most dramatic example is that of diflunisal—one of the most efficacious inhibitors of fibril formation at 3.6 μM, but one of the least efficacious at 7.2 μM, owing to its relatively high $K_{d2}$.

The diflunisal analogs represent a promising class of compounds for the treatment of TTR amyloidosis. While several diclofenac analogs are very good inhibitors of fibril formation, the diflunisal analogs offer an additional class of highly effective TTR tetramer stabilizers. Several diclofenac analogs offer the ability to inhibit fibril formation resulting from the dissociation and misfolding of two TTR mutants—Val30Met and Leu55Pro. X-ray co-crystal structures demonstrate that the diclofenac analogs primarily bind in the reverse binding mode, however, minor perturbations in the structures of the diflunisal analogs allow for either forward or reverse binding. In addition, diflunisal is able to bind either in the forward or the reverse binding mode, with almost equal occupancy in both modes. The dissociation constants obtained for diclofenac (60 nM for $K_{d1}$ and 1200 nM for $K_{d2}$) were comparable to those obtained for diflunisal and 20, with 18 demonstrating nearly 10-fold tighter binding for the first binding event as illustrated by its $K_{d1}$ value. In addition, both inhibitor classes displayed negatively cooperative binding. Most remarkably, several diflunisal analogs were very selective for TTR in human blood plasma, offering the potential for decreased toxicity and side-effects. See Oza, V. B.; et al. J. Med. Chem. 2002, 45, 321-32.

Twenty eight of the compounds synthesized can substantially inhibit TTR amyloidogenesis. Of those, several showed binding stoichiometry exceeding 0.50 equiv in human blood plasma. Both the chlorinated and fluorinated aryl substructures of the better inhibitors are found in known drugs, therefore, there is good reason to believe that these compounds or their analogs could be evolved into drugs that do not display the NSAID activity of 1. The fluorinated compounds 18 and 20 can bind to and stabilize tetrameric TTR in 6.5 M urea, dramatically slowing the first step of misfolding and amyloidogenesis, dissociation of the TTR tetramer. These compounds, and others, also dramatically slow acid-mediated TTR amyloidogenesis. Of the compounds tested, 18, 20, 39, 41, 45, 46, 48 and 49 performed best at stabilizing the TTR tetramer in urea and under acidic conditions. These biaryl compounds appear to increase the activation barrier associated with tetramer dissociation, the rate-limiting step for amyloid formation, by ground-state stabilization.

Example 3

Orally Administered Diflunisal Stabilizes Transthyretin Against Denaturation

Transthyretin (TTR) is a homotetrameric protein that transports thyroxine and holo-retinol binding protein. Under denaturing conditions, rate limiting tetramer dissociation and rapid monomer misfolding enables misassembly into amyloid-causing senile systemic amyloidosis, familial amyloid polyneuropathy, and familial amyloid cardiomyopathy. Diflunisal binding to at least one of the two unoccupied thyroxine binding sites in TTR is known to stabilize the TTR tetramer also increasing the dissociation activation barrier in vitro. The feasibility of using diflunisal for the treatment of TTR amyloidosis was investigated.

Methods

Thirty healthy volunteers (25 male, 5 female) were enrolled after informed consent was given. The subjects ranged from 23 to 53 years of age (mean age, 37.6±8.8) with a mean body weight of 78.0±12.1 kg. Each subject was treated with diflunisal (Dolobid®) at a dose of 125, 250 or 500 mg twice a day (every 12 hrs) for 7 days (13 total doses). Blood was collected on day 1 before treatment and on day 8, 4 and 12 h after diflunisal intake. This study design was approved by the Human Subjects Committee of Scripps Clinic, Scripps Green Hospital, The Scripps Research Institute, and The Scripps General Clinical Research Center.

Serum diflunisal levels were measured. One hundred μL of serum was added to 900 μL of acetonitrile to precipitate the proteins. Following centrifugation, 100 μL of supernatant was added to 900 μL of 100 mM aqueous triethylamine, pH 11.5. After filtration, 100 μL of each sample was injected on a Keystone 3-cm C18 reverse-phase column using a 40-100% gradient of solution B over 10 min (solution A: 94.8% water/5% acetonitrile/0.2% trifluoroacetic acid; solution B: 94.8% acetonitrile/5% water/0.2% trifluoroacetic acid), controlled by a Waters 600E multisolvent delivery system. Detection was accomplished at 280 nm with a Waters 486 tunable absorbance detector, and the peaks were integrated to give the concentration of diflunisal from standard curves.

Stoichiometry of diflunisal binding to TTR in human serum was analyzed. A 1:1 gel/10 mM Tris.HCl, pH 8.0/140 mM NaCl/0.025% $NaN_3$(TSA) slurry (62.5 µL) of Sepharose was added to 500 µL of serum and incubated at 4° C. for 1 h. Following centrifugation, 400 µL of supernatant was added to 200 µL of a 1:1 gel/TSA slurry of the anti-TTR antibody-conjugated Sepharose and slowly rocked at 4° C. for 20 min. After centrifugation, the gel was washed with 1 mL of TSA/0.05% saponin (Fisher Scientific) (twice, 10 min each), and additionally with 1 mL of TSA (once, 10 min) at 4° C. Then 155 µL of 100 mM aqueous triethylamine, pH 11.5, was added to elute the TTR and bound diflunisal from the antibodies. After gentle rocking at 4° C. for 30 min, the sample was centrifuged and 145 µL of the supernatant was removed. A 135-µL injection of sample was separated and analyzed as described previously (Purkey et al., Proc Natl Acad Sci USA 2001; 98: 5566-71).

Serum TTR tetramer stability towards urea denaturation was evaluated. Ten µL samples of serum were incubated (25° C.) in 90 µL of various concentrations of urea in 50 mM phosphate buffer (pH 7.0; 100 mM KCl, 1 mM EDTA, 1 mM DTT). Urea solutions were checked by refractive index to verify the concentrations prepared by weight. Glutaraldehyde cross-linking of the protein was performed by adding 10 µL of glutaraldehyde (25%). The cross-linking reaction was allowed to proceed for 4 min before it was quenched by the addition of 10 µL of $NaBH_4$ (7% in 0.1 M NaOH). The samples were mixed with 120 µL of SDS reducing gel loading cocktail (final SDS concentration=2.5%) and boiled for 5 min. Samples were separated using 12% SDS-PAGE and the gels were analyzed by immunoblotting using anti-TTR antiserum (Purkey et al., supra).

Serum TTR tetramer stability against acid denaturation was evaluated. Ten µL samples of serum were incubated (37° C.) in 90 µL of 100 mM acidification buffer. Citrate buffer was used when a final pH of ≦3.8 was desired; acetate buffer was employed when the pH range under evaluation was 4.2-5.4. After cross-linking, samples were analyzed by SDS-PAGE and immunoblotting as described above.

Recombinant WT TTR and variants were expressed in BL21/DE3 Epicurian gold Escherichia coli (Stratagene) transformed with the pmmHα plasmid containing the TTR and ampicillin-resistance genes. Expression and purification were performed as described previously (Lashuel et al., Biochemistry 1999; 38: 13560-73).

Rate of TTR tetramer dissociation was measured by circular dichroism spectroscopy. The evaluation of tetramer dissociation rates was carried out using recombinant TTR (3.6 µM) samples in 6.5 M urea, a concentration in the post-transition region for tertiary structural change (Hammarström et al., Proc Natl Acad Sci USA 2002; 99: 16427-32). The far —UV CD spectra of TTR (210-220 nm) as a function of time was measured to evaluate the slow tetramer dissociation rate by linking it to fast tertiary structural changes.

Fibril formation assay was carried out as follows. A recombinant TTR stock solution (7.2 µM) was diluted 1:1 with 100 mM acidification buffer. Citrate buffer was used when a final pH of ≦3.8 was desired; acetate buffer was employed when the pH range under evaluation was 4.2-6.0, and phosphate buffer was utilized for evaluating amyloidogenesis at pH 6.5. Samples were incubated at 37° C. for 72 h without stirring after acidification. The extent of fibril formation was probed by turbidity measurements at 400 nm.

Fibril formation kinetics were measured as follows. Solutions of recombinant TTR (7.2 µM) were mixed with an equal volume of 100 mM acetate buffer to yield a final pH of 4.4. The samples were incubated at 37° C. and the turbidity at 400 nm was monitored over the course of 168 h. A separate sample was made up for each time point.

The effect of diflunisal on urea-mediated tetramer dissociation and pH-mediated fibril formation was evaluated by adding diflunisal to a TTR solution which was incubated for 3 h (37° C.) before subjecting the protein to urea denaturation or pH-mediated amyloidosis.

Results

The mean serum diflunisal concentrations, measured by HPLC, 4 and 12 h after intake of the $13^{th}$ dose were 20.1±7.1 and 6.9±3.0 µM in the 125 mg bid group, 233.5±76.0 and 145.8±38.9 µM in the 250 mg bid group, and 517.0±79.5 and 421.9±78.1 µM in the 500 mg bid group. Greater than 99% of diflunisal is protein bound. These concentrations observed in 250 mg bid and 500 mg bid group are very high relative to the TTR concentration in serum (3.6-7.2 µM) and should yield a diflunisal binding stoichiometry approaching the maximum of 2 if binding to competitor proteins such as TBG (0.3-0.5 µM) and/or albumin (580-725 µM), which has multiple binding sites for small molecules, is not of high affinity.

Diflunisal preferably binds tetrameric TTR in blood with stoichiometry of at least 1 and ideally 2 to observe maximum kinetic stabilization. To place a lower limit on diflunisal stoichiometry in each subject, we immunoprecipitated transthyretin from serum with polyclonal antibodies bound to a solid phase resin as described previously (Purkey et al., supra). After washing immobilized TTR 3× to eliminate non-specific binding, the TTR-diflunisal complex was dissociated from the resin and the diflunisal stoichiometry was determined by HPLC employing standard curves. The stoichiometry of diflunisal bound to TTR in serum 4 and 12 h after intake was 0.45±0.11 and 0.31±0.12 in the 125 mg bid group, 1.12±0.08 and 0.95±0.13 in the 250 mg bid group and 1.51±0.09 and 1.48±0.08 in the 500 mg bid group. Diflunisal stoichiometry increased with its serum concentration, up to ≈300 µM. The lower than expected maximal stoichiometry of 1.5 at a serum concentration of 300 µM either results from a limitation of the method (wash-associated losses) and/or diflunisal binding to other plasma proteins, therefore we carried out a diflunisal binding stoichiometry study with recombinant TTR. Wash-associated losses explain the maximum binding stoichiometry of 1.5 owing primarily to dissociation from the low affinity site. Diflunisal binds to TTR with negative cooperativity, hence dissociation from the low affinity site is dramatically faster. The expected binding stoichiometry in buffer was calculated based on the dissociation constants determined by isothermal titration calorimetry ($K_{d1}$, 75 nM; $K_{d2}$, 1.1 µM). Coplotting the calculated and experimentally determined stoichiometry, the latter derived from immunoprecipitation (3 washes) and HPLC analysis, allows one to estimate the true stoichiometry at 1.75-1.91 at 250 mg bid, suggesting that this dose could be utilized.

A comparison of diflunisal (100 µM) binding stoichiometry in subjects (0.8-1) to recombinant TTR (1.5) reveals significant binding to serum proteins besides TTR, providing the incentive to develop diflunisal analogs that bind more selectively to TTR. The serum level of TTR was increased and the serum levels of total $T_4$ and RBP were decreased after diflunisal administration in all groups. These findings suggest that diflunisal influences TTR metabolism. No obvious side effects were observed during or after the study. However, the serum level of albumin was decreased significantly and the levels of BUN and creatinine were increased slightly in the 500 mg bid group. In the 250 mg bid group, the serum level of albumin was decreased moderately and the level of BUN was increased slightly.

A new method was developed to demonstrate that orally administered diflunisal stabilizes serum TTR against denaturation stresses including amyloidosis. This method serves as a surrogate marker to identify compounds that should prevent TTR misfolding diseases. Whole serum from the subjects was subjected to denaturation either by adding urea (0-9 M) or by adding acid (pH 3.8-5.4). Since TTR must dissociate in order to denature, quaternary structural changes can be used to monitor the extent of unfolding (Hammarstrom et al, supra). Glutaraldehyde was added to crosslink all the proteins in serum after being subjected to a denaturation stress and to establish what fraction of TTR is normally folded (tetramer or dimer) versus denatured (monomer). SDS-PAGE of whole serum separates the crosslinked TTR tetramer and dimer (these representing folded TTR) from the monomer. Immunoblotting enables quantitative comparisons of the amount of folded TTR. The polyclonal antibodies do not bind to the unfolded TTR monomer nearly as well as folded TTR, therefore it is most useful to compare the intensity of the tetramer and dimer bands in the absence and presence of diflunisal. The time dependence of diflunisal inhibition of TTR denaturation can also be evaluated by this method. The barely noticeable time dependence of this process in the presence of diflunisal strongly supports the kinetic stabilization mechanism (see Example 1) wherein ground state stabilization by diflunisal makes the tetramer dissociation barrier insurmountable. The efficacy of the diflunisal (250 mg bid) in these denaturation time courses is better than the measured stoichiometry (0.8-1.2) would predict, providing further evidence that the immunoprecipitation method underestimates the actual binding stoichiometry, especially when it exceeds 1.

Knowing the range of diflunisal binding stoichiometries in humans and the concentration of diflunisal required to mimic those stoichiometries in a test tube allows for the carrying out of relevant in vitro biophysical studies to probe the mechanism by which the TTR•diflunisal and TTR•diflunisal$_2$ complexes prevent dissociation and amyloidosis. The rate of urea-mediated (6.5 M) dissociation and the rate of acid mediated (pH 4.4) amyloid fibril formation were studied as a function of diflunisal concentration (5, 10, 20 and 60 μM), revealing dose dependent slowing. Since tetramer dissociation is rate limiting for amyloid fibril formation, it follows that tetramer dissociation rates in urea should be predictive of the extent of amyloid fibril formation mediated by acidification. Diflunisal is better at inhibiting amyloidosis than inhibiting urea mediated dissociation because concentration dependent reassembly is also required for amyloidosis. It is also possible that $K_{d1}$ and $K_{d2}$ associated with diflunisal binding to TTR are lower in acid than in urea.

More than 80 TTR mutations predispose individuals to hereditary amyloidosis by sequence dependent alterations of the denaturation energy landscape. Of these, the amyloid deposition of V122I results in familial amyloid cardiomyopathy (FAC) in 3-4% of African Americans, whereas V30M is the prominent familial amyloid polyneuropathy (FAP) mutation. Diflunisal inhibits both V122I and V30M amyloidogenesis in a dose dependent fashion, demonstrating the generality of this approach.

It is highly desirable to develop a general, non-invasive therapeutic strategy to ameliorate TTR amyloidosis. The results outlined herein indicate that oral administration of diflunisal can slow tetramer dissociation by binding to and stabilizing the non-amyloidogenic native state. Native state stabilization is a particularly attractive strategy given recent reports that misfolded oligomers and not amyloid fibrils cause neurodegeneration. Clinical use of diflunisal (250-500 mg bid) for rheumatoid arthritis and osteoarthritis demonstrate its low toxicity for long-term uses. TTR's serum half-life is 12-15 h, therefore twice daily dosing seems optimal given the 8-10 h half-life of diflunisal. Diflunisal should be effective against SSA, FAC and FAP, because it binds both WT and variant TTR imposing kinetic stabilization, analogous to mechanism utilized by the inclusion of trans-suppressor subunits into TTR tetramers otherwise composed of disease-associated subunits, which is known to ameliorate human disease. Diflunisal may be less effective against CNS amyloidosis because it cannot cross the blood-brain barrier, although diflunisal analogs (e.g., an analog described herein) may have such an ability.

Example 4

Hydroxylated Polychlorinated Biphenyls Selectively Bind Transthyretin in Blood and Inhibit Amyloidogenesis Polychlorinated biphenyls (PCBs) are known persistent environmental pollutants that are reported to be toxic to rodents and possibly humans. The longevity of these compounds in the environment is due to their slow degradation and high lipophilicity, which allows them to bioaccumulate and concentrate as they move up the food chain. Hydroxylated PCBs (OH-PCBs) are metabolites formed by oxidation of PCBs by the P450 monooxygenases. Definitive data on the toxicity of individual PCB compounds in humans is difficult to find due to the fact that the commercially available PCBs are generally mixtures that contain many different isomers as well as trace amounts of known toxins, e.g. chlorinated dibenzofurans. However, the toxicity of several purified PCBs has been demonstrated in laboratory animals. Bone loss, immunologic toxicity, neurotoxicity and lowered thyroid hormone levels, in addition to the estrogenicity of the OH-PCBs are associated with the administration of these compounds.

Numerous studies demonstrate that PCBs and OH-PCBs bind to transthyretin (TTR) in vitro. It has been suggested that TTR is the protein target in human blood that contributes to the persistence of the OH-PCBs in exposed individuals. While numerous reports suggest TTR as a PCB binding protein in vivo, there is no definitive evidence that PCBs bind to transthyretin in plasma. We have developed an immunoprecipitation method that can be used to place a lower limit on the binding stoichiometry of small molecules to TTR in biological fluids. The TTR binding stoichiometry of PCBs and OH-PCBs to human plasma TTR was evaluated herein.

Post-secretion amyloidogenesis of plasma TTR requiring rate limiting tetramer dissociation, monomer misfolding and misassembly putatively causes senile systemic amyloidosis, familial amyloid cardiomyopathy and the familial amyloid polyneuropathies. Herein, several OH-PCBs are demonstrated to bind selectively to TTR in human plasma and inhibit amyloid fibril formation through tetramer stabilization leading to partial or complete kinetic stabilization of the native state. Four representative TTR.(OH-PCB)$_2$ complexes were characterized by x-ray crystallography to better understand the molecular basis for binding and to provide the basis for the design of optimized TTR amyloidogenesis inhibitors.

Binding Selectivity of PCBs and OH-PCBs for Transthyretin in Human Blood Plasma

Figure 5:
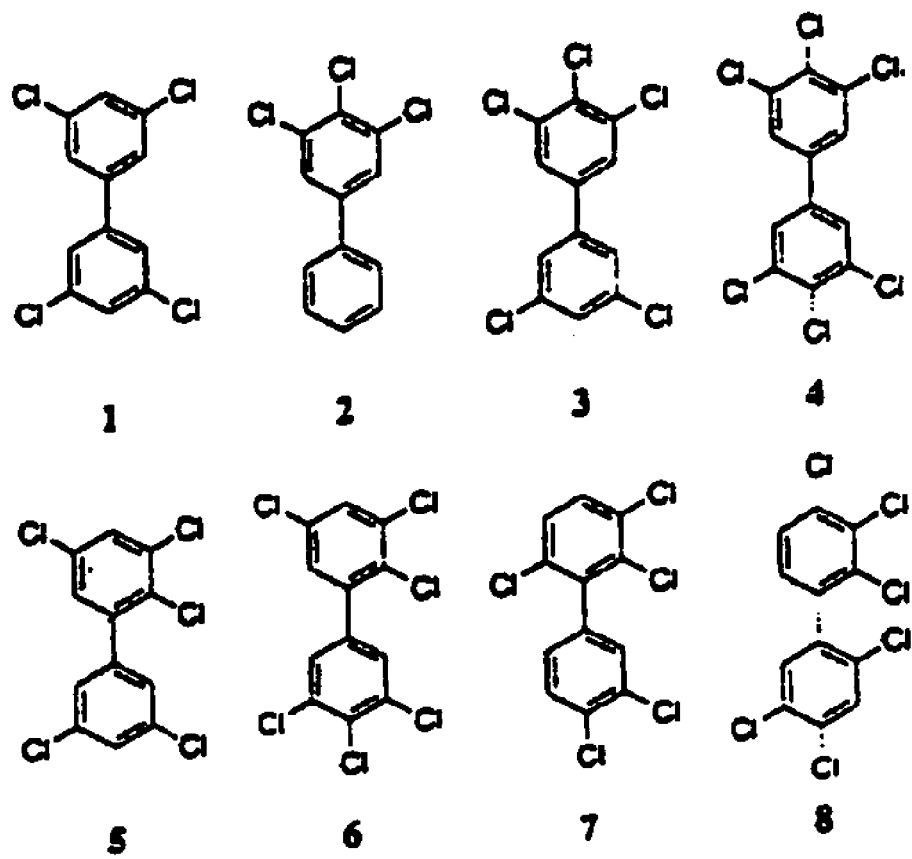
FIG. 5 depicts the structures of polychlorinated biphenyls screened for binding to transthyretin in blood plasma.
Figure 6:
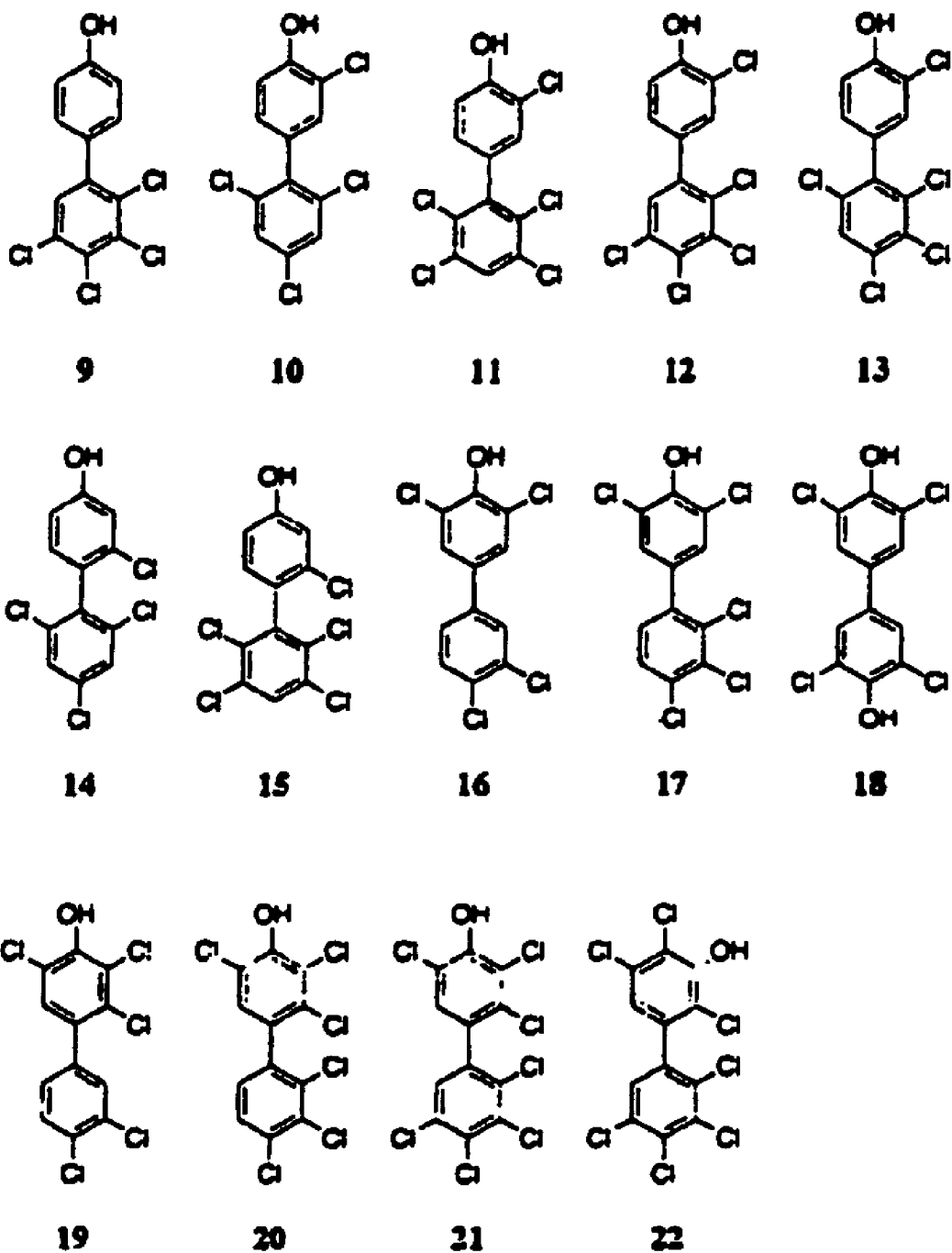
FIG. 6 depicts the structures of hydroxylated polychlorinated biphenyls whose binding to transthyretin in plasma was evaluated along with their amyloid fibril inhibition properties in vitro.

The binding selectivity of eight PCBs (compounds 1-8, FIG. 5), reported to displace thyroid hormone from TTR with an IC50 of less than 50 nM and fourteen OH-PCBs (compounds 9-22, FIG. 6), known PCB metabolites that are reported to bind to TTR or lower thyroxine levels in mice or rats were evaluated. Lower limits on PCB binding stoichiometry to TTR in plasma were established using polyclonal TTR antibodies covalently attached to a sepharose resin that was mixed with human blood plasma pretreated with PCB or OH-PCB (10.8 µM). After washing, the PCB or OH-PCB binding stoichiometry to TTR (≈5 µM) was evaluated by reverse phase HPLC.

Up to two PCBs can bind to the two identical thyroid hormone binding sites in a TTR tetramer. Except for PCBs 1 & 3, the remaining non-hydroxylated PCBs displayed relatively low binding selectivity for plasma TTR (Table 4). In contrast, the OH-PCBs showed good to excellent binding selectivity for plasma TTR (Table 5). Several of the hydroxylated PCBs (e.g., 16 and 22) approach a binding stoichiometry of 2. The binding selectivity of OH-PCBs in whole blood is very similar to that observed in plasma, hence erythrocyte membranes do not significantly sequester the OH-PCBs studied.

TABLE 4

Binding Stoichiometry of PCBs to TTR in Human Blood Plasma

| Compound | Equivalents Bound |
| --- | --- |
| 3 | 1.50 ± 0.42 |
| 1 | 0.62 ± 0.12 |
| 6 | 0.19 ± 0.11 |
| 2 | 0.18 ± 0.03 |
| 5 | 0.06 ± 0.04 |
| 4 | 0.05 ± 0.04 |
| 7 | No Binding |
| 8 | No Binding |

TABLE 5

Binding Stoichiometry of Hydroxylated PCBs to TTR in Human Blood Plasma

| Compound | Equivalents Bound (Plasma) | Equivalents Bound (Blood) |
| --- | --- | --- |
| 16 | 1.86 ± 0.14 | ND |
| 22 | 1.67 ± 0.40 | 1.69 |
| 17 | 1.63 ± 0.05 | ND |
| 19 | 1.48 ± 0.16 | 1.55 |
| 21 | 1.40 ± 0.22 | 1.33 |
| 18 | 1.36 ± 0.21 | ND |
| 12 | 1.23 ± 0.24 | 1.47 |
| 11 | 1.12 ± 0.22 | 1.20 |
| 20 | 1.02 ± 0.09 | 0.86 |
| 10 | 0.96 ± 0.09 | 0.93 |
| 13 | 0.84 ± 0.24 | 0.86 |
| 9 | 0.83 ± 0.19 | 0.57 |
| 14 | 0.81 ± 0.29 | 0.73 |
| 15 | 0.70 ± 0.17 | 0.56 |

The antibody capture of the TTR•PCB complex has the potential to underestimate the PCB binding stoichiometry owing to PCB dissociation from TTR during the 5 wash steps. PCBs and OH-PCBs (10.8 µM) were incubated with recombinant TTR (3.6 µM) to evaluate the stoichiometry of small molecule bound to immobilized TTR after each wash step. Stoichiometry decreased by 10-17% for PCB 2 and OH-PCB 18 after 5 washes, whereas that of PCB 4 decreased by 45%. Quantification of wash-associated losses allows one to estimate the true binding stoichiometry of PCBs and OH-PCBs in plasma. Furthermore, a good correlation between the final stoichiometry of OH-PCB bound to recombinant TTR and the amount bound to TTR in plasma indicates that the compound is a highly selective TTR binder in plasma, e.g., OH-PCB 18. In contrast, PCBs 2 and 4 exhibit a higher binding stoichiometry to TTR in buffer than in plasma, strongly suggesting that they bind to competitor protein(s) as well as TTR in plasma.

TTR Amyloid Fibril Inhibition by Hydroxylated PCBs

The ability of OH-PCBs and PCB 3 to inhibit TTR fibril formation in vitro was evaluated because these compounds exhibit good binding selectivity to TTR in blood. TTR secreted into blood from the liver appears to be the source of systemic TTR amyloid. While it is not yet clear where or how amyloid is formed in humans, the typical denaturant in cells is acid, which is effective in converting nearly all amyloidogenic peptides and proteins into amyloid and/or related aggregates. Hence, acid-mediated (pH 4.4) fibril formation monitored by turbidity was employed to monitor the effectiveness of the PCBs as inhibitors. Hydroxylated PCBs and PCB 3 were highly efficacious as TTR fibril inhibitors. At an inhibitor concentration equal to the WT TTR concentration (3.6 µM), only 12-50% of the normal amount of fibril formation was observed after a 72 h incubation period. This activity is equivalent to that displayed by the best fibril inhibitors discovered to date, such as flufenamic acid (Flu), which was included as a positive control.

Binding of OH-PCB 18 to TTR

Previous mass spectrometry experiments suggest that OH-PCB 18 exhibits positive binding cooperativity to TTR's two $C_2$ related thyroid hormone binding sites. When substoichiometric (<1:1) amounts of 18 are added to TTR, the predominant species observed in the mass spectrometer are apo-TTR and the TTR•$18_2$ complex, consistent with positively cooperative binding. The TTR binding characteristics of 18 are in contrast to those exhibited by numerous other TTR amyloid fibril inhibitors that bind with negative cooperativity. Isothermal titration calorimetry studies carried out under physiological conditions reveal that the binding of OH-PCB 18 to WT TTR fits best to a model where the dissociation constants are identical $K_d$s (3.2±1.8 nM). This result does not disprove positively cooperative binding, as one cannot achieve a low enough concentration of TTR to probe positive cooperativity because of the insufficient heat released. Attempts to fit the collected data to models of positively or negatively cooperative binding yielded poor fits.

Co-Crystal Structures of OH-PCBs 12, 16, 17 and 18

Crystals of OH-PCBs 12, 16, 17 and 18 bound to WT TTR were obtained by soaking TTR crystals with a 10-fold excess of inhibitor for four weeks. X-ray structures were then solved for each of the complexes. The TTR dimer within the crystallographic asymmetric unit forms half of the two ligand-binding pockets. Because both binding sites are bisected by the same two-fold axis of symmetry, two symmetry equivalent binding modes of the inhibitors are typically observed. Each TTR binding site can be subdivided into inner and outer cavities. These cavities comprise three so-called halogen binding pockets (HBPs) because they are occupied by the iodines on the two aromatic rings of thyroxine. HBP 3 and 3' are located deep within the inner binding cavity, HBP 2 and 2' define the boundary between the inner and outer binding cavity, whereas HBP 1 and 1' are located near the periphery of outer binding cavity. The co-crystal structures reveal that the C—C bond connecting the two aromatic rings of the OH-PCB are nearly centered on the 2-fold symmetry axis, giving the appearance of a single binding conformation. The dihedral angle between two phenyl rings is 59° for 12, 37° for both 16 and 17, and 44° for 18. All of the OH-PCBs occupy similar positions in the inner and outer binding pockets. The van der waals complimentarity of the biaryl ring system facilitates several inter-subunit interactions involving residues X, Y and Z in one subunit and residues n', m', and o' in the other subunit composing each binding site. Several of the substituents on the phenyl rings are off-axis and can be modeled in multiple positions within the observed electron density.

OH-PCB 18 Bound to TTR

The 1.8 Å X-ray structure of the TTR•$18_2$ complex demonstrates that the inhibitor has excellent steric complementarity with the TTR binding site. Molecular mechanics (Insight II, Accelrys) indicates that the unbound conformation of 18 is close to its bound structure. The refined structure defines direct and water-mediated electrostatic interactions that contribute to high affinity binding of 18. One of the 3-Cl, 4-OH, 5-Cl identically substituted aromatic rings occupies the inner binding pocket, its chlorine substituents projecting into HBP 3 and 3'. The side chains of Ser117 and Thr119 adopt an alternative conformation by rotation about their Cα-Cβ bonds as discerned by the unbiased electron density maps. The side chain of Ser117 adopts all three rotomer conformations as discerned by the distribution of electron density. Interestingly, two water molecules are located in between the adjacent Ser117 residues at the two-fold axis with 50% occupancy, facilitating a network of hydrogen bonds connecting the Ser117 residues, the nearby water molecules and the phenol functionality of 18. It is not clear from an inspection of the structure why 18 binds with non-or positively cooperative behavior. The other identically substituted ring occupies the outer TTR binding pocket with its halogens projecting into HBPs 1 and 1'.

Compound 16 Bound to TTR

The 3-Cl, 4-OH, 5-Cl tri-substituted phenolic ring of 16 is oriented into the inner binding site of TTR making the same electrostatic and hydrophobic interactions with TTR that this ring does in the TTR-$18_2$ structure described above. The 3,4-dichlorinated aromatic ring occupies the outer binding pocket, with the halogen directed into HBP-1 or 1' depending upon which symmetry equivalent binding mode is being considered. The electron density of 16, like that of OH-PCB 18, is symmetric and thus it is not possible to position the para OH and para Cl unambiguously based upon the electron density map. The unbiased electron density map is consistent with three rotomer conformations of Ser117 and contains two water molecules in between the Ser117 residues, analogous to the TTR•$18_2$ structure.

OH-PCB 17 Bound to TTR

Inhibitor 17 binds with its 3-Cl, 4-OH, 5-Cl substituted aryl ring oriented into the inner binding pocket utilizing the same interactions that this ring uses in the TTR•$16_2$ and TTR•$18_2$ structures described above. The 2,3,4-tri-chlorinated ring occupies the outer binding pocket utilizing interactions with HBP-1, HBP-1', HBP-2, HBP-2' in the two symmetry equivalent binding modes. The multiple conformations of Ser117 and the two conserved water molecules are also features of the TTR•$17_2$ structure. A conformational change of the Thr119 side chain was evident from the unbiased electron density maps.

Compound 12 Bound to TTR

Biaryl 12 places its 3-Cl, 4-OH substituted aryl ring in the outer binding pocket, with its two chlorines interacting with HBP-1 and 1'. In contrast to the structures of TTR•$16_2$ and TTR•$17_2$ where the phenol is located in the inner binding pocket. The hydroxyl group (probably in the ionized form) is within hydrogen bonding distance of the Lys15 side chains. The tetra-chlorinated ring is placed in the inner binding pocket wherein the halogens are oriented in HBPs 2 and 2' as well as 3 and 3'. The Ser117 and Thr119 side chains adopt conformations that are identical to those found in the apo-TTR structure, unlike the situation in 16, 17 and 18.

Herein, of 8 PCBs previously reported to displace T4 with an $IC_{50}$ of less than 50 nM, only 1 and 3 were shown to bind to TTR with an appreciable stoichiometry in human plasma. In contrast, all fourteen OH-PCBs previously reported to bind to TTR exhibited significant binding selectivity to TTR in plasma. This is consistent with the observation that OH-PCBs are observed primarily in plasma and appear to be selectively retained there, as opposed to retention in lipids and other tissues where PCBs typically accumulate. The OH-PCBs also bind selectively to TTR in whole blood consistent with the idea that they do not partition into lipid membranes.

The amount of PCB (or OH-PCB) that washes off of the antibody•TTR•PCB complex during the washing steps was evaluated using recombinant WT TTR. The extent of wash-associated PCB dissociation is molecule specific. Some compounds exhibit high binding stoichiometry after the washes, consistent with significant initial binding and low wash-associated losses, implying a slow dissociation rate. Compounds exhibiting low binding stoichiometry fall into at least two categories: high initial binding stoichiometry with significant wash-associated losses or low initial binding stoichiometry without significant wash-associated losses, the latter scenario applicable to compounds that bind with high affinity to TTR, but with even higher affinity to another plasma protein(s). PCBs 2 and 4 both exhibit low post-wash binding stoichiometry to recombinant TTR. Forty five % of PCB 4 was lost due to washes whereas PCB 2 simply exhibits poor initial binding stoichiometry with minimal wash-associated losses (10%). The post-wash selectivity values reflect a lower limit of the amount of PCB that is initially bound in plasma. Compounds like PCB 18, which are characterized by high post-wash binding stoichiometry must have high binding affinity and selectivity, consistent with the slow off rate observed.

In addition to their high binding selectivity to plasma TTR, the OH-PCBs and PCB 3 also display excellent inhibition of TTR fibril formation in vitro. The efficacy of inhibitors 14, 15, and 18 are among the highest observed to date at equimolar inhibitor and TTR concentration (3.6 μM). This is likely attributable to their high binding affinity (also consistent with their low off rate) and their non- or positively cooperative TTR binding properties which are unusual. The nM $K_d$s exhibited by the best inhibitor, OH-PCB 18, dictates that the native state of TTR will be stabilized by >3 kcal/mol. Ground state stabilization raises the tetramer dissociation barrier (rate limiting step in TTR amyloidogenesis) substantially, such that the tetramer cannot dissociate on a biologically relevant timescale. Kinetic stabilization of the native non-amyloidogenic state mediated by binding of 18 to the ground state was confirmed by dramatically slowed tetramer dissociation in 6 M urea and sluggish amyloidogenicity at pH 4.4. OH-PCB 18 (3.6 μM) is believed to be an impressive amyloid inhibitor because it is an excellent kinetic stabilizer of tetrameric TTR, i.e. it prevents ⅔ of a 3.6 μM TTR sample from being amyloidogenic at pH 4.4 because TTR•18 and TTR•$18_2$ are incompetent to form amyloid, the remainder of TTR (1.18 μM) forms amyloid very inefficiently because of its low concentration. The dissociation rates of the best OH-PCB inhibitors may also be slower than expected because of TTR structural annealing around the OH-PCB, but this has not yet been evaluated as carefully as required. At a minimum, these compounds provide guidance for the synthesis of exceptional inhibitors, or may themselves prove useful as inhibitors depending on their toxicity profile.

The structural information on TTR bound to OH-PCBs 12, 16, 17 and 18 reveal that these biaryls generally bind along the crystallographic two-fold symmetry axis. The dihedral angle between the two rings ranges from ~40-60°, allowing the halogen binding pockets (HBPs) on two neighboring subunits to be engaged simultaneously, leading to stabilization of the tetrameric quaternary structural interface. Hydroxylated PCB 18 has optimal structural complimentarily with TTR as its chlorines are able to bind to HBPs 1 and 1' as well as 3 and 3' simultaneously. This is not the case with 16 and 17, which require consideration of both symmetry equivalent binding modes in order to extend chlorines into HBPS 1, 1', 3 and 3'.

The orientation of the phenolic ring into the inner binding pocket appears to play a important role in that it enables a water mediated hydrogen bonding network to form between it and neighboring TTR subunits that presumably further stabilizes the native quaternary structure of TTR. A H-bonding network involving the three staggered conformations of Ser-117, the phenolic group of the inhibitor and the two conserved water molecules creates an electrostatic network that interconnects the two subunits that form the PCB binding site. In all three structures, Thr119 also occupies multiple rotamer conformations. In contrast, this network of electrostatic interactions is absent in the $12_2$•TTR complex in which the hydroxyl substituted phenyl ring is oriented in the outer binding pocket and wherein Ser 117 and Thr 119 adopt apo side chain conformations.

The toxicity of OH-PCBs is not well established in the literature. In a variety of in vitro and animal studies, OH-PCBs appear to be either mildly estrogenic or anti-estrogenic. Other toxicity mechanisms have been suggested and there are also reports of decreased thyroid hormone levels in animals exposed to these compounds. The suggestion that OH-PCB binding to TTR lowers T4 levels and that lowered T4 levels reflects small molecule TTR binding is difficult to directly support. Since roughly half of T4 is carried by albumin, the displacement of T4 from the albumin binding sites seems more likely to be the cause the lowered T4 levels in individuals exposed to PCBs. Thyroid binding globulin has the highest affinity for thyroxine and is a main carrier in humans, but it is not present in many lower mammals, including rats and mice where many of the toxicological profiles of these compounds have been studied. Thus, in these species it is more likely that compounds binding to TTR will have an effect on the overall binding and transport of T4. Data showing binding of PCBs to TBG suggest little interaction, with the exception of one or two weakly binding compounds. Therefore, the effect of OH-PCBs on human thyroid levels should be minimal unless they bind to albumin. There are also reports that these compounds may be interfering with thyroid hormone activation or increasing the rate of sulfation, and therefore inactivation, of T4. OH-PCBs could also bind to other thyroid hormone targets including thyroid hormone receptors, which seems reasonable given the structural analogy with T4.

It is clear that little is established regarding hydroxylated PCB toxicity, especially in humans. The toxicology in rodents is expected to be more severe owing to TTR's role as the primary thyroid hormone transporter. What is clear is that hydroxylated PCBs exhibit excellent activity as inhibitors of transthyretin fibril formation, suggesting that this class of compounds has the potential to be useful for the inhibition of amyloid fibril formation.

Materials and Methods

Transthyretin Antibody Purification and Conjugation to Sepharose

Antibodies were produced, purified and coupled to Sepharose. The resin was stored as a 1:1 slurry in TSA (10 mM Tris, pH 8.0/140 mM NaCl/0.025% $NaN_3$). In addition, quenched Sepharose was prepared by coupling 200 mM Tris, pH 8.0 to the resin instead of the antibody.

Human Plasma Preparation

Whole blood was drawn from healthy volunteers at the Scripps General Clinical Research Center's Normal Blood-Drawing Program and transferred to 50 mL conical tubes. The tubes were centrifuged at 3000 RPM (1730×g) in a Sorvall RT7 benchtop centrifuge equipped with a swinging bucket rotor for 10 min at 25° C. The plasma supernatant was removed and centrifuged again at 3000 RPM for 10 min to remove the remaining cells. Sodium azide was added to give a 0.05% solution. The plasma was stored at 4° C. until use Immunoprecipitation of Transthyretin and Bound PCBs A 2 mL eppendorf tube was filled with 1.5 mL of human blood plasma and 7.5 μL of a 2.16 mM DMSO solution of the PCB under evaluation. This solution was incubated at 37° C. for 24 h. A 1:1 resin/TSA slurry (187 μL) of quenched Sepharose was added to the solution and gently rocked at 4° C. for 1 h. The solution was centrifuged (16,000×g) and the supernatant divided into 3 aliquots of 400 μL each. These were each added to 200 μL of a 1:1 resin/TSA slurry of the anti-transthyretin antibody-conjugated Sepharose and slowly rocked at 4° C. for 20 min. The samples were centrifuged (16,000×g) and the supernatant removed. The resin was washed with 1 mL TSA/0.05% Saponin (Acros) (3×10 min) at 4° C., and additionally with 1 mL TSA (2×10 min) at 4° C. The samples were centrifuged (16,000×g), the final wash removed, and 155 μL of 100 mM triethylamine, pH 11.5 was added to elute the TTR and bound small molecules from the antibodies. Following gentle rocking at 4° C. for 30 min, the samples were centrifuged (16,000×g) and 145 μL of the supernatant, containing TTR and inhibitor, was removed.

HPLC Analysis and Quantification of Transthyretin and Bound PCBs

The supernatant elution samples from the TTR antibody beads (145 μL) were loaded onto a Waters 71P autosampler. A 135 μL injection of each sample was separated on a Keystone 3 cm C18 reverse phase column utilizing a 40-100% B gradient over 8 min (A: 94.8% $H_2O$/5% acetonitrile/0.2% TFA; B: 94.8% acetonitrile/5% $H_2O$/0.2% TFA), controlled by a Waters 600E multisolvent delivery system. Detection was accomplished at 280 nm with a Waters 486 tunable absorbance detector, and the peaks were integrated to give the area of both TTR and the small molecule. In order to determine the quantity of each species, known amounts of tetrameric TTR or PCB were injected onto the HPLC. The peaks were integrated to create calibration curves from linear regressions of the data using Kaleidagraph (Synergy Software). The calibration curves were used to determine the number of moles of each species present in the plasma samples. The ratio of small molecule to protein was calculated to yield the stoichiometry of small molecule bound to TTR in plasma.

Transthyretin Amyloid Fibril Formation Assay

The compounds were dissolved in DMSO at a concentration of 720 μM. Five μL of a solution of the compound being evaluated was added to 0.5 mL of a 7.2 μM TTR solution in 10 mM phosphate pH 7.6, 100 mM KCl, 1 mM EDTA buffer, allowing the compound to incubate with TTR for 30 min. 495 μL of 0.2 mM acetate pH 4.2, 100 mM KCl, 1 mM EDTA was added, to yield final protein and inhibitor concentrations of 3.6 μM each and a pH of 4.4. The mixture was then incubated at 37° C. for 72 h, after which the tubes were vortexed for 3 sec and the optical density was measured at 400 nm. The extent of fibril formation was determined by normalizing each optical density by that of TTR without inhibitor, defined to be 100% fibril formation. Control solutions of each compound in the absence of TTR were also tested and none absorbed appreciably at 400 nm.

Isothermal Titration Calorimetry of PCB 18 and TTR

A 25 μM solution of compound 18 (in 10 mM phosphate pH 7.6, 100 mM KCl, 1 mM EDTA, 8% DMSO,) was titrated into a 1.2 μM solution of TTR in an identical buffer using a Microcal MCS Isothermal Titration Calorimeter (Microcal, Northampton, Mass.). An initial injection of 2 μL was followed by 25 injections of 10 μL at 25° C. The thermogram was integrated and a blank was subtracted to yield a binding isotherm that fit best to a model of two identical binding sites using the ITC data analysis package in ORIGIN 5.0 (Microcal).

Crystallization and X-Ray Data Collection

Crystals of recombinant TTR were obtained from protein solutions at 5 mg/ml (in 100 mM KCl, 100 mM phosphate, pH 7.4, 1 M ammonium sulfate) equilibrated against 2 M ammonium sulfate in hanging drop experiments. The TTR•ligand complexes were prepared from crystals soaked for 2 weeks with a 10-fold molar excess of the ligand to ensure full saturation of both binding sites. 1:1 acetone:water solution was used as a soaking agent. A DIP2030b imaging plate system (MAC Science, Yokohama, Japan) coupled to a RU200 rotating anode X-ray generator was used for data collection. The crystals were placed in paratone oil as a cryo-protectant and cooled to 120 K for the diffraction experiments. Crystals of all TTR•ligand complexes are isomorphous with the apo crystal form containing unit cell dimensions a=43 Å, b=86 Å and c=65 Å. They belong to the space group $P2_12_12$ and contain half of the homotetramer in the asymmetric unit. Data were reduced with DENZO and SCALEPACK.

Structure Determination and Refinement

The protein atomic coordinates for TTR from the Protein Data Bank (accession number 1BMZ) were used as a starting model for the refinement of native TTR and the TTR-ligand complexes by molecular dynamics and energy minimization using the program CNS. Maps were calculated from diffraction data collected on TTR crystals either soaked with PCBs or cocrystalized simultaneously. For the complexes of TTR with the PCBs, the resulting maps revealed approximate positions of the ligand in both binding pockets of the TTR tetramer, with peak heights of above 5-9 r.m.s. In order to further improve the small molecule electron density and remove the model bias, the model was subjected to several cycles of the warp/shake protocol, which resulted in noticeable improvement in the map, especially around the inhibitor. Subsequent model fitting was done using these maps and the ligand molecule was placed into the density. In all three cases the minimum-energy conformation of the inhibitor calculated by the program InsightII (Accelrys) was in good agreement with the map. Because of the two-fold crystallographic symmetry axis along the binding channel, a statistical disorder model must be applied, giving rise to two ligand binding modes in each of the two binding sites of tetrameric TTR. Water molecules were added based upon the unbiased electron density map. Because of the lack of interpretable electron densities in the final map, the nine N-terminal and three C-terminal residues were not included in the final model.

Example 5

Benzoxazoles as Transthyretin Amyloid Fibril Inhibitors

Transthyretin's two thyroxine binding sites are created by its quaternary structural interface. The tetramer can be stabilized by small molecule binding to these sites, potentially providing a means to treat TTR amyloid disease with small molecule drugs. Many families of compounds have been discovered whose binding stabilizes the tetrameric ground state to a degree proportional to the small molecule dissociation constants $K_{d1}$ and $K_{d2}$. This also effectively increases the dissociative activation barrier and inhibits amyloidosis by kinetic stabilization. Such inhibitors are typically composed of two aromatic rings, with one ring bearing halogen substituents and the other bearing hydrophilic substituents. Benzoxazoles substituted with a carboxylic acid at C(4)-C(7) and a halogenated phenyl ring at C(2) also appeared to complement the TTR thyroxine binding site. A small library of these compounds was therefore prepared by dehydrocyclization of N-acyl amino-hydroxybenzoic acids as illustrated in Scheme 1.

Scheme 1: General Synthesis of Benzoxazoles

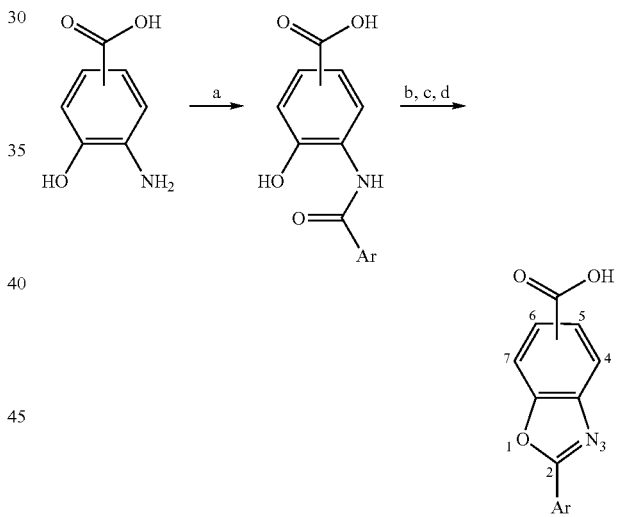

Reagents: (a) ArCOCl, THF, pyridine (Ar=Phenyl, 3,5-Difluorophenyl, 2,6-Difluorophenyl, 3,5-Dichlorophenyl, 2,6-Dichlorophenyl, 2-(Trifluoromethyl)phenyl, and 3-(Trifluoromethyl)phenyl); (b) TsOH.H$_2$O, refluxing xylenes; (c) TMSCHN$_2$, benzene, MeOH; (d) LiOH, THF, MeOH, H$_2$O (8-27% yield over 4 steps).

Figure 7:
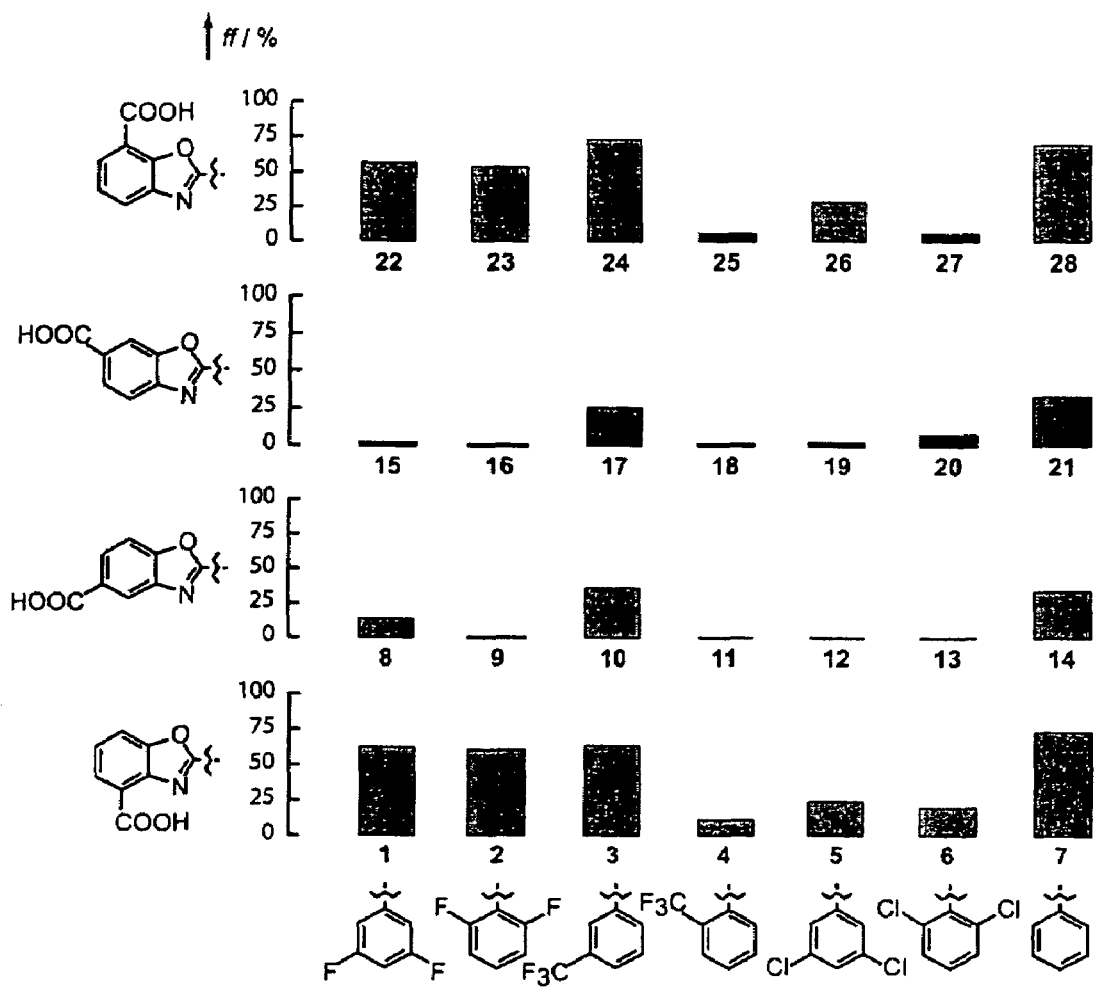
FIG. 7 is a graph depicting suppression of transthyretin fibril formation by benzoxazole compounds. The position of the carboxyl on the benzoxazole is shown along the left-hand side, while the C(2) phenyl ring is shown along the bottom. The bars indicate the percent fibril formation (ff), that is, the amount of fibrils formed from transthyretin (3.6 µM) in the presence of the benzoxazole compound (7.2 µM) relative to the amount formed by transthyretin in the absence of inhibitor (which is defined as 100%).

The benzoxazoles were evaluated using a series of analyses of increasing stringency. WT TTR (3.6 μM) was incubated for 30 min (pH 7, 37° C.) with a test compound (7.2 μM). Since at least one molecule of the test compound must bind to each molecule of TTR tetramer to be able to stabilize it, a test compound concentration of 7.2 μM is only twice the minimum effective concentration. The pH was then adjusted to 4.4, the optimal pH for fibrilization. The amount of amyloid formed after 72 h (37° C.) in the presence of the test compound was determined by turbidity at 400 nm and is expressed as % fibril formation (ff), 100% being the amount formed by TTR alone. Of the 28 compounds tested, 11 reduced fibril formation to negligible levels (ff<10%; FIG. 7).

Figure 8:
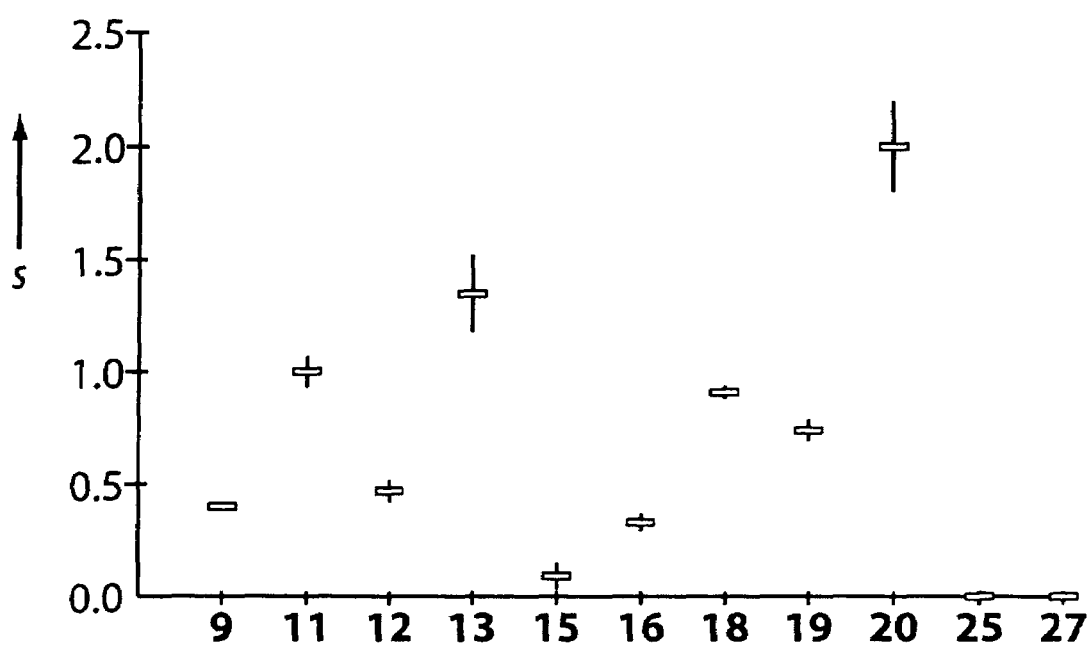
FIG. 8 is a graph depicting stoichiometry (s) of benzoxazoles bound to transthyretin after incubation in human blood plasma. Immunoprecipitation with a resin-bound antibody was used to capture transthyretin. Following release of transthyretin from the resin, the amounts of transthyretin and inhibitor were quantified from the areas under their peaks in an HPLC chromatogram. The maximum possible value of s is 2. Compound numbers are shown along the bottom axis. The thin vertical lines indicate the measurement error.

The 11 most active compounds were then evaluated for their ability to bind selectively to TTR over all other proteins in blood. Human blood plasma (TTR conc. 3.6-5.4 µM) was incubated for 24 h with the test compound (10.8 µM) at 37° C. The TTR and any bound inhibitor were immunoprecipitated using a sepharose-bound polyclonal TTR antibody. The TTR with or without inhibitor bound was liberated from the resin at high pH, and the inhibitor:TTR stoichiometry was ascertained by HPLC analysis (FIG. 8). Benzoxazoles with carboxylic acids in the 5- or 6-position, and 2,6-dichlorophenyl (13, 20) or 2-trifluoromethylphenyl (11, 18) substituents at the 2-position displayed the highest binding stoichiometries. In particular, 20 exhibited excellent inhibitory activity and binding selectivity. Hence, its mechanism of action was characterized further.

To confirm that 20 inhibits TTR fibril formation by binding strongly to the tetramer, isothermal titration calorimetry (ITC) and sedimentation velocity experiments were conducted with wt TTR. ITC showed that two equivalents of 20 bind with average dissociation constants of $K_{d1}=K_{d2}=55$ (±10) nM under physiological conditions. These are comparable to the dissociation constants of many other highly efficacious TTR amyloidogenesis inhibitors. For the sedimentation velocity experiments, TTR (3.6 µM) was incubated with 20 (3.6 µM, 7.2 µM, 36 µM) under optimal fibrilization conditions (72 h, pH 4.4, 37° C.). The tetramer (55 kDa) was the only detectable species in solution with 20 at 7.2 or 36 µM. Some large aggregates formed with 20 at 3.6 µM, but the TTR remaining in solution was tetrameric.

Figure 9:
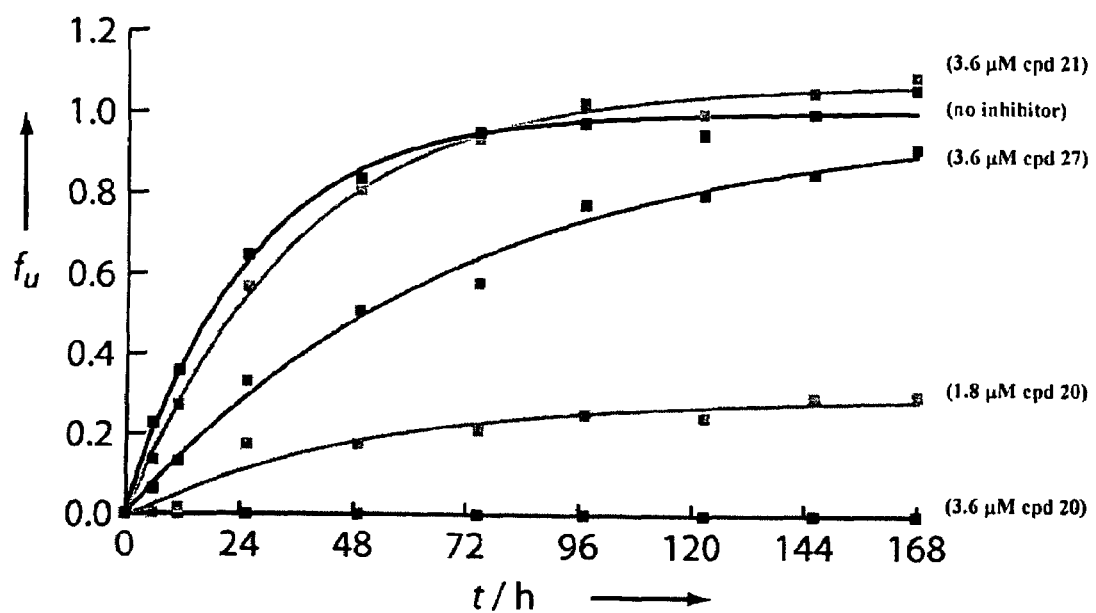
FIG. 9 is a graph depicting dissociation as a function of time (t) for wt transthyretin (1.8 µM) in 6 M urea without inhibitor, or in the presence of 3.6 µM of compounds 20, 21, or 27, or 1.8 µM compound 20.

T119M subunit inclusion and small molecule binding both prevent TTR amyloid formation by raising the activation barrier for tetramer dissociation. An inhibitor's ability to do this is most rigorously tested by measuring its efficacy at slowing tetramer dissociation in 6 M urea, a severe denaturation stress. Thus, the rates of TTR tetramer dissociation in 6 M urea in the presence and absence of 20, 21 or 27 were compared (FIG. 9). TTR (1.8 µM) was completely denatured after 168 h in 6 M urea. In contrast, 20 at 3.6 µM prevented tetramer dissociation for at least 168 h (>3× the half-life of TTR in human plasma). With an equimolar amount of 20, only 27% of TTR denatured in 168 h. Compound 27 (3.6 µM) was much less able to prevent tetramer dissociation (90% unfolding after 168 h), even though it was active in the fibril formation assay. Compound 21 did not hinder the dissociation of TTR at all. These results show that inhibitor binding to TTR is necessary but not sufficient to kinetically stabilize the TTR tetramer under strongly denaturing conditions; it is also important that the dissociation constants be very low (or that the off rates be very slow). Also, the display of functional groups on 20 is apparently optimal for stabilizing the TTR tetramer; moving the carboxylic acid from C(6) to C(7), as in 27, or removing the chlorines, as in 21, severely diminishes its activity.

Figure 10:
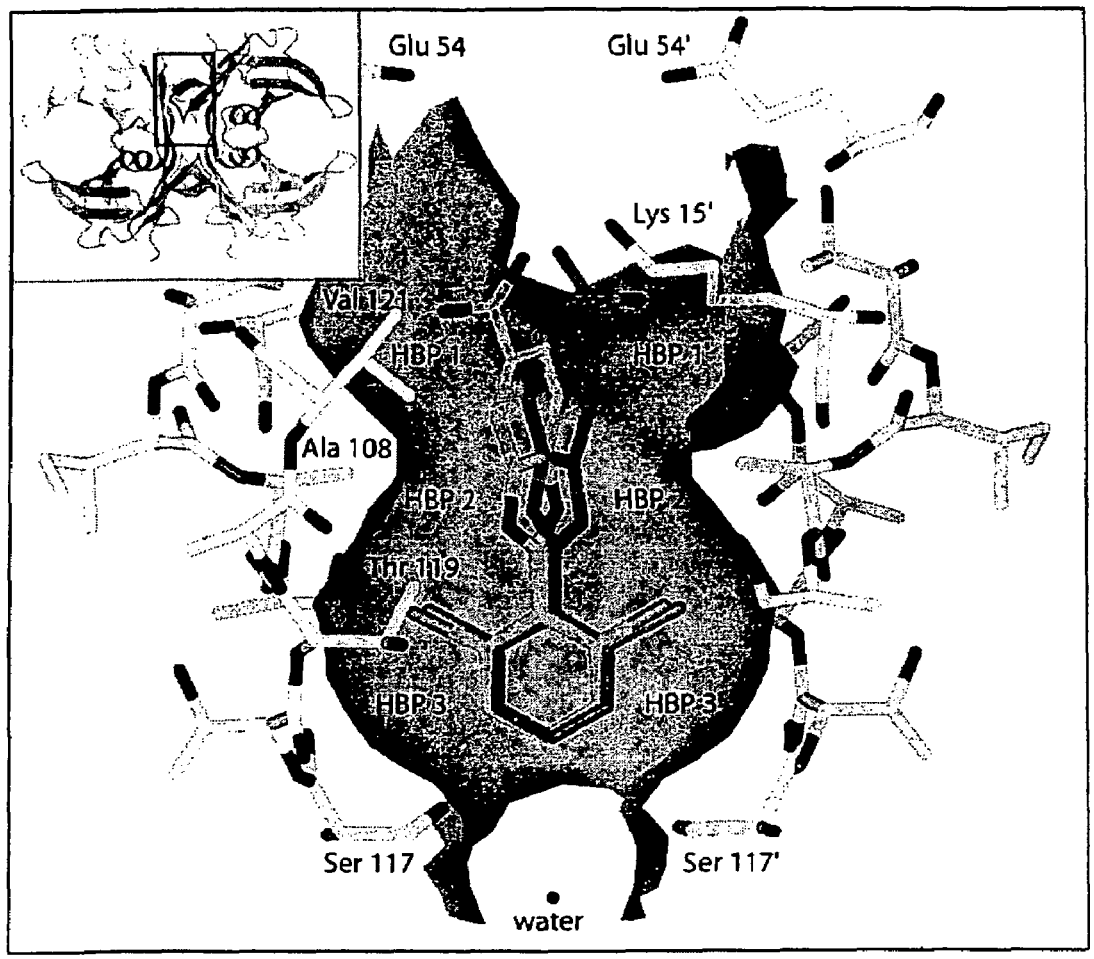
FIG. 10 depicts the X-ray co-crystal structure of compound 20 bound to transthyretin. Equivalent residues in different subunits are distinguished with primed and unprimed residue numbers, as are the pairs of halogen binding pockets.

The role of the substituents in 20 is evident from its co-crystal structure with TTR (FIG. 10). Compound 20 orients its two chlorine atoms near halogen binding pockets 2 and 2' (so-called because they are occupied by iodines when thyroxine binds to TTR). The 2,6 substitution pattern on the phenyl ring forces the benzoxazole and phenyl rings out of planarity, optimally positioning the carboxylic acid on the benzoxazole to hydrogen bond to the ε-$NH_3^+$ groups of Lys 15/15'. Hydrophobic interactions between the aromatic rings of 20 and the side chains of Leu 17, Leu 110, Ser 117, and Val 121 contribute additional binding energy.

Methods

The general procedure for benzoxazole synthesis and characterization of the products ($^1$H- and $^{13}$C-NMR and high resolution mass spectra) are detailed below.

Analytical Ultracentrifugation

The quaternary structure of TTR in the presence of 20 was observed using sedimentation velocity analytical ultracentrifugation. The samples were incubated with 20 at 3.6, 7.2 or 36 µM for 72 h. The data were collected on a temperature-controlled Beckman XL-I analytical ultracentrifuge (equipped with an An60Ti rotor and photoelectric scanner). A double sector cell, equipped with a 12 mm Epon centerpiece and sapphire windows, was loaded with 400-420 µL of sample using a syringe. Data were collected at rotor speeds of 3000 and 50000 rpm in continuous mode at 25° C., with a step size of 0.005 cm employing an average of 1 scan per point. Detection was carried out at 280 nm. The data were subjected to time-derivative analysis using the program DCDT+ developed by Philo (Philo, 2000; Stafford, 1992). The analysis showed that the distribution of species in solution represented by a range of s values. This distribution was then fitted to various models in order to determine the sedimentation and diffusion coefficients for species in the system. The molecular weight of each species was determined by methods reported previously (Petrassi, et al 2000). The s values found for TTR showed that it remained tetrameric in the presence of 7.2 and 36 µM of 20, while at 3.6 µM the TTR remaining in solution was tetrameric despite the formation of some aggregate.

Crystallization and X-Ray Data Collection

Crystals of wt TTR were obtained from protein solutions at 12 mg/mL (in 100 mM KCl, 1 mM EDTA, 10 mM Sodium phosphate, and pH 7.0, 0.35 M ammonium sulfate) equilibrated against 2 M ammonium sulfate in hanging drop experiments. The TTR-20 complex was prepared from crystals soaked for 3 wk with a 10 fold molar excess of the ligand to ensure full saturation of both binding sites. The ligand-soaked crystal diffracted up to 1.55 Å on a Quantum-4 detector at the monochromatic high energy source of 14-BM-C, BIOCARS, Advanced Photon Source (Argonne National Laboratory). The crystals were soaked in paratone oil and flash-cooled to 100 K for the diffraction experiments. Crystals of the TTR-20 complex are isomorphous with the apo crystal form with unit cell dimensions a=43.1 Å, b=84.7 Å, and c=64.7 Å, space group $P2_12_12$ with two TTR subunits in the asymmetric unit. Data were reduced with DENZO and SCALEPACK of the HKL2000 suite. (Otwinowski, 1997)

Structure Determination and Refinement

The protein atomic coordinates for TTR from the Protein Data Bank (accession number 1BMZ) were used as a starting model for the molecular replacement searches. The refinement of the TTR-20 complex structure was carried out using molecular dynamics and the energy minimization protocols of CNS. The resulting difference Fourier maps revealed binding of the ligand in both binding pockets of the TTR tetramer. Using these maps, the ligand could be unambiguously placed into the density and was included in the crystallographic refinement. The minimum energy conformation of the inhibitor calculated by the program Insight II (Accelrys Inc.) was used as the initial model for the crystallographic refinement. Because the 2-fold crystallographic symmetry axis is along the binding channel, a statistical disorder model had to be applied, giving rise to two ligand binding modes per TTR binding pocket. After several cycles of simulated annealing and subsequent positional and temperature factor refinement, water molecules were placed into the difference Fourier maps. The final cycle of map fitting was done using the unbiased weighted electron density map calculated by the shake n' warp bias removal protocol. The symmetry related binding conformations of the ligand were in good agreement with the unbiased annealed omit maps as well as the shake n' warp unbiased weighted maps phased in the absence of the inhibitor. Because of the lack of interpretable electron densities in the final map, the nine N-terminal and three C-terminal residues were not included in the final model. A summary of the crystallographic analysis is presented in Table 6.

TABLE 6

Statistics for X-ray Crystal Structure

| | |
|---|---|
| Completeness (%) (overall/outer shell) | 86/90 |
| $R_{sym}$ (Overall/outer shell) | 0.05/0.33 |
| Refinement statistics | |
| Resolution (Å) | 33.02-1.55 |
| R-factor/R-free (%) | 21.1/24.3 |
| Rmsd bond length (Å) | 0.03 |
| Rmsd bond angles (°) | 2.5 |
| Other statistics | |
| Crystal dimensions (mm) | 0.3 × 0.2 × 0.15 |
| Crystal system | Orthorhombic |
| Unit cell dimensions (a, b, c in Å) | 43.1, 84.7, 64.7 |
| Unit cell volume (Å$^3$) | 236123 |
| Maximum resolution (Å) | 1.54 |
| Scan mode | Phi |
| Temperature of measurement | 100 K |
| Number of independent reflections | 30705 |
| Method of structure solution | Molecular replacement by EPMR (Kissinger, 1999) |
| Refinement against | $F_{obs}$ |
| Refinement target | Maximum likelihood |
| Program used for refinement | CNS-Solve (Brunger 1998) |
| Database | Protein Data Bank |

Benzoxazole Synthesis—General Methods

Unless stated otherwise, all reactions were carried out in oven-dried glassware under a dry argon atmosphere using a FirstMate Organic Synthesizer (Argonaut Technologies). All solvents (anhydrous) and reagents were purchased from Aldrich and used without further purification. $^1$H NMR spectra were measured at 500 MHz on a Bruker DRX-500 spectrometer or at 600 MHz on a Bruker DRX-600 spectrometer, and were referenced to internal C$\underline{H}$D$_2$-S(O)—CD$_3$ (2.49 ppm). $^{13}$C spectra were performed at 125 MHz on a Bruker DRX-500 or at 150 MHz on a Bruker DRX-600 instrument and were referenced to ($\underline{C}$D$_3$)$_2$SO (39.5 ppm). Thin-layer chromatographic analyses were performed on Glass-backed thin-layer analytical plates (Kieselgel 60 F$_{254}$, 0.25 mm, EM Science no. 5715-7). Visualization was accomplished using UV absorbance or 10% phosphomolybdic acid in ethanol. Chromatography was performed on a chromatotron (Harrison Research, Model 7924T, 2 mm plate) or on a preparative silica gel plate (Kieselgel 60 F$_{254}$, 1 mm, EM Science no. 13895-7).

General Procedure for Benzoxazole Synthesis

A mixture of amino hydroxybenzoic acid (0.2 mmol) in THF (3 mL) was sequentially treated with pyridine (500 μl, 0.6 mmol) and the desired acid chloride (0.2 mmol). The reaction mixture was stirred at ambient temperature for 10 h, refluxed for 1 h, concentrated in vacuo and used in the next step without purification.

p-Toluenesulfonic acid monohydrate (380.4 mg, 2.0 mmol) was added to the crude reaction mixture in xylenes (5 mL) and the resulting mixture was stirred at reflux overnight. After 12 h, the reaction was cooled to ambient temperature, quenched with NaOH (2 mL, 1 N) and the phases were separated. The aqueous layer was acidified with HCl (1 N) to pH 2 and extracted with EtOAc (4×3 mL). The combined organic layers were dried over MgSO$_4$, filtered and concentrated in vacuo. The resulting residue was dissolved in a mixture of MeOH:Benzene (2 mL; 1:4), treated with TMS-CHN$_2$ (200 μL of 2.0 M solution in hexanes, 0.4 mmol) at 25° C. and the reaction progress was monitored by TLC (usually complete after 0.5 h). The reaction mixture was concentrated in vacuo, and the residue was chromatographed (10 to 25% EtOAc/hexanes gradient) to afford the desired benzoxazole methyl ester.

The benzoxazole methyl ester was dissolved in a mixture of THF:MeOH:H$_2$O (3:1:1, 0.07 M) and treated with LiOH.H$_2$O (4 equiv). The reaction was stirred at ambient temperature and monitored by TLC. Upon completion, the mixture was acidified to pH 2 with 1 N HCl and extracted with EtOAc (4×). The combined organic layers were dried over MgSO$_4$, filtered and concentrated. The residue was purified by preparative thin layer chromatography (4.9% MeOH, 95% CH$_2$Cl$_2$, 0.1% HOAc) to give the product as a white solid.

4-Carboxy-2-(3,5-difluorophenyl)-benzoxazole (1). Prepared from 3-hydroxyanthranilic acid according to the general procedure, to afford 1 as a white solid (7.0 mg, 13%). Data for 1: $^1$H NMR (500 MHz, DMSO-d$_6$) δ 13.70-12.50 (br. s, 1H, CO$_2$H), 8.04 (AM$\underline{X}$, 1H, J=8.1 Hz, Ar), 7.94 (A$\underline{M}$X, 1H, J=7.3 Hz, Ar), 7.84 (br. d, 2H, J=5.6 Hz, Ar), 7.62-7.58 (m, 1H, Ar), 7.56 ($\underline{A}$MX, 1H, J=7.3, 8.1 Hz, Ar); $^{13}$C NMR (125 MHz, DMSO-d$_6$) δ 165.8, 162.7 (d, J=248 Hz), 162.6 (d, J=248 Hz), 161.1, 151.0, 140.3, 129.3, 127.0, 125.8, 123.6, 115.2, 110.8 (d, J=28 Hz), 107.8 (t, J=26 Hz); HRMS (MALDI-FTMS) calcd. for C$_{14}$H$_7$F$_2$NO$_3$ (MH$^+$) 276.0467. found 276.0463.

4-Carboxy-2-(2,6-difluorophenyl)-benzoxazole (2). Prepared from 3-hydroxyanthranilic acid according to the general procedure, to afford 2 as a white solid (8.2 mg, 15%). Data for 2: $^1$H NMR (500 MHz, DMSO-d$_6$) δ 13.00 (br. s, 1H, CO$_2$H), 8.06 (AM$\underline{X}$, 1H, J=8.1 Hz, Ar), 7.94 (A$\underline{M}$X, 1H, J=7.6 Hz, Ar), 7.80-7.74 (m, 1H, Ar), 7.57 ($\underline{A}$MX, 1H, J=7.6, 8.1 Hz, Ar), 7.40-7.38 (m, 2H, Ar); $^{13}$C NMR (125 MHz, DMSO-d$_6$) □ 166.1, 160.4 (d, J=256 Hz), 160.3 (d, J=256 Hz), 154.9, 150.6, 139.6, 134.7 (t, J=10 Hz), 126.8, 125.8, 114.8, 112.8 (d, J=22 Hz), 105.2 (t, J=16 Hz); HRMS (MALDI-FTMS) calcd. for C$_{14}$H$_7$F$_2$NO$_3$ (MH$^+$) 276.0467. found 276.0461.

4-Carboxy-2-[(3-trifluoromethyl)phenyl]-benzoxazole (3). Prepared from 3-hydroxyanthranilic acid according to the general procedure, to afford 3 as a white solid (9.5 mg, 15%). Data for 3: $^1$H NMR (500 MHz, DMSO-d$_6$) δ 13.70-12.80 (br. s, 1H, CO$_2$H), 8.50 (AB$\underline{X}$, 1H, J=7.8 Hz, Ar), 8.43 (s, 1H, Ar), 8.06 (AM$\underline{X}$, 1H, J=8.1 Hz, Ar), 8.03 (A$\underline{B}$X, 1H, J=8.1 Hz, Ar), 7.94 (A$\underline{M}$X, 1H, J=7.8 Hz, Ar), 7.88 ($\underline{A}$BX, 1H, J=7.8 Hz, Ar), 7.54 ($\underline{A}$MX, 1H, J=8.1 Hz, Ar); $^{13}$C NMR (125 MHz, DMSO-d$_6$) δ 165.8, 161.9, 151.0, 140.6, 131.4, 130.8, 130.0 (q, J=33 Hz), 128.7 (d, J=4 Hz), 127.2, 127.0, 125.5, 123.8, 123.7 (q, J=273 Hz), 123.2, 115.2; HRMS (MALDI-FTMS) calcd. for C$_{15}$H$_8$F$_3$NO$_3$ (MH$^+$) 308.0529. found 308.0535.

4-Carboxy-2-[(2-trifluoromethyl)phenyl]-benzoxazole (4). Prepared from 3-hydroxyanthranilic acid according to the general procedure, to afford 4 as a white solid (15.2 mg, 25%). Data for 4: $^1$H NMR (600 MHz, DMSO-d$_6$) δ 13.15 (br. s, 1H, CO$_2$H), 8.18 (d, 1H, J=7.6 Hz, Ar), 8.06 (AM$\underline{X}$, 1H, J=0.9, 8.2 Hz, Ar), 8.02 (d, 1H, J=7.9 Hz, Ar), 7.96 (AMX, 1H, J=0.9, 7.9 Hz, Ar), 7.94-7.87 (m, 2H, Ar), 7.58 (AMX, 1H, J=8.2 Hz, Ar); $^{13}$C NMR (150 MHz, DMSO-d$_6$) δ 165.8, 161.6, 151.2, 140.0, 133.0, 132.6, 132.3, 127.6 (q, J=32 Hz), 127.2 (q, J=6 Hz), 127.0, 125.6, 124.9, 123.5, 123.4 (q, J=273 Hz), 115.2; HRMS (MALDI-FTMS) calcd. for C$_{15}$H$_8$F$_3$NO$_3$ (MH$^+$) 308.0529. found 308.0531.

4-Carboxy-2-(3,5-dichlorophenyl)-benzoxazole (5). Prepared from 3-hydroxyanthranilic acid according to the general procedure, to afford 5 as a white solid (8.0 mg, 13%). Data for 5: $^1$H NMR (600 MHz, DMSO-d$_6$) δ 13.60-12.60 (br. s, 1H, CO$_2$H), 8.16 (A$_2$M, 2H, J=2.0 Hz, Ar), 8.05 (AMX, 1H, J=0.9, 8.2 Hz, Ar), 7.96 (A$_2$M, 1H, J=2.0 Hz, Ar), 7.94 (AMX, 1H, J=0.9, 7.6 Hz, Ar), 7.56 (AMX, 1H, J=7.9 Hz, Ar); $^{13}$C NMR (150 MHz, DMSO-d$_6$) δ 165.8, 160.8, 151.0, 140.4, 135.2, 131.5, 129.4, 127.0, 126.3, 125.9, 125.8, 123.6, 115.2; HRMS (MALDI-FTMS) calcd. for C$_{14}$H$_7$Cl$_2$NO$_3$ (MH$^+$) 307.9876. found 307.9876.

4-Carboxy-2-(2,6-dichlorophenyl)-benzoxazole (6). Prepared from 3-hydroxyanthranilic acid according to the general procedure, to afford 6 as a white solid (5.2 mg, 8%). Data for 6: $^1$H NMR (600 MHz, DMSO-d$_6$) δ 13.80-12.50 (br. s, 1H, CO$_2$H), 8.07 (AMX, 1H, J=8.2 Hz, Ar), 7.95 (AMX, 1H, J=7.9 Hz, Ar), 7.77-7.71 (m, 3H, Ar), 7.59 (AMX, 1H, J=7.9, 8.2 Hz, Ar); $^{13}$C NMR (150 MHz, DMSO-d$_6$) δ 165.8, 158.2, 150.8, 139.3, 134.8, 134.0, 128.7, 126.8, 126.7, 125.9, 122.4; HRMS (MALDI-FTMS) calcd. for C$_{14}$H$_7$Cl$_2$NO$_3$ (MH$^+$) 307.9876. found 307.9880.

4-Carboxy-2-phenyl-benzoxazole (7). Prepared from 3-hydroxyanthranilic acid according to the general procedure, to afford 7 as a white solid (10.2 mg, 21%). Data for 7: $^1$H NMR (600 MHz, DMSO-d$_6$) δ 13.50-12.60 (br. s, 1H, CO$_2$H), 8.24-8.22 (m, 2H, Ar), 8.03 (AMX, 1H, J=0.9, 8.2 Hz, Ar), 7.91 (AMX, 1H, J=0.9, 7.9 Hz, Ar), 7.68-7.61 (m, 3H, Ar), 7.51 (AMX, 1H, J=7.9, 8.2 Hz, Ar); $^{13}$C NMR (150 MHz, DMSO-d$_6$) δ 166.0, 163.4, 151.0, 140.8, 132.4, 129.4, 127.6, 126.7, 126.1, 125.0, 123.0, 115.0; HRMS (MALDI-FTMS) calcd. for C$_{14}$H$_9$NO$_3$ (MH$^+$) 240.0655. found 240.0656.

5-Carboxy-2-(3,5-difluorophenyl)-benzoxazole (8). Prepared from 3-amino-4-hydroxybenzoic acid according to the general procedure, to afford 8 as a white solid (10.2 mg, 19%). Data for 8: $^1$H NMR (600 MHz, DMSO-d$_6$) δ 13.60-12.80 (br. s, 1H, CO$_2$H), 8.32 (ABM, 1H, J=1.5 Hz, Ar), 8.07 (ABM, 1H, J=1.5, 8.5 Hz, Ar), 7.90 (ABM, 1H, J=8.5 Hz, Ar), 7.86-7.85 (m, 2H, Ar), 7.60 (tt, 1H, J=2.4, 9.2 Hz, Ar); $^{13}$C NMR (150 MHz, DMSO-d$_6$) δ 166.8, 162.8 (d, J=248 Hz), 162.7 (d, J=248 Hz), 161.5, 153.0, 141.2, 129.1 (t, J=11 Hz), 128.2, 127.7, 121.4, 111.2, 110.8 (d, J=23 Hz), 110.7 (d, J=22 Hz), 107.8 (t, J=26 Hz); HRMS (MALDI-FTMS) calcd. for C$_{14}$H$_7$F$_2$NO$_3$ (MH$^+$) 276.0467. found 276.0469.

5-Carboxy-2-(2,6-difluorophenyl)-benzoxazole (9). Prepared from 3-amino-4-hydroxybenzoic acid according to the general procedure, to afford 9 as a white solid (6.8 mg, 12%). Data for 9: $^1$H NMR (600 MHz, DMSO-d$_6$) δ 13.50-12.80 (br. s, 1H, CO$_2$H), 8.39 (ABM, 1H, J=0.7, 1.6 Hz, Ar), 8.10 (ABM, 1H, J=1.6, 8.7 Hz, Ar), 7.95 (ABM, 1H, J=0.7, 8.7 Hz, Ar), 7.77 (m, 1H, Ar), 7.40 (t, 2H, J=8.8 Hz, Ar); $^{13}$C NMR (150 MHz, DMSO-d$_6$) δ 166.8, 160.4 (d, J=257 Hz), 160.3 (d, J=257 Hz), 155.4, 152.6, 140.8, 134.8 (t, J=11 Hz), 128.2, 127.7, 121.6, 113.0 (d, J=22 Hz), 112.9 (d, J=22 Hz), 111.2, 104.9; HRMS (MALDI-FTMS) calcd. for C$_{14}$H$_7$F$_2$NO$_3$ (MH$^+$) 276.0467. found 276.0467.

5-Carboxy-2-[(3-trifluoromethyl)phenyl]-benzoxazole (10). Prepared from 3-amino-4-hydroxybenzoic acid according to the general procedure, to afford 10 as a white solid (6.7 mg, 11%). Data for 10: $^1$H NMR (500 MHz, DMSO-d$_6$) δ 13.30-12.80 (br. s, 1H, CO$_2$H), 8.51 (ABX, 1H, J=7.8 Hz, Ar), 8.45 (s, 1H, Ar), 8.35 (ABM, 1H, J=1.7 Hz, Ar), 8.08 (ABM, 1H, J=1.7, 8.6 Hz, Ar), 8.04 (ABX, 1H, J=7.8 Hz, Ar), 7.93 (ABM, 1H, J=8.6 Hz, Ar), 7.89 (ABX, 1H, J=7.8 Hz, Ar); $^{13}$C NMR (125 MHz, DMSO-d$_6$) δ 166.8, 162.2, 153.1, 141.4, 131.4, 130.9, 130.1 (q, J=33 Hz), 128.8, 128.2, 127.5, 127.1, 123.8 (q, J=4 Hz), 123.7 (q, J=273 Hz), 121.3, 111.2; HRMS (MALDI-FTMS) calcd. for C$_{15}$H$_8$F$_3$NO$_3$ (MH$^+$) 308.0529. found 308.0530.

5-Carboxy-2-[(2-trifluoromethyl)phenyl]-benzoxazole (11). Prepared from 3-amino-4-hydroxybenzoic acid according to the general procedure, to afford 11 as a white solid (10.3 mg, 17%). Data for 11: $^1$H NMR (600 MHz, DMSO-d$_6$) δ 13.19 (br. s, 1H, CO$_2$H), 8.38 (m, 1H, Ar), 8.19 (d, 1H, J=7.6 Hz, Ar), 8.09 (dd, 1H, J=1.8, 8.5 Hz, Ar), 8.03 (d, 1H, J=7.9 Hz, Ar), 7.94-7.88 (m, 3H, Ar); $^{13}$C NMR (150 MHz, DMSO-d$_6$) δ 166.8, 161.6, 153.2, 141.1, 133.1, 132.5, 132.4, 128.2, 127.6, 127.5 (q, J=32 Hz), 127.2 (q, J=6 Hz), 124.7, 123.4 (q, J=274 Hz), 121.6, 111.2; HRMS (MALDI-FTMS) calcd. for C$_{15}$H$_8$F$_3$NO$_3$ (MH$^+$) 308.0529. found 308.0531.

5-Carboxy-2-(3,5-dichlorophenyl)-benzoxazole (12). Prepared from 3-amino-4-hydroxybenzoic acid according to the general procedure, to afford 12 as a white solid (7.3 mg, 12%). Data for 12: $^1$H NMR (600 MHz, DMSO-d$_6$) δ 13.14 (br. s, 1H, CO$_2$H), 8.33 (AMX, 1H, J=0.6, 1.8 Hz, Ar), 8.16 (AM, 2H, J=1.8 Hz, Ar), 8.08 (AMX, 1H, J=1.8, 8.5 Hz, Ar), 7.95 (AM, 1H, J=1.8 Hz, Ar), 7.91 (AMX, 1H, J=0.6, 8.5 Hz, Ar); $^{13}$C NMR (150 MHz, DMSO-d$_6$) δ 166.7, 161.1, 153.0, 141.3, 135.2, 131.6, 129.2, 128.2, 127.7, 125.9, 121.4, 111.3; HRMS (MALDI-FTMS) calcd. for C$_{14}$H$_7$Cl$_2$NO$_3$ (MH$^+$) 307.9876. found 307.9879.

5-Carboxy-2-(2,6-dichlorophenyl)-benzoxazole (13). Prepared from 3-amino-4-hydroxybenzoic acid according to the general procedure, to afford 13 as a white solid (10.8 mg, 18%). Data for 13: $^1$H NMR (600 MHz, DMSO-d$_6$) δ 13.08 (br. s, 1H, CO$_2$H), 8.43 (AMX, 1H, J=0.6, 1.8 Hz, Ar), 8.13 (AMX, 1H, J=1.8, 8.5 Hz, Ar), 7.98 (AMX, 1H, J=0.6, 8.5 Hz, Ar), 7.77-7.72 (m, 3H, Ar); $^{13}$C NMR (150 MHz, DMSO-d$_6$) δ 166.7, 158.6, 152.8, 140.4, 134.8, 134.2, 128.8, 128.4, 127.8, 126.2, 121.8, 111.5; HRMS (MALDI-FTMS) calcd. for C$_{14}$H$_7$Cl$_2$NO$_3$ (MH$^+$) 307.9876. found 307.9879.

5-Carboxy-2-phenyl-benzoxazole (14). Prepared from 3-amino-4-hydroxybenzoic acid according to the general procedure, to afford 14 as a white solid (11.5 mg, 24%). Data for 14: $^1$H NMR (600 MHz, DMSO-d$_6$) δ 13.12 (br. s, 1H, CO$_2$H), 8.30 (ABX, 1H, J=1.8 Hz, Ar), 8.20 (dt, 2H, J=1.5, 6.7 Hz, Ar), 8.03 (ABX, 1H, J=1.8, 8.5 Hz, Ar), 7.87 (ABX, 1H, J=8.5 Hz, Ar), 7.67-7.60 (m, 3H, Ar); $^{13}$C NMR (150 MHz, DMSO-d$_6$) δ 166.9, 163.6, 153.0, 141.6, 132.4, 129.4, 127.9, 127.5, 127.0, 126.0, 121.0, 111.0; HRMS (MALDI-FTMS) calcd. for C$_{14}$H$_9$NO$_3$ (MH$^+$) 240.0655. found 240.0656.

6-Carboxy-2-(3,5-difluorophenyl)-benzoxazole (15). Prepared from 4-amino-3-hydroxybenzoic acid according to the general procedure, to afford 15 as a white solid (10.3 mg, 19%). Data for 15: $^1$H NMR (600 MHz, DMSO-d$_6$) δ 13.22 (br. s, 1H, CO$_2$H), 8.20 (ABM, 1H, J=1.5 Hz, Ar), 7.98 (ABM, 1H, J=1.5, 8.2 Hz, Ar), 7.86 (ABM, 1H, J=8.2 Hz, Ar), 7.79-7.78 (m, 2H, Ar), 7.57 (tt, 1H, J=2.4, 9.4 Hz, Ar); $^{13}$C NMR (150 MHz, DMSO-d$_6$) δ 166.7, 162.7 (d, J=248 Hz), 162.6 (d, J=248 Hz), 162.4, 150.0, 144.7, 129.0 (t, J=11 Hz), 128.7, 126.5, 120.0, 112.1, 110.9 (d, J=23 Hz), 110.8 (d, J=22 Hz), 108.0 (t, J=26 Hz); HRMS (MALDI-FTMS) calcd. for C$_{14}$H$_7$F$_2$NO$_3$ (MH$^+$) 276.0467. found 276.0468.

6-Carboxy-2-(2,6-difluorophenyl)-benzoxazole (16). Prepared from 4-amino-3-hydroxybenzoic acid according to the general procedure, to afford 16 as a white solid (8.5 mg, 15%). Data for 16: $^1$H NMR (600 MHz, DMSO-d$_6$) δ 13.25 (br. s, 1H, CO$_2$H), 8.30 (AB<u>M</u>, 1H, J=0.6, 1.5 Hz, Ar), 8.04 (A<u>B</u>M, 1H, J=1.5, 8.2 Hz, Ar), 7.96 (A<u>B</u>M, 1H, J=0.6, 8.2 Hz, Ar), 7.76 (m, 1H, Ar), 7.39 (t, 2H, J=8.8 Hz, Ar); $^{13}$C NMR (150 MHz, DMSO-d$_6$) δ 166.7, 160.4 (d, J=257 Hz), 160.3 (d, J=257 Hz), 156.6, 149.7, 144.2, 134.9 (t, J=11 Hz), 128.8, 126.4, 120.1, 113.1, 112.9, 112.2 (d, J=5 Hz), 105.0 (t, J=16 Hz); HRMS (MALDI-FTMS) calcd. for C$_{14}$H$_7$F$_2$NO$_3$ (MH$^+$) 276.0467. found 276.0466.

6-Carboxy-2-[(3-trifluoromethyl)phenyl]-benzoxazole (17). Prepared from 4-amino-3-hydroxybenzoic acid according to the general procedure, to afford 17 as a white solid (7.4 mg, 12%). Data for 17: $^1$H NMR (600 MHz, DMSO-d$_6$) δ 13.20 (br. s, 1H, CO$_2$H), 8.48 (AB<u>X</u>, 1H, J=7.9 Hz, Ar), 8.41 (s, 1H, Ar), 8.28 (AB<u>M</u>, 1H, J=1.5 Hz, Ar), 8.03 (A<u>B</u>X, 1H, J=7.9 Hz, Ar), 8.02 (A<u>B</u>M, 1H, J=1.5, 8.2 Hz, Ar), 7.90 (A<u>B</u>M, 1H, J=8.2 Hz, Ar), 7.86 (<u>A</u>BX, 1H, J=7.9 Hz, Ar); $^{13}$C NMR (150 MHz, DMSO-d$_6$) δ 168.0, 164.6, 151.4, 146.2, 132.8, 132.2, 131.4 (q, J=32 Hz), 130.2, 129.8, 128.4, 127.8, 125.2, 125.0 (q, J=272 Hz), 121.2, 113.6; HRMS (MALDI-FTMS) calcd. for C$_{15}$H$_8$F$_3$NO$_3$ (MH$^+$) 308.0529. found 308.0530. HRMS (MALDI-FTMS) calcd. for C$_{15}$H$_8$F$_3$NO$_3$ (MH$^+$) 308.0529. found 308.0531.

6-Carboxy-2-[(2-trifluoromethyl)phenyl]-benzoxazole (18). Prepared from 4-amino-3-hydroxybenzoic acid according to the general procedure, to afford 18 as a white solid (6.6 mg, 11%). Data for 18: $^1$H NMR (600 MHz, DMSO-d$_6$) δ 13.22 (br. s, 1H, CO$_2$H), 8.30 (AB<u>X</u>, 1H, J=0.6, 1.5 Hz, Ar), 8.20 (d, 1H, J=7.3 Hz, Ar), 8.06 (<u>A</u>BX, 1H, J=1.5, 8.2 Hz, Ar), 8.04 (d, 1H, J=7.9 Hz, Ar), 7.98 (A<u>B</u>X, 1H, J=0.6, 8.2 Hz, Ar), 7.94 (t, 1H, J=7.3 Hz, Ar), 7.90 (t, 1H, J=7.9 Hz, Ar); $^{13}$C NMR (150 MHz, DMSO-d$_6$) δ 168.0, 164.0, 151.6, 145.9, 133.8, 130.0, 129.0 (q, J=32 Hz), 128.6 (q, J=6), 127.7, 126.0, 124.7 (q, J=273 Hz), 121.6, 113.6; HRMS (MALDI-FTMS) calcd. for C$_{15}$H$_8$F$_3$NO$_3$ (MH$^+$) 308.0529. found 308.0530.

6-Carboxy-2-(3,5-dichlorophenyl)-benzoxazole (19). Prepared from 4-amino-3-hydroxybenzoic acid according to the general procedure, to afford 19 as a white solid (6.0 mg, 10%). Data for 19: $^1$H NMR (600 MHz, DMSO-d$_6$) δ 13.20 (br. s, 1H, CO$_2$H), 8.17 (AB<u>X</u>, 1H, J=0.6, 1.5 Hz, Ar), 8.00 (A<u>B</u>, 1H, J=2.0 Hz, Ar), 7.96 (<u>A</u>BX, 1H, J=1.5, 8.5 Hz, Ar), 7.83 (<u>A</u>B, 1H, J=2.0 Hz, Ar), 7.82 (A<u>B</u>X, 1H, J=0.6, 8.5 Hz, Ar); $^{13}$C NMR (150 MHz, DMSO-d$_6$) δ 166.6, 161.9, 150.0, 144.6, 135.1, 131.6, 129.0, 128.7, 126.4, 125.8, 119.9, 112.1; HRMS (MALDI-FTMS) calcd. for C$_{14}$H$_7$Cl$_2$NO$_3$ (MH$^+$) 307.9876. found 307.9879.

6-Carboxy-2-(2,6-dichlorophe2nyl)-benzoxazole (20). Prepared from 4-amino-3-hydroxybenzoic acid according to the general procedure, to afford 20 as a white solid (12.7 mg, 21%). Data for 20: $^1$H NMR (500 MHz, DMSO-d$_6$) δ 13.27 (br. s, 1H, CO$_2$H), 8.38 (AB<u>X</u>, 1H, J=0.5, 1.5 Hz, Ar), 8.09 (A<u>B</u>X, 1H, J=1.5, 8.3 Hz, Ar), 8.02 (A<u>B</u>X, 1H, J=8.3, 0.5 Hz, Ar), 7.78-7.71 (m, 3H, Ar); $^{13}$C NMR (125 MHz, DMSO-d$_6$) δ 166.6, 159.8, 150.0, 143.8, 134.8, 134.2, 129.1, 128.8, 126.4, 126.3, 120.4, 112.6; HRMS (MALDI-FTMS) calcd. for C$_{14}$H$_7$Cl$_2$NO$_3$ (MH$^+$) 307.9876. found 307.9877.

6-Carboxy-2-phenyl-benzoxazole (21). Prepared from 4-amino-3-hydroxybenzoic acid according to the general procedure, to afford 21 as a white solid (7.0 mg, 15%). Data for 21: $^1$H NMR (600 MHz, DMSO-d$_6$) δ 13.16 (br. s, 1H, CO$_2$H), 8.27 (d, 1H, J=0.9 Hz, Ar), 8.25-8.22 (m, 2H, Ar), 8.01 (<u>dd</u>, 1H, J=1.5, 8.5 Hz, Ar), 7.89 (d, 1H, J=8.5 Hz, Ar), 7.69-7.62 (m, 3H, Ar); $^{13}$C NMR (150 MHz, DMSO-d$_6$) δ 166.8, 164.7, 150.0, 145.2, 132.6, 129.4, 128.0, 127.6, 126.3, 126.0, 119.6, 112.0; HRMS (MALDI-FTMS) calcd. for C$_{14}$H$_9$NO$_3$ (MH$^+$) 240.0655. found 240.0655.

7-Carboxy-2-(3,5-difluorophenyl)-benzoxazole (22). Prepared from 3-aminosalicylic acid according to the general procedure, to afford 22 as a white solid (8.8 mg, 16%). Data for 22: $^1$H NMR (600 MHz, DMSO-d$_6$) δ 13.55 (br. s, CO$_2$H), 8.10 (AM<u>X</u>, 1H, J=1.2, 7.9 Hz, Ar), 7.97 (A<u>M</u>X, 1H, J=1.2, 7.9 Hz, Ar), 7.80-7.79 (m, 2H, Ar), 7.63 (tt, 1H, J=2.4, 9.2 Hz, Ar), 7.55 (<u>A</u>MX, 1H, J=7.9 Hz, Ar); $^{13}$C NMR (150 MHz, DMSO-d$_6$) δ 164.5, 162.8 (d, J=248 Hz), 162.6 (d, J=248 Hz), 160.9, 149.2, 142.6, 129.2, 128.0, 125.2, 124.9, 116.1, 110.6 (d, J=28 Hz), 107.7 (q, J=25 Hz); HRMS (MALDI-FTMS) calcd. for C$_{14}$H$_7$F$_2$NO$_3$ (MH$^+$) 276.0467. found 276.0469.

7-Carboxy-2-(2,6-difluorophenyl)-benzoxazole (23). Prepared from 3-aminosalicylic acid according to the general procedure, to afford 23 as a white solid (7.3 mg, 13%). Data for 23: $^1$H NMR (600 MHz, DMSO-d$_6$) δ 13.48 (br. s, 1H, CO$_2$H), 8.16 (A<u>B</u>X, 1H, J=1.2, 8.2 Hz, Ar), 8.00 (A<u>B</u>X, 1H, J=1.2, 7.6 Hz, Ar), 7.78 (m, 1H, Ar), 7.57 (AB<u>X</u>, 1H, J=7.6, 8.2 Hz, Ar), 7.40 (t, 2H, J=8.5 Hz, Ar); $^{13}$C NMR (150 MHz, DMSO-d$_6$) δ 164.5, 160.4 (d, J=256 Hz), 160.3 (d, J=257 Hz), 154.9, 148.9, 142.1, 134.8 (t, J=10 Hz), 128.0, 125.1, 125.0, 116.0, 113.0 (d, J=22 Hz), 112.9 (q, J=21 Hz), 105.1 (t, J=17 Hz); HRMS (MALDI-FTMS) calcd. for C$_{14}$H$_7$F$_2$NO$_3$ (MH$^+$) 276.0467. found 276.0467.

7-Carboxy-2-[(3-trifluoromethyl)phenyl]-benzoxazole (24). Prepared from 3-aminosalicylic acid according to the general procedure, to afford 24 as a white solid (7.9 mg, 13%). Data for 24: $^1$H NMR (600 MHz, DMSO-d$_6$) δ 13.51 (br. s, CO$_2$H), 8.48 (AB<u>X</u>, 1H, J=8.2 Hz, Ar), 8.40 (s, 1H, Ar), 8.10 (AM<u>X</u>, 1H, J=1.2, 7.9 Hz, Ar), 8.05 (A<u>B</u>X, 1H, J=7.9 Hz, Ar), 7.96 (A<u>M</u>X, 1H, J=1.2, 7.6 Hz, Ar), 7.94 (A<u>B</u>X, 1H, J=7.9 Hz, Ar), 7.54 (<u>A</u>MX, 1H, J=7.9, 7.6 Hz, Ar); $^{13}$C NMR (150 MHz, DMSO-d$_6$) δ 164.6, 161.7, 149.3, 142.7, 131.3, 131.0, 130.0 (q, J=32 Hz), 128.6 (d, J=3 Hz), 127.7, 127.2, 125.0, 124.8, 123.7 (q, J=272 Hz), 123.5, 116.0; HRMS (MALDI-FTMS) calcd. for C$_{15}$H$_8$F$_3$NO$_3$ (MH$^+$) 308.0529. found 308.0532.

7-Carboxy-2-[(2-trifluoromethyl)phenyl]-benzoxazole (25). Prepared from 3-aminosalicylic acid according to the general procedure, to afford 25 as a white solid (13.8 mg, 22%). Data for 25: $^1$H NMR (600 MHz, DMSO-d$_6$) δ 13.46 (br. s, 1H, CO$_2$H), 8.18 (d, 1H, J=7.6 Hz, Ar), 8.14 (AM<u>X</u>, 1H, J=1.2, 7.9 Hz, Ar), 8.03 (d, 1H, J=7.9 Hz, Ar), 7.98 (A<u>M</u>X, 1H, J=1.2, 7.6 Hz, Ar), 7.94 (t, 1H, J=7.3 Hz, Ar), 7.89 (t, 1H, J=7.6 Hz, Ar), 7.56 (<u>A</u>MX, 1H, J=7.9 Hz, Ar); $^{13}$C NMR (150 MHz, DMSO-d$_6$) δ 164.6, 161.1, 149.3, 142.4, 133.0, 132.4, 132.2, 127.8, 127.6, 127.2 (q, J=6 Hz), 125.0, 124.9, 123.4 (q, J=273 Hz), 116.2; HRMS (MALDI-FTMS) calcd. for C$_{15}$H$_8$F$_3$NO$_3$ (MH$^+$) 308.0529. found 308.0534.

7-Carboxy-2-(3,5-dichlorophenyl)-benzoxazole (26). Prepared from 3-aminosalicylic acid according to the general procedure, to afford 26 as a white solid (7.0 mg, 11%). Data for 26: $^1$H NMR (600 MHz, DMSO-d$_6$) δ 14.00-12.80 (br. S, CO$_2$H), 8.10-8.08 (m, 3H, Ar), 7.98-7.96 (m, 2H, Ar), 7.55 (t, 1H, J=7.8 Hz, Ar); $^{13}$C NMR (150 MHz, DMSO-d$_6$) δ 164.5, 160.5, 149.2, 142.6, 135.2, 131.5, 129.4, 128.0, 125.6, 125.2, 124.8, 116.2; HRMS (MALDI-FTMS) calcd. for C$_{14}$H$_7$Cl$_2$NO$_3$ (MH$^+$) 307.9876. found 307.9874.

7-Carboxy-2-(2,6-dichlorophenyl)-benzoxazole (27). Prepared from 3-aminosalicylic acid according to the general procedure, to afford 27 as a white solid (10.3 mg, 17%). Data for 27: $^1$H NMR (600 MHz, DMSO-d$_6$) δ 13.90-13.10 (br. S, CO$_2$H), 8.16 (AM<u>X</u>, 1H, J=7.9 Hz, Ar), 8.02 (A<u>M</u>X, 1H, J=7.9 Hz, Ar), 7.78-7.72 (m, 3H, Ar), 7.60 (<u>A</u>MX, 1H, J=7.9 Hz, Ar); $^{13}$C NMR (150 MHz, DMSO-d$_6$) δ 164.4, 158.3, 149.1, 141.7, 134.9, 134.2, 128.8, 128.2, 126.5, 125.3, 125.2, 116.2; HRMS (MALDI-FTMS) calcd. for $C_{14}H_7Cl_2NO_3$ (MH$^+$) 307.9876. found 307.9875.

7-Carboxy-2-phenyl-benzoxazole (28). Prepared from 3-aminosalicylic acid according to the general procedure, to afford 28 as a white solid (13.1 mg, 27%). Data for 28: $^1$H NMR (600 MHz, DMSO-d$_6$) δ 13.48 (br. s, 1H, CO$_2$H), 8.20-8.19 (m, 2H, Ar), 8.05 (AMX, 1H, J=1.2, 7.9 Hz, Ar), 7.92 (AMX, 1H, J=1.2, 7.6 Hz, Ar), 7.66-7.62 (m, 3H, Ar), 7.50 (AMX, 1H, J=7.9 Hz, Ar); $^{13}$C NMR (150 MHz, DMSO-d$_6$) δ 164.8, 163.1, 149.2, 142.9, 132.2, 129.4, 127.4, 127.2, 126.0, 124.7, 124.4, 115.8; HRMS (MALDI-FTMS) calcd. for $C_{14}H_9NO_3$ (MH$^+$) 240.0655. found 240.0656.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method of treating a transthyretin amyloid disease, the method comprising orally administering 250 mg of 2',4'-difluoro-4-hydroxy-[1,1'-biphenyl]-3-carboxylic acid twice per day to a subject diagnosed as having a transthyretin amyloid disease.

2. The method of claim 1, wherein the transthyretin amyloid disease is familial amyloid polyneuropathy.

3. The method of claim 1, wherein the transthyretin amyloid disease is familial amyloid cardiomyopathy.

4. The method of claim 1, wherein the transthyretin amyloid disease is senile systemic amyloidosis.

5. The method of claim 1, wherein the transthyretin amyloid disease is cardiac amyloidosis following liver transplantation.

* * * * *